United States Patent
Einav et al.

(10) Patent No.: US 8,012,107 B2
(45) Date of Patent: Sep. 6, 2011

(54) METHODS AND APPARATUS FOR REHABILITATION AND TRAINING

(75) Inventors: Omer Einav, Emek Hefer (IL); Haim Einav, Tel-Aviv (IL); Benny Rousso, Rishon-LeZion (IL); Doron Shabanov, Tzur-Yigal (IL); Eran Katzir, Rosh HaAyin (IL); Gad Binyamini, Moshav Hagor (IL)

(73) Assignee: Motorika Limited, Hamilton (BM)

( * ) Notice: Subject to any disclaimer, the term of this patent is extended or adjusted under 35 U.S.C. 154(b) by 885 days.

(21) Appl. No.: 10/597,675

(22) PCT Filed: Feb. 4, 2005

(86) PCT No.: PCT/IL2005/000141
§ 371 (c)(1),
(2), (4) Date: Jun. 18, 2007

(87) PCT Pub. No.: WO2005/074372
PCT Pub. Date: Aug. 18, 2005

(65) Prior Publication Data
US 2007/0282228 A1 Dec. 6, 2007

Related U.S. Application Data

(60) Provisional application No. 60/542,022, filed on Feb. 5, 2004, provisional application No. 60/566,078, filed on Apr. 29, 2004, provisional application No. 60/566,079, filed on Apr. 29, 2004, provisional application No. 60/604,615, filed on Aug. 25, 2004, provisional application No. 60/633,428, filed on Dec. 7, 2004, provisional application No. 60/633,429, filed on Dec. 7, 2004, provisional application No. 60/633,442, filed on Dec. 7, 2004.

(51) Int. Cl.
*A61F 5/00* (2006.01)

(52) U.S. Cl. ................... 601/5; 602/16; 602/20
(58) Field of Classification Search ........... 601/5, 7; 128/882; 602/16, 20–23, 26–28, 5
See application file for complete search history.

(56) References Cited

U.S. PATENT DOCUMENTS
3,919,691 A 11/1975 Noll
(Continued)

FOREIGN PATENT DOCUMENTS
EP 0304538 3/1989
(Continued)

OTHER PUBLICATIONS
Translation of Notification of Reasons of Rejection Dated Jun. 12, 2009 From the Japanese Patent Office Re.: Application No. 2006-552011.
(Continued)

*Primary Examiner* — Michael A. Brown

(57) ABSTRACT

A method of rehabilitation comprising: providing a first actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume; coupling said first actuator to a first point on a human body; providing a second actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume; coupling said second actuator to a second point on a human body; and applying different forces to said points using said actuators.

39 Claims, 40 Drawing Sheets

U.S. PATENT DOCUMENTS

| | | | |
|---|---|---|---|
| 3,929,462 A | 12/1975 | Karmin | |
| 4,499,900 A | 2/1985 | Petrofsky et al. | |
| 4,582,049 A | 4/1986 | Ylvisaker | |
| 4,685,928 A * | 8/1987 | Yaeger | 623/64 |
| 4,724,842 A | 2/1988 | Charters et al. | |
| 4,824,104 A | 4/1989 | Bloch | |
| 4,921,244 A | 5/1990 | Berroth | |
| 4,936,299 A | 6/1990 | Erlandson | |
| 5,048,826 A | 9/1991 | Ryan | |
| 5,070,873 A | 12/1991 | Graupe et al. | |
| 5,193,539 A | 3/1993 | Schulman et al. | |
| 5,193,540 A | 3/1993 | Schulman et al. | |
| 5,201,772 A | 4/1993 | Maxwell | |
| 5,211,161 A | 5/1993 | Stef | |
| 5,244,441 A * | 9/1993 | Dempster et al. | 482/9 |
| 5,269,318 A | 12/1993 | Nashner | |
| 5,282,460 A | 2/1994 | Boldt | |
| 5,312,439 A | 5/1994 | Loeb | |
| 5,324,316 A | 6/1994 | Schulman et al. | |
| 5,391,128 A | 2/1995 | DeBear | |
| 5,397,865 A | 3/1995 | Park | |
| 5,405,367 A | 4/1995 | Schulman et al. | |
| 5,413,611 A * | 5/1995 | Haslam et al. | 623/25 |
| 5,454,774 A | 10/1995 | Davis | |
| 5,466,213 A | 11/1995 | Hogan et al. | |
| 5,476,103 A | 12/1995 | Nahsner | |
| 5,476,428 A | 12/1995 | Potash et al. | |
| 5,616,104 A | 4/1997 | Mulenburg et al. | |
| 5,662,693 A * | 9/1997 | Johnson et al. | 607/49 |
| 5,690,389 A | 11/1997 | Ekman et al. | |
| 5,755,645 A | 5/1998 | Miller et al. | |
| 5,830,160 A | 11/1998 | Reinkensmeyer | |
| 5,836,304 A | 11/1998 | Kellinger et al. | |
| 5,846,086 A | 12/1998 | Bizzi et al. | |
| 5,853,353 A | 12/1998 | Blümel | |
| 5,919,115 A | 7/1999 | Horowitz et al. | |
| 5,954,621 A | 9/1999 | Jourtas et al. | |
| 6,004,244 A | 12/1999 | Simonson | |
| 6,035,465 A | 3/2000 | Rogozinski | |
| 6,051,017 A | 4/2000 | Loeb et al. | |
| 6,057,828 A | 5/2000 | Rosenberg et al. | |
| 6,061,004 A | 5/2000 | Rosenberg et al. | |
| 6,064,912 A | 5/2000 | Kenney | |
| 6,246,200 B1 | 6/2001 | Blumenkranz et al. | |
| 6,270,445 B1 | 8/2001 | Dean, Jr. et al. | |
| 6,379,393 B1 * | 4/2002 | Mavroidis et al. | 623/25 |
| 6,478,721 B1 | 11/2002 | Hunter | |
| 6,592,315 B2 | 7/2003 | Osborne, Jr. | |
| 6,645,126 B1 | 11/2003 | Martin et al. | |
| 6,774,885 B1 | 8/2004 | Even-Zohar | |
| 6,829,510 B2 | 12/2004 | Nathan et al. | |
| 7,381,192 B2 | 6/2008 | Brodard et al. | |
| 2002/0064438 A1 | 5/2002 | Osborne, Jr. | |
| 2003/0032524 A1 | 2/2003 | Lamar et al. | |
| 2003/0199370 A1 | 10/2003 | Bucay-Bissu | |
| 2004/0102723 A1 | 5/2004 | Horst | |
| 2004/0172097 A1 | 9/2004 | Brodard et al. | |
| 2004/0180768 A1 | 9/2004 | Almada | |
| 2004/0245838 A1 | 12/2004 | Chiu | |
| 2005/0261114 A1 | 11/2005 | Heitzman et al. | |
| 2006/0229164 A1 | 10/2006 | Einav | |
| 2006/0277074 A1 | 12/2006 | Einav et al. | |
| 2006/0293617 A1 | 12/2006 | Einav et al. | |
| 2007/0299371 A1 | 12/2007 | Einav et al. | |
| 2008/0132383 A1 | 6/2008 | Einav et al. | |
| 2008/0161733 A1 | 7/2008 | Einav et al. | |

FOREIGN PATENT DOCUMENTS

| | | |
|---|---|---|
| EP | 0569489 | 11/1993 |
| EP | 0862930 | 9/1998 |
| JP | 59-160455 | 9/1984 |
| JP | 60-200312 | 10/1985 |
| JP | 61-217174 | 9/1986 |
| JP | 61-265151 | 11/1986 |
| JP | 02-102652 | 4/1990 |
| JP | 05-007608 | 1/1993 |
| JP | 06-505407 | 6/1994 |
| JP | 07-163626 | 6/1995 |
| JP | 08-322189 | 12/1996 |
| JP | 3044600 | 10/1997 |
| JP | 3048540 | 2/1998 |
| JP | 11-155836 | 6/1999 |
| JP | 11-253504 | 9/1999 |
| JP | 2000-102523 | 4/2000 |
| JP | 2000-279463 | 10/2000 |
| JP | 2001-204850 | 7/2001 |
| JP | 3081786 | 8/2001 |
| JP | 2002-065891 | 3/2002 |
| JP | 2002-126019 | 5/2002 |
| JP | 2002-127058 | 5/2002 |
| JP | 3087629 | 5/2002 |
| JP | 2003-093451 | 4/2003 |
| JP | 2003-164544 | 6/2003 |
| WO | WO 92/13504 | 8/1992 |
| WO | WO 98/37926 | 9/1998 |
| WO | WO 98/43700 | 10/1998 |
| WO | WO 98/43701 | 10/1998 |
| WO | WO 98/46127 | 10/1998 |
| WO | WO 02/13673 | 2/2002 |
| WO | WO 02/092164 | 11/2002 |
| WO | WO 03/023546 | 3/2003 |
| WO | WO 2004/050172 | 6/2004 |
| WO | WO 2005/074369 | 8/2005 |
| WO | WO 2005/074370 | 8/2005 |
| WO | WO 2005/074371 | 8/2005 |
| WO | WO 2005/074373 | 8/2005 |
| WO | WO 2005/075155 | 8/2005 |
| WO | WO 2005/086574 | 9/2005 |
| WO | WO 2005/087307 | 9/2005 |
| WO | WO 2005/105203 | 11/2005 |
| WO | WO 2006/021952 | 3/2006 |
| WO | WO 2006/061834 | 6/2006 |
| WO | WO 2006/082584 | 8/2006 |

OTHER PUBLICATIONS

Translation of Notification of Reasons of Rejection Dated Sep. 14, 2009 From the Japanese Patent Office Re.: Application No. 2006-552014.

Communication Pursuant to Article 96(2) Dated Dec. 11, 2006 From the European Patent Office Re.: Application No. 05703180.9.

Examination Report Dated Oct. 23, 2008 From the Instituto Mexicano de la Propriedad Industrial Re.: Application No. PA/a/2006/008919.

Examination Report Dated Oct. 29, 2008 From the Instituto Mexicano de la Propriedad Industrial Re.: Application No. PA/a2006/008914.

International Preliminary Report on Patentability Dated Aug. 16, 2007 From the International Bureau of WIPO Re.: Application No. PCT/IL2006/000140.

International Preliminary Report on Patentability Dated Jan. 19, 2007 From the International Preliminary Examining Authority Re.: Application No. PCT/IL05/00138.

International Preliminary Report on Patentability Dated Apr. 26, 2007 From the International Bureau of WIPO Re.: Application No. PCT/IL2005/000139.

International Preliminary Report on Patentability Dated Sep. 29, 2008 From the International Preliminary Examining Authority Re.: Application No. PCT/IL06/00140.

International Search Report and the Written Opinion Dated Jan. 3, 2007 From the International Searching Authority Re.: Application No. PCT/IL06/00140.

Office Action Dated Sep. 26, 2008 From the State Intellectual Properety Office of the People's Republic of China Re.: Application No. 200580010391.4.

Official Action Dated Oct. 1, 2008 From the US Patent and Trademark Office Re.: U.S. Appl. No. 11/389,773.

Communication of Results From Examination Dated Oct. 23, 2008 From the Instituto Mexicano de la Propriedad Industrial Re.: Application No. PA/a/2006/008914 and Its Translation Into English.

Communication Pursuant to Article 94(3) EPC Dated Oct. 12, 2009 From the European Patent Office Re.: Application No. 06704564.1.

International Preliminary Report on Patentability Dated Mar. 8, 2007 From the International Bureau of WIPO Re.: Application No. PCT/IL2005/000906.
International Preliminary Report on Patentability Dated Jun. 12, 2006 From the International Preliminary Examining Authority Re.: Application No. PCT/IL2005/000442.
International Preliminary Report on Patentability Dated Aug. 17, 2006 From the International Bureau of WIPO Re.: Application No. PCT/IL2005/000136.
International Preliminary Report on Patentability Dated Aug. 17, 2006 From the International Bureau of WIPO Re.: Application No. PCT/IL2005/000140.
International Preliminary Report on Patentability Dated Aug. 17, 2006 From the International Bureau of WIPO Re.: Application No. PCT/IL2005/000141.
International Preliminary Report on Patentability Dated Jun. 21, 2007 From the International Bureau of WIPO Re.: Application No. PCT/IL2005/001318.
Notification of Reasons of Rejection Dated Jun. 4, 2009 From the Japanese Patent Office Re.: Application No. 2006-552011.
Notification of Reasons of Rejection Dated Sep. 14, 2009 From the Japanese Patent Office Re.: Application No. 2006-552015 and Its Translation Into English.
Official Action Dated Dec. 18, 2009 From the US Patent and Trademark Office Re.: U.S. Appl. No. 11/348,128.
Official Action Dated May 19, 2009 From the US Patent and Trademark Office Re.: U.S. Appl. No. 11/792,477.
Official Action Dated Oct. 23, 2008 From the Instituto Mexicano de la Propriedad Industrial, Divisional Direction of Patents Re.: Application No. PA/a/2006/008919 and Its Translation Into English.
Official Action Dated Jun. 24, 2009 From the US Patent and Trademark Office Re.: U.S. Appl. No. 11/207,655.
Official Action Dated Dec. 29, 2008 From the US Patent and Trademark Office Re.: U.S. Appl. No. 11/792,477.
Response Dated Feb. 7, 2010 to Notification of Reasons of Rejection Dated Sep. 14, 2009 From the Japanese Patent Office Re.: Application No. 2006-552015.
Response Dated Feb. 9, 2010 to Notification of Reasons of Rejection of Sep. 14, 2009 From the Japanese Patent Office Re.: Application No. 2006-552014.
Response Dated Apr. 13, 2010 to Communication Pursuant to Article 94(3) EPC of Oct. 12, 2009 From the European Patent Office Re.: Application No. 06704564.1.
Translation of Office Action Dated Jan. 21, 2009 From the Japanese Patent Office Re.: Application No. 2006-552008.
Supplementary Partial European Search Report and the European Search Opinion Dated Jul. 14, 2009 From the European Patent Office Re.: Application No. 06704564.1.
Pfurtscheller et al. "Brain Oscillations Control Hand Orthosis in A Tetraplegic", Neuroscience Letters, 292: 211-214, 2000.
International Preliminary Report on Patentability Dated Apr. 21, 2010 From the International Preliminary Examining Authority Re.: Application No. PCT/IL05/00138.
Backlife "The Backlife Idea", Product Information, <http://www.backlife.com>, 27 P., 2003.
Bak "The Complex Motion of Standing Still. Hydraulics, Sensors, and Human Modeling Dsta-Unified by Proprietary Software", <http://www.designnews.com/article/CA73202>, 5 P., 2001.
Burgar et al. "Development of Robots for Rehabilitation Therapy: The Palo Alto VA/Stanford Experience", Journal of Rehabilitation Research and Development, 37(6): 663-673, 2000.
Cameron et al. "Micromodular Implants to Provide Electrical Stimulation of Paralyzed Muscles and Limbs", IEEE Transactions on Biomedical Engineering, 44(9): 781-790, 1997. Abstract.
Graupe "EMG Pattern Analysis for Patient-Responsive Control of FES in Paraplegics for Walker-Supported Walking", IEEE Transactions on Biomedical Engineering, 36(7): 711-719, 1989. p. 711, 1-h Col., Paragraph 1 -r-h Col., Paragraph 1, Figs.3, 5, p. 716, 1-h Col., Figs.
Messinger "ReAbility Games: Island Hunt Catch'em Patrol Muzment", Detailed Specifications Document, NOKs Technologies, Version 1.0, 16 P., 2004.
Micromedical "BalanceQuest: Computerized Dynamic Posturography", Micromedical Technologies, <http://www.micromedial.com>, 6 P., 2001.
Motek "Motek Medical Rehabilitation: Rehabilitation", <http://www.e-motek.com>, 1 P.
Peasgood et al. "EMG-Controlled Dosed Loop Electrical Stimulation Using a Digital Signal Processor", Electronics Letters, 36(22): 1832-1833, 2000. p. 1832, 1-h Col., Paragraph 1, Fig.1, p. 1833, r-h Col., Paragraph 1.
Richardson et al. "Comparing Smooth Arm Movement With the Two-Thirds Power Law and the Related Segmented-Control Hypothesis", The Journal of Neuroscience, 22(18): 8201-8211, 2002.
Viviani et al. "Trajectory Determines Movement Dynamics", The Journal of Neuroscience, 7: 431-437, 1982.
Viviani et al. "Minimum-Jerk, Two-Thirds Power Law, and Isochrony: Converging Approaches to Movement Planning", Journal of Experimental Psychology: Human Perception and Performance, 17; 32-53, 1995. Abstract.
Office Action Dated Jun. 28, 2010 From the US Patent and Trademark Office Re.: U.S. Appl. No. 11/568,463.
Translation of Notification of Reasons of Rejection Dated May 26, 2010 From the Japanese Patent Office Re. Application No. 2006-552013.
Translation of Notice of Reason for Rejection Dated Jun. 4, 2010 From the Japanese Patent Office Re. Application No. 2007-529131.
Translation of Official Decision of Rejection Dated Oct. 29, 2010 From the Japanese Patent Office Re. Application No. 2007-529131.
Response Dated Aug. 4, 2010 to Notification of Reasons of Rejection of Mar. 9, 2010 From the Japanese Patent Office Re.: Application No. 2006-552008.
Translation of Notification of Reasons for Rejection Dated Jul. 12, 2010 From the Japanese Patent Office Re. Application No. 2006-215045.
International Preliminary Report on Patentability Dated May 11, 2006 From the International Preliminary Examining Authority Re.: Application No. PCT/IL2005/000137.
International Preliminary Report on Patentability Dated Jan. 23, 2006 From the International Preliminary Examining Authority Re.: Application No. PCT/IL2005/000135.
International Search Report and the Written Opinion Dated Sep. 6, 2006 From the International Searching Authority Re.: Application No. PCT/IL05/01318.
International Search Report and the Written Opinion Dated May 12, 2006 From the International Searching Authority Re.: Application No. PCT/IL05/00136.
International Search Report and the Written Opinion Dated Jul. 17, 2006 From the International Searching Authority Re.: Application No. PCT/IL05/00142.
International Search Report Dated Jun. 2, 2005 From the International Searching Authority Re.: Application No. PCT/IL2005/000139.
International Search Report Dated Feb. 3, 2006 From the International Searching Authority Re.: Application No. PCT/IL05/00140.
International Search Report Dated Jun. 8, 2006 From the International Searching Authority Re.: Application No. PCT/IL05/00906.
International Search Report Dated Nov. 17, 2005 From the International Searching Authority Re.: Application No. PCT/IL2005/000137.
International Search Report Dated Oct. 17, 2005 From the International Searching Authority Re.: Application No. PCT/IL05/00138.
International Search Report Dated Aug. 24, 2005 From the International Searching Authority Re.: Application No. PCT/IL2005/000442.
International Search Report Dated Nov. 28, 2005 From the International Searching Authority Re.: Application No. PCT/IL2005/00141.
International Searching Report Dated Jun. 3, 2005 From the International Searching Authority Re.: Application No. PCT/IL2005/000135.
Official Action Dated Feb. 7, 2008 From the US Patent and Trademark Office Re.: U.S. Appl. No. 11/389,773.
Official Action Dated Sep. 14, 2010 From the US Patent and Trademark Office Re. U.S. Appl. No. 10/597,756.

Official Action Dated May 19, 2008 From the US Patent and Trademark Office Re.: U.S. Appl. No. 11/207,655.
Official Action Dated Jul. 26, 2007 From the US Patent and Trademark Office Re.: U.S. Appl. No. 11/389,773.
Official Action Dated Sep. 30, 2008 From the US Patent and Trademark Office Re.: U.S. Appl. No. 11/207,655.
Response Dated Nov. 1, 2010 to Decision of Rejection of Jul. 9, 2010 From the Japanese Patent Office Re. Application No. 2006-552015.
Response Dated Sep. 20, 2010 to Notice of Reason for Rejection of Jun. 4, 2010 From the Japanese Patent Office Re. Application No. 2007-529131.
Response Dated Sep. 22, 2010 to Notification of Reasons of Rejection of May 26, 2010 From the Japanese Patent Office Re. Application No. 2006-552013.
Response Dated Sep. 26, 2010 to Notification of Reason for Rejection of Jul. 9, 2010 From the Japanese Patent Office Re. Application No. 2006-552014.
Response Dated Sep. 27, 2010 to Notification of Reasons for Rejection of Jul. 12, 2010 From the Japanese Patent Office Re. Application No. 2006-215045.
Response Dated Sep. 27, 2010 to Official Action of Jun. 28, 2010 From the US Patent and Trademark Office Re.: U.S. Appl. No. 11/568,463.
Supplementary Partial European Search Report Dated Jan. 29, 2008 From the European Patent Office Re.: Application No. 05774725.5.
Translation of Decision of Rejection Dated Jul. 9, 2010 From the Japanese Patent Office Re. Application No. 2006-552015.
Translation of Notification of Reason for Rejection Dated Jul. 9, 2010 From the Japanese Patent Office Re. Application No. 2006-552014.
Translation of Notification of Reason for Rejection Dated Aug. 13, 2010 From the Japanese Patent Office Re. Application No. 2006-552009.
Written Opinion Dated Jun. 2, 2005 From the International Searching Authority Re.: Application No. PCT/IL2005/000139.
Written Opinion Dated Feb. 3, 2006 From the International Searching Authority Re.: Application No. PCT/IL05/00140.
Written Opinion Dated Jun. 3, 2005 From the International Searching Authority Re.: Application No. PCT/IL2005/000135.
Written Opinion Dated Jun. 8, 2006 From the International Searching Authority Re.: Application No. PCT/IL05/00906.
Written Opinion Dated Nov. 17, 2005 From the International Searching Authority Re.: Application No. PCT/IL2005/000137.
Written Opinion Dated Oct. 17, 2005 From the International Searching Authority Re.: Application No. PCT/IL05/00138.
Written Opinion Dated Aug. 24, 2005 From the International Searching Authority Re.: Application No. PCT/IL2005/000442.
Written Opinion Dated Nov. 28, 2005 From the International Searching Authority Re.: Application No. PCT/IL05/00141.
Proceeding Further With the European Patent Application Pursuant to Rule 70(2) EPC Dated Jul. 31, 2009 From the European Patent Office Re.: Application No. 06704564.1.
Translation of Notification of Reasons of Rejection Dated Mar. 9, 2010 From the Japanese Patent Office Re.: Application No. 2006-552008.
Translation of Notification of Reasons for Rejection Dated Dec. 15, 2010 From the Japanese Patent Office Re. Application No. 2009-027772.
Official Action Dated Mar. 15, 2011 From the US Patent and Trademark Office Re. U.S. Appl. No. 10/597,602.
Official Action Dated Mar. 16, 2011 From the US Patent and Trademark Office Re.: U.S. Appl. No. 11/568,463.
Proceeding Further With the European Patent Application Pursuant to Rule 70(2) EPC Dated Jul. 31, 2009 From the European Patent Office Re.: Application No. 06704564.1.
Translation of Notification of Reasons of Rejection Dated Mar. 9, 2010 From the Japanese Patent Office Re.: Application No. 2006-552008.
Response Dated Feb. 22, 2011 to Official Copy of Decision of Rejection of Oct. 29, 2010 From the Japanese Patent Office Re. Application No. 2007-529131.
Translation of Notification of Reason for Rejection Dated Apr. 7, 2011 From the Japanese Patent Office Re. Application No. 2006-552014.
Translation of Notification of Reasons for Rejection Dated Apr. 6, 2011 From the Japanese Patent Office Re. Application No. 2006-215045.
Response Dated Apr. 6, 2011 to Notification of Reasons for Rejection of Jan. 27, 2011 From the Japanese Patent Office Re. Application No. 2007-510233.
Response Dated Apr. 10, 2011 to Notification of Reasons for Rejection of Dec. 15, 2010 From the Japanese Patent Office Re. Application No. 2009-027772.

* cited by examiner

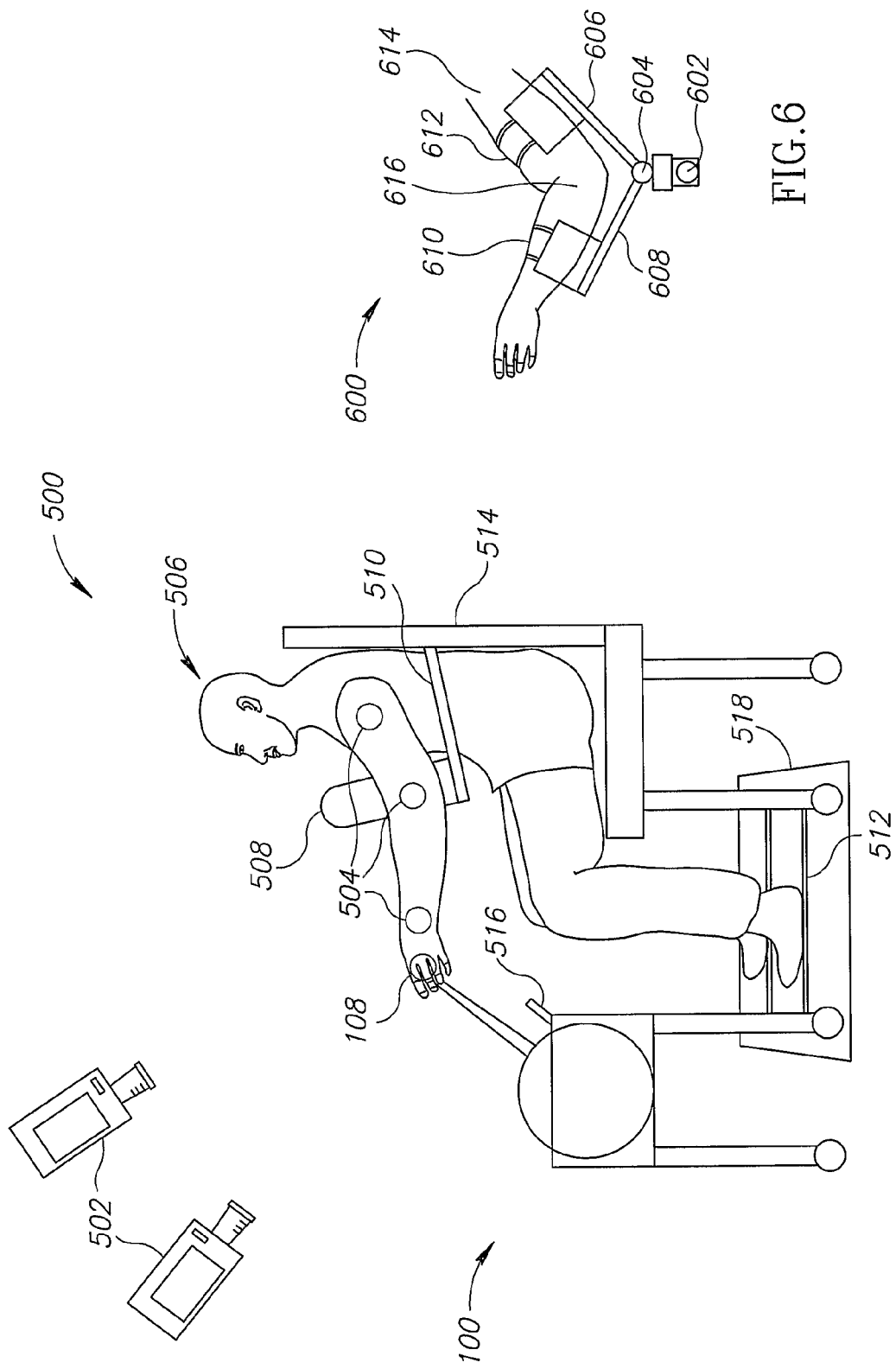

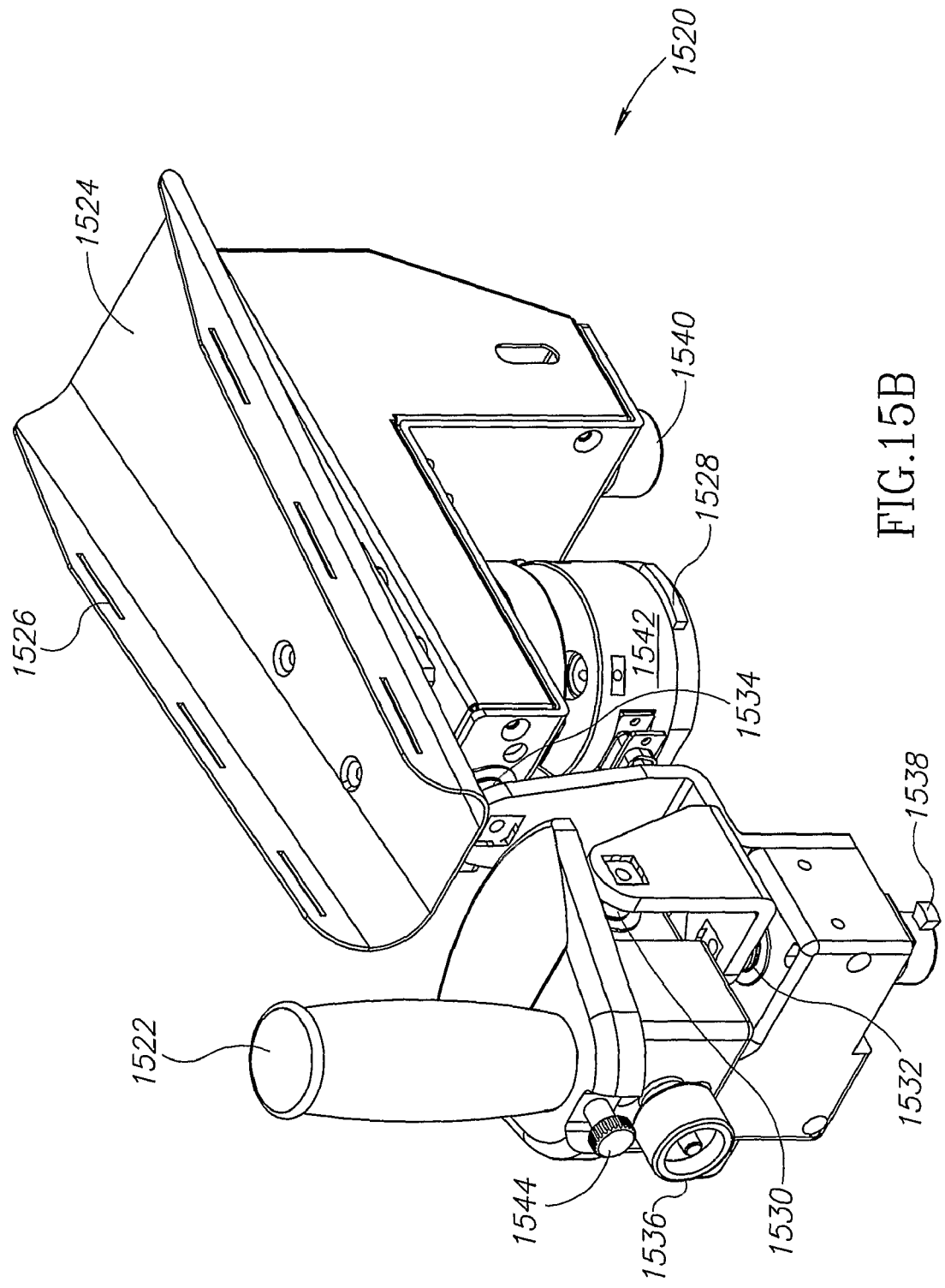

METHODS AND APPARATUS FOR REHABILITATION AND TRAINING

RELATED APPLICATIONS

The present application is a U.S. National Phase of PCT Application No. PCT/IL2005/000141, filed on Feb. 4, 2005.

This application also claims the benefit under 119(e) of U.S. Provisional Application No. 60/542,022 filed on Feb. 5, 2004, U.S. Provisional Application No. 60/566,078 filed on Apr. 29, 2004, U.S. Provisional Application No. 60/566,079 filed on Apr. 29, 2004, U.S. Provisional Application No. 60/604,615 filed on Aug. 25, 2004, U.S. Provisional Application No. 60/633,428 filed on Dec. 7, 2004, U.S. Provisional Application No. 60/633,429 filed on Dec. 7, 2004 and U.S. Provisional Application No. 60/633,442 filed on Dec. 7, 2004 the disclosures of which are incorporated herein by reference.

This application is also related to PCT applications, PCT/IL2005/000138 entitled "Gait Rehabilitation Methods and Apparatuses"; PCT/IL2005/000137 entitled "Rehabilitation with Music"; PCT/IL2005/000135 entitled "Neuromuscular Stimulation"; PCT/IL2005/000139 entitled "Fine Motor Control Rehabilitation"; PCT/IL2005/000140 entitled "Methods and Apparatuses for Rehabilitation Exercise and Training"; and PCT/IL2005/000142 entitled "Methods and Apparatus for Rehabilitation and Training"; all filed on Feb. 4, 2005. The disclosures of all these applications are incorporated herein by reference.

FIELD OF THE INVENTION

The present invention relates to manipulation of a body, for example for physical rehabilitation and/or training.

BACKGROUND OF THE INVENTION

After accidents or strokes, persons often need a prolonged rehabilitation process in an attempt to recapture some or all of the body function damaged in the accident or stroke. Such rehabilitation may include one or both of two elements, a physical rehabilitation portion, in which damaged or unused muscles, nerves and/or joints are brought back to full functioning (to the extent possible) and a cognitive rehabilitation portion, in which the cognitive ability to control the body is restored. In some cases, the damage to the body and/or brain is such that a patient needs to be trained in modified functionality (e.g., when one limb is made short) or even new functionality, for example, in the use of an artificial limb.

Physical therapy is currently provided mainly by personal attention of a physical therapist who monitors and instructs a patient in the performance of certain exercises. Thus, costs for rehabilitation are high and compliance after a patient leaves a treatment center is relatively low.

Some home physical therapy devices are known, for example a product called "backlife" provides CPM (Continuous Passive Motion) of the spine.

U.S. Pat. No. 5,836,304, the disclosure of which is incorporated herein by reference, describes a cognitive rehabilitation utilizing a remote therapist.

U.S. Pat. No. 5,466,213, the disclosure of which is incorporated herein by reference, describes a rehabilitation system using a robotic arm.

An article in Journal of Rehabilitation Research and Development, Vol. 37 No. 6, November/December 2000, titled "Development of robots for rehabilitation therapy: The Palo Alto VA/Stanford experience", by Charles G. Burgar, M D; Peter S. Lum, PhD; Peggy C. Shor, OTR; H. F. Machiel Van der Loos, PhD, the disclosure of which is incorporated herein by reference, describes usage of robots for rehabilitation.

SUMMARY OF THE INVENTION

A broad aspect of some embodiments of the invention relates to rehabilitation methods and apparatus suitable for a wide range of situations, including, temporal, mental, cognitive, motor, location and/or other situations.

An aspect of some embodiments of the invention relates to a rehabilitation device which guides a patient to perform a motion with a correct spatial trajectory, by the device applying one or more pushing, assisting, reminding, responding and/or resisting forces during a motion (or intent to move) by the patient. In an exemplary embodiment of the invention, the forces are applied by an actuator, for example, a robotic articulated arm or a spherically jointed lever. In some embodiments, the applied forces act as a force field, optionally continuous, which impedes and/or guides a patient. Alternatively or additionally to spatial trajectories, orientation trajectories and/or speed trajectories are guided, supported and/or measured.

In an exemplary embodiment of the invention, the device supports, for a given volume of space and a range of force strengths, substantially any 3D trajectory within that volume. In an exemplary embodiment of the invention, a device is provided which supports the range of motion of a healthy arm or leg in one, two or three dimensions. In some cases, a partial volume is sufficient, for example, 50% or 30% of such a volume.

Optionally, the device is programmable with various trajectories (paths and/or velocities) and/or forces. Optionally, the forces at one point in the trajectory can vary responsive to an actual trajectory by the patient, possibly a same trajectory (e.g., at an earlier point thereof) and/or responsive to a rehabilitation plan and/or improvement of the patient. Optionally, the device learns the patient motion and repeats it with a correction (e.g. a smoothing of trajectory and or speed). Alternatively or additionally, the device can learn a motion entered by a physiotherapist and replay it for the patient, with an optional adjustment (e.g. a limb size adjustment).

In an exemplary embodiment of the invention, the trajectories and/or forces are defined for one or more points on the body, on same and/or different limb or body part. Optionally, a point is controlled (and/or measured) with 3, 4, 5 or 6 degrees of freedom.

In an exemplary embodiment of the invention, the programming comprises programming an electronic controller. In an exemplary embodiment of the invention, the programming comprises mechanical programming.

An aspect of some embodiments of the invention relates to a rehabilitation device adapted for home use. In an exemplary embodiment of the invention, the device is portable in a home, for example, not permanently attached to any surface and/or including wheels. In an exemplary embodiment of the invention, the device is collapsible on a regular basis. In an exemplary embodiment of the invention, the device is light enough to avoid structural overloading of residential floors, for example the device can weigh less than 100 kg, less than 50 Kg or less than 25 Kg. Optionally, the device can be folded down to fit in a trunk of a standard sedan-type car, for example having a maximum dimension of less than 120 cm. Optionally, the device breaks down into parts which are light enough to be carried by a non-handicapped person.

In an exemplary embodiment of the invention, the device ensures that a patient is correctly positioned. Optionally, the patient is notified to correct his position. In an alternative embodiment of the invention, the device recalibrates itself to take the patient position into account.

In an exemplary embodiment of the invention, a device is usable (e.g., by programming, attachments and/or setting) for a plurality of different treatments, for example, a plurality of different body sizes, a plurality of different ages, a plurality of different joints and/or a plurality of different appendages.

In an exemplary embodiment of the invention, a rehabilitation device is provided which is portable for various activities, for example, indoors and/or outdoors, such as, cooking, barbequing and eating at a table.

An aspect of some embodiments of the invention relates to rehabilitation of daily activities, for example, eating, pouring tea, knocking nails and cooking. In an exemplary embodiment of the invention, a kit including position sensors and/or other sensors is provided to attach to daily objects and track their use and provide feedback and/or instructions for rehabilitation. Optionally, such feedback and/or guidance are provided mechanically by a rehabilitation robot. In an exemplary embodiment of the invention, a daily activities training pedestal includes one or more adjustable work spaces on which daily activities is carried out, for example one surface emulating a table and another emulating a saucer (e.g., for training of tea pouring.

An aspect of some embodiments of the invention relates to long term rehabilitation and/or training. In an exemplary embodiment of the invention, a rehabilitation device is used for a long period of time, for example, months or years. Optionally, a same device is used both for rehabilitation and for training of a patient in correct motions. In an exemplary embodiment of the invention, a rehabilitation device is used for preventive training, for example, ensuring that a patient with developing arthritis does not start favoring a diseased joint. Optionally, a rehabilitation device is used to achieve a specific rehabilitation goal, such as rehabilitation of a particular limb. Optionally, the device is used for non-medical training, for example as a universal gym machine.

An aspect of some embodiments of the invention relates to support and/or measurement of various mental states of a patient, for example, motivation, depression, endurance, ability to train in pain, ability and/or desire to communicate and/or work and/or interact with others. These states often overlap. For example, depression, is often expressed as lack of motivation. In an exemplary embodiment of the invention, motivation is estimated by comparing performance in diagnosis, game and/or therapy situations. Such comparing optionally includes analyzing if a person achieved a same performance under different motivational states and/or how often did the person strain his limits. In an exemplary embodiment of the invention, the motivational state is used for one or more of estimating progress, suggesting psychological treatment, controlling difficulty of exercise and/or providing motivational incentives automatically.

An aspect of some embodiments of the invention relates to support and/or overcoming of cognitive problems while performing physical rehabilitation. In an exemplary embodiment of the invention, cognitive and/or perceptive limitations are overcome by providing one or more of instructions, feedback and guidance in a plurality of modalities, in less damaged modalities (e.g., selecting from various possibilities), and/or with a degree of enhancement congruent with the limitation (e.g., larger letters for weak eyesight). In an exemplary embodiment of the invention, the degree of enhancement is changed over time, as part of a rehabilitation of the limited function.

An aspect of some embodiments of the invention relates to multi-modal rehabilitation. In an exemplary embodiment of the invention, multiple body systems (e.g., motor, visual, auditory, visual-motor), skills and/or senses are rehabilitated using a same system, for example, motor control, motor propreception, visual perception and sound generation. In an exemplary embodiment of the invention, coordination between such systems is trained. In one example, hand-eye coordination is rehabilitated. In another example, hand-leg coordination is rehabilitated. In an exemplary embodiment of the invention, paths of coordination which are damaged are targeted for rehabilitation.

An aspect of some embodiments of the invention relates to feedback for rehabilitation. In an exemplary embodiment of the invention, the feedback includes feedback on carrying out of daily activities. Alternatively or additionally, the feedback includes feedback from a remote therapist or automatic feedback, during an activity. Alternatively or additionally, the feedback includes on a quality of the motion carried out by the patient.

An aspect of some embodiments of the invention relates to rehabilitation treatment methods. In an exemplary embodiment of the invention, training specifically in daily activities is carried out with the assistance of a rehabilitation device. Alternatively or additionally, training to prevent deterioration is provided, for example, to prevent deterioration of Parkinson's disease caused by neglecting of arm/function. Alternatively or additionally, training to provide long term improvement is carried out, for example, to provide improvement in cerebral palsy. Alternatively or additionally, treatment to prevent disease is carried out, for example, training a patient to not neglect a joint just because it hurts.

An aspect of some embodiments of the invention relates to using a rehabilitation device for both rehabilitation and testing, diagnosing and/or monitoring. In an exemplary embodiment of the invention, the device is used to assess the abilities of a patient and then to rehabilitate that patient. Alternatively or additionally, the device is used to measure the patient and calibrate future rehabilitation to those measurements. Exemplary measurements include size, strength, range of motion and motion quality, mental state and/or cognitive and/or perceptive abilities.

An aspect of some embodiments of the invention relates to a rehabilitation method related to motion quality. In an exemplary embodiment of the invention, a quality of a motion is defined. Optionally, when a patient is being rehabilitated, automated feedback is provided to the patient regarding the quality of his motion. Alternatively or additionally, part of rehabilitation and/or training is teaching a patient the quality value for various motions.

An aspect of some embodiments of the invention relates to correctness of motion. In an exemplary embodiment of the invention, a rehabilitation device is programmed with a correct movement. In an exemplary embodiment of the invention, a correct motion is programmed into the device by performing the correct motion and then storing the motion in a device-associated memory. Optionally, the motion is programmed in during a dedicated teaching mode or when the device is off-line. Alternatively, the device learns during usage by a patient.

Optionally, the device is used to teach a patient what correct motion is, for example using template and/or using rules (e.g., a ⅔ power rule for motor control). In an exemplary embodiment of the invention, correctness of motion is evaluated as a parameter of rehabilitation and feedback is provided thereon.

An aspect of some embodiments of the invention relates to a rehabilitation device for daily activities, in which the rehabilitation device is configured to train and/or test patients in the carrying out of daily activities. In an exemplary embodiment of the invention, the rehabilitation device can be used in proximity to real-life settings, such as a table or a counter.

An aspect of some embodiments of the invention relates to positioning of a rehabilitation device including a motion mechanism. In an exemplary embodiment of the invention, a motion mechanism has a limited range of motion and/or accuracy. The rehabilitation device is optionally positioned to make maximum usage of this range of motion, e.g., by matching to a specific exercise. In an exemplary embodiment of the invention, the rehabilitation device includes a positioning element, for example a rail and/or one or more joints that can be used to fix the motion mechanism at a desired position and/or orientation. Optionally, the positioning element is motorized, for example, to allow automatic or non-manual motion of the motion mechanism.

An aspect of some embodiments of the invention relates to a rehabilitation method in which a healthy body part is used for rehabilitating a diseased body part. In an exemplary embodiment of the invention, a rehabilitation device allows simultaneous or parallel motion of two limbs, one damaged and one not, and uses the correct motion of an undamaged limb as a basis for force field definition for the damaged limb. Alternatively or additionally, sequential motion by undamaged and then damaged limbs is provided. Optionally, the undamaged motion is modified, for example reduced in force, speed or range of motion. Optionally, the motion is mirror motion or synchronized motion (e.g., arm and leg during swimming). In an exemplary embodiment of the invention, a device which can hold two limbs is used. In some embodiments the motion of the two limbs is linked. In other embodiments, there is some or complete de-coupling between the limbs, at least in real time.

An aspect of some embodiments of the invention relates to a multi-point rehabilitation device in which the rehabilitation device is attached to a human body at multiple points which can move relative to each other, which motion is part of rehabilitation.

In an exemplary embodiment of the invention, the rehabilitation device attaches to two limbs, for example an arm and a leg or two arms.

In an exemplary embodiment of the invention, the rehabilitation device separately allows motion in 3D space of two bones on either side of a joint.

In an exemplary embodiment of the invention, the device mechanically limits motion for one or more of the points. Optionally, one or more of the points are tracked (in one or more dimensions) but their motion is not mechanically limited in some or any directions.

In an exemplary embodiment of the invention, the rehabilitation device supports complex motion in which different parts of the body are called upon to carry out certain motions, for example, shoulder motion and wrist motion.

An aspect of some embodiments of the invention relates to a mechanical structure for a rehabilitation device. In an exemplary embodiment of the invention, the device comprises an arm mounted on a joint, with a body attachment point, for attachment to or holding by a patient, mounted on the arm. The joint acts as a spherical joint, allowing movement of the arm along substantially any path on the surface of a sphere, within a range of angles, for example, ±90 degrees relative to the center of the joint, in either of phi and theta directions (e.g., in spherical coordinates). Optionally, the center of rotation for such motions is substantially a same center of rotation for all the paths. In an exemplary embodiment of the invention, the joint and/or the arm as a whole lack singularity points in the range of motion. Optionally, the resistance to motion of the joint (the device may add resistance) is substantially uniform, substantially independently of the spherical motion.

In an exemplary embodiment of the invention, the spherical joint comprises a ball in socket joint, with the arm attached to the ball or to the socket. The other one of the ball or socket is optionally attached to a base, for example, a base which stands on a floor or is attached to a wall or a ceiling.

In an exemplary embodiment of the invention, balancing is provided. In one example, the device includes a weight attached to said ball opposite of said arm and serving to balance the motion of said arm. Optionally, the motion of the arm is substantially balanced over the entire range of motion thereof. In an exemplary embodiment of the invention, the balancing includes prevention of a resting torque. Alternatively or additionally, balancing includes correction for an existing moment of inertia or an expected moment of inertia during use. Optionally, the device is configured to include a resting force which tends to stabilize or destabilize the device, depending on the embodiment.

Optionally, one or more guiding plates are provided. In an exemplary embodiment of the invention, a pin attached to the ball, optionally part of the weight, is constrained to travel within a slot (e.g., a rectangle or other shape) defined in a guide plate. Optionally, the slot is elastic.

Optionally, one or more motors are provided to rotate the ball and/or apply force in a desired direction.

Optionally, one or more directional brakes are provided to selectively stop motion of the ball in a desired direction.

Optionally, one or more unidirectional brakes are provided to selectively stop motion of the ball in any direction.

In an alternatively embodiment of the invention, two or more joints having a shared center of rotation, are provided instead of a ball, for example a universal joint.

In an exemplary embodiment of the invention, the arm is extendible along its axis. Optionally, a motor is provided for selectively moving or apply force to resist motion of the extension along the axis. Optionally, one or more brakes are provided to selectively resist motion of said extension along said axis.

In an exemplary embodiment of the invention, the extension is balanced, so that it has no self motion. Alternatively or additionally, the extension, even when extended to various extents does not affect a balance of said arm.

Optionally, a rehabilitation device is positionable at various orientations. Optionally, the device includes a joint between its base and an articulating portion thereof.

An aspect of some embodiments of the invention relates to a ball joint with selective locking. In an exemplary embodiment of the invention, a chuck is provided to selectively lock rotation of the ball joint. Optionally, a plurality of directional brakes are provided. Optionally, one or more sensors generates an indication of a direction of force application and a controller selects which directional and/or uni-directional brakes to release responsive to the force direction.

An aspect of some embodiments of the invention relates to a telescoping element, optionally used as part of a rehabilitation device. In an exemplary embodiment of the invention, at least three portions are provided, two ends and a center, with extension or retraction forces being applied to the central portion. The central portion is attached to the two end portions using a rack and pinion (one rack on each end portion and the two pinions at either end of the central portion. A belt interconnects the two pinions so that they move in concert.

An aspect of some embodiments of the invention relates to a force-feedback control mechanism including a spring. Changes in compliance are provided by changing an effective length of the spring. In an exemplary embodiment of the invention, the spring is a flat spiral spring and the compliance is in a direction perpendicular to the plane of the spring.

An aspect of some embodiments of the invention relates to a force control mechanism for a human-movable element. In an exemplary embodiment of the invention, a spring is provided to counteract force applied by a human. Optionally, the degree of force is adjustable, optionally by preloading the spring (or other resilient element). Optionally, the human movable element is also moved by a motor and said compliance is optionally provided to said human motion. Optionally a damping element, for example viscous cushioning, is provided.

In an exemplary embodiment of the invention, the resilient element is configurable, optionally on the fly, to provide a desired degree of resistance to the movement. Optionally, the resilient means is re-adjusted to follow actual motion of the element.

In an exemplary embodiment of the invention, the motor moves the handle using one joint and a second joint is used for the force compliance.

In an exemplary embodiment of the invention, the force compliance is provided by one resilient element to a plurality of axes simultaneously, substantially without coupling between the axes.

In an exemplary embodiment of the invention, movement of the element in spherical rotation axially compresses a resilient element which then provides compliance.

In an exemplary embodiment of the invention, power is provided to the element using a gear system which cannot be back-driven. When back-driving is detected, it is mechanically shunted to a resilient element, which provides compliance.

In an exemplary embodiment of the invention, a mechanical diode design is provided in which a motion is imparted to a lever using a gear and in which the lever cannot move the gear. In an exemplary embodiment of the invention, the diode comprises a gear or lever engaging a worm gear with a low enough lead angle (i.e., not back driven) a motor turns the worm gear, thereby moving the gear and/or a lever attached thereto. Due to the low lead angle, when the gear rotates, the worm gear moves axially rather than rotates. Optionally, the worm gear sits on springs or another elastic element which provide a degree of resiliency to motion of the gear. Optionally, the springs are pre-stressed to a desired amount. Optionally, the worm gear is rotated to follow motion of the lever and maintain a desired tension and/or symmetry in the elastic element(s).

An aspect of some embodiments of the invention relates to a manual manipulator which moves or controls movement of a human body using at least one wire and optionally one or more robotic elements, so that motion in 3D of at least one point of the body is constrained by the manipulator. In an exemplary embodiment of the invention, the manipulator is configured for use as a rehabilitation device. Optionally, one or more motors are provided to move the at least one point. Optionally, one or more resilient elements are provided to allow some slack with resiliency to be provided in one or more wires. Optionally, three wires are provided to constrain 3D motion.

An aspect of some embodiments of the invention relates to patient positioning in a rehabilitation system. In an exemplary embodiment of the invention, the system determines patient position using an imaging system. In an exemplary embodiment of the invention, alternatively or additionally, a location of a chair or other support for the patient, relative to the system, is determined. Optionally, a spring-loaded wire system is used to measure the relative positions. Optionally, a pressure sensitive mat is used.

In an exemplary embodiment of the invention, the patient is instructed to perform one or more motions and the relative positions are determined from the trajectories of the motions. Optionally, position is determined in 2D, rather than in 3D. Alternatively, 3D position and/or orientation information is determined.

In an exemplary embodiment of the invention, a moving part of the system itself or a light pointer portion of the system are used to mark and/or note a correct positioning.

In an exemplary embodiment of the invention, once the relative position is determined, one or more exercises are modified to take into account the relative positions.

An aspect of some embodiments of the invention relates to safety of a rehabilitation device. In an exemplary embodiment of the invention, the rehabilitation device includes one or more mechanical fuses which selectively tear when shear, strain and/or torque on a replaceable element (such as a pin) increase above a threshold. Alternatively to a mechanical pin, an adjustable magnetic pin may be used, in which two parts of a pin attach to each other based on magnetic attraction. The attraction level is optionally set by moving a magnet inside one of the parts of the pin. Torque is optionally detected by providing a serrated connection between the pin parts which links relative rotation of the pin parts and separation of the parts. Optionally, a wire is provided in the pin so that tearing of the wire can be detected by the device electrically.

In an exemplary embodiment of the invention, a dead-man switch is provided for a patient in which if a patient lets go of the switch, the device stops or goes into a predefined or dynamically determined safe mode and/or position. Optionally, the dead-man switch is on a wireless element held by a good limb or body part, for example, being stepped on, held by hand or held in a mouth.

In an exemplary embodiment of the invention, a voice activated shut-off is provided, for example to allow a patient to stop the rehabilitation by shouting.

In an exemplary embodiment of the invention, the rehabilitation device analyses motions and/or forces applied by the patient, to detect problems. For example, any gross irregularities will cause the rehabilitation device to stop.

In an exemplary embodiment of the invention, the device includes at least one moving element which includes resiliency when moving so that there is slack, with increasing resistance as amount of slack used increases. Optionally, the slack serves to allow a user to not perform a motion according to the movement of the element, while providing sufficient time to detect that the motion is incorrect and that applied forces are reaching a safety limit.

Examples of types of situations where embodiments of the invention may be useful, follow. In some exemplary embodiments of the invention, a range of treatment lengths are supported, including for example, goal oriented treatment, short term treatment, long term treatment and/or preventive activities. In some exemplary embodiments of the invention, treatment over multiple stages in rehabilitation, possibly an entire rehabilitation process, are supported, in some cases with a same device. In some exemplary embodiments of the invention, multiple body parts may be rehabilitated, either simultaneously or separately, in some cases, with a same device. In some embodiments of the invention, multiple modalities are rehabilitated, either together or using a same device, for example, motor control, motor feedback, vision, audio ability and/or speech. A range of complexities and hierarchies of motion are supported by some embodiments, for example, simple motion of one joint and complex planning of multi-limb motion. Multiple treatment locations are supported by some embodiments of the invention, for example, ICU, bed, clinic, home and/or outdoor. Multiple activity types are supported in some embodiments of the invention, for example, dedicated rehabilitation exercises, training exercises, daily activities, outdoor activities and/or diagnosis activities. In some embodiments of the invention, multiple body positions are supported, for example, lying down, standing and/or sitting. In some embodiments of the invention, a range of mental, cognitive and/or motor ability states are supported. It should be noted that not all the embodiments of the invention support all the various ranges and the extents of the ranges described above.

There is thus provided in accordance with an exemplary embodiment of the invention a method of rehabilitation using an actuator type that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume, comprising:

exercising a patient at a first place of rehabilitation selected from a bed, a wheel-chair, a clinic and a home, using an actuator of said actuator type which interacts with a motion of said patient; and second exercising said patient at a second place of rehabilitation selected from a bed, a wheel-chair, a clinic and a home using a second actuator of said actuator type which interacts with a motion of said patient;

wherein said first exercising and said second exercising utilize a same movement mechanism design for moving the actuators.

Optionally, said first and said second exercising are performed using a same rehabilitation apparatus.

In an exemplary embodiment of the invention, said motion mechanism is motorized. Optionally, said motion and said force are controlled by a controller. Alternatively or additionally, said motion mechanism is capable of applying a force of at least 10 Kg to a tip of said actuator. Alternatively or additionally, said motion mechanism is capable of applying a force of different magnitudes in different directions of motion said actuator.

In an exemplary embodiment of the invention, said motion mechanism is adapted to apply selective resistance to motion of said actuator.

In an exemplary embodiment of the invention, said actuator is adapted to interact with said motion in a plurality of modes including at least causing said motion, guiding said motion and recoding said motion. Optionally, said first and said second exercising use different motion interaction modes.

In an exemplary embodiment of the invention, at least one of said first and said second exercising are performed in water.

In an exemplary embodiment of the invention, said first and said second exercising are performed on a same limb.

In an exemplary embodiment of the invention, said first and said second exercising are different exercises.

In an exemplary embodiment of the invention, the method comprises keeping track of progress of said patient including said first and said second exercising, in a same controller coupled with said second actuator.

Optionally, said actuator is rigid.

There is also provided in accordance with an exemplary embodiment of the invention a method of rehabilitation using an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume, comprising:

exercising a first organ type of a patient using said actuator; and exercising a second organ type of the patient using said actuator.

In an exemplary embodiment of the invention, the method comprises replacing an attachment to said patient of said rehabilitation device between said exercising.

In an exemplary embodiment of the invention, the actuator comprises a controller which controls said interaction. Optionally, said controller is programmed with a plurality of different exercises for different limbs In an exemplary embodiment of the invention, the method comprises adjusting at least one of a spatial position and orientation of said actuator relative to said patient, between said exercises.

There is also provided in accordance with an exemplary embodiment of the invention a rehabilitation kit, comprising:

an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

a tip on said actuator; and a plurality of attachments modularly exchangeable for said tip, at least two of which are adapted to fit different organs.

Optionally, at least one of said attachments is powered via said actuator. Alternatively or additionally, at least one of said attachments is capable of rotation in three axes of rotations.

There is also provided in accordance with an exemplary embodiment of the invention a device for rehabilitation, comprising:

a motorized actuator adapted to support a movement by a person by at least one of resisting motion, guiding motion and causing motion; and a controller configured to control said actuator, wherein, said controller is programmed to provide rehabilitation exercising for patient's switchable between a plurality of modes in which one or more or motivation, cognitive ability and motor ability is either high or low.

Optionally, said controller is configured to provide instructions in a selectable one of at least three information presentation modes and complexity levels.

Alternatively or additionally, said controller is configured to provide support for motor activity of said patient in a selectable one of at least three levels of assistance.

Alternatively or additionally, said controller is configured to provide incentive feedback to said patient in a selectable one of at least three levels of incentive.

There is also provided in accordance with an exemplary embodiment of the invention a method of rehabilitation using an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume, comprising:

coupling said actuator to a person in a home setting;

performing a daily activity by said person, wherein said actuator interacts with said activity to enhance rehabilitation.

Optionally, said daily activity is outdoors

Alternatively or additionally, said actuator interacts using a stored rehabilitation plan.

Alternatively or additionally, said actuator reports to a remote location on a progress of rehabilitation.

Alternatively or additionally, said actuator prevents unsafe motions by said patient.

Alternatively or additionally, the method comprises first practicing said daily activity at a rehabilitation clinic.

There is also provided in accordance with an exemplary embodiment of the invention a method of rehabilitation, comprising:

rehabilitating a first patient on a first rehabilitation device;

rehabilitating a second patient on a second rehabilitation device; and passing information regarding rehabilitation between said two devices, said information including at least one of a score, current progress, spatial position of a portion of the patient and a game play.

Optionally, said patients play a game together using said devices for input and output. Optionally, said patients play against each other. Alternatively or additionally, said first rehabilitation device provides a different support fro said first patient than said second device supplies for said second patient, to compensate for differences in ability between the two patients.

In an exemplary embodiment of the invention, said information is passed in real-time.

In an exemplary embodiment of the invention, said information is passed using a wireless connection.

In an exemplary embodiment of the invention, the method comprises monitoring said first and said second patients by a remote therapist.

In an exemplary embodiment of the invention, the method comprises remotely connecting into a therapy group by said patients.

In an exemplary embodiment of the invention, said two devices are in a same room.

There is also provided in accordance with an exemplary embodiment of the invention a rehabilitation system configuration, comprising:

A first rehabilitation device; and

A second rehabilitation device linked by a wireless data link with said first rehabilitation device such that the two rehabilitation devices can act in synchrony.

There is also provided in accordance with an exemplary embodiment of the invention a method of cooperative rehabilitation, comprising:

providing a first actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

providing a second actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

engaging said first and said second actuators by a patient and by a non-therapist, respectively; and rehabilitating said patient using said first actuator and said non-therapist.

Optionally, said non-therapist is a blood relative.

In an exemplary embodiment of the invention, the method comprises guiding said non-therapist and said patient by instructions by a controller.

In an exemplary embodiment of the invention, said non-therapist is under an age of 18.

In an exemplary embodiment of the invention, said non-therapist is under an age of 10.

In an exemplary embodiment of the invention, said providing is at a home of said non-therapist.

In an exemplary embodiment of the invention, said non-therapist has fewer than 50 hours experience in physical therapy.

In an exemplary embodiment of the invention, said non-therapist has fewer than 10 hours experience in physical therapy.

There is also provided in accordance with an exemplary embodiment of the invention a rehabilitation device comprising:

a frame;

an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

a joint interconnecting said frame and said actuator and allowing multiple different relative placements of said movement mechanism on said frame, such that said volume moves relative to said frame.

Optionally, said motion mechanism has different motion limitations in different spatial direction and wherein said multiple relative placements include changing an orientation of said mechanism.

In an exemplary embodiment of the invention, said joint comprises a linear joint.

In an exemplary embodiment of the invention, said joint comprises a swiveling joint.

In an exemplary embodiment of the invention, said frame is curved.

In an exemplary embodiment of the invention, said joint is motorized.

In an exemplary embodiment of the invention, the device comprises a controller that controls said joint according to an exercise stored in said controller to be performed.

In an exemplary embodiment of the invention, the device comprises at least one sensor that reports a position of said joint.

There is also provided in accordance with an exemplary embodiment of the invention a method of setting up a rehabilitation system including an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume, comprising:

determining a rehabilitation exercise to be performed;

selecting a desired position for said motion control mechanism for said exercise; and adjusting a position of the mechanism on a frame according to said desired position.

In an exemplary embodiment of the invention, the method comprises automatically adjusting said position.

In an exemplary embodiment of the invention, the method comprises automatically reporting to a user said desired position.

There is also provided in accordance with an exemplary embodiment of the invention a rehabilitation device, comprising:

a joint having freedom of motion in Phi (rotation) and Theta (elevation) spherical angles, said freedom allowing positioning of said joint in substantially any angular position within a range of at least 30 degrees in each angular direction.

a substantially rigid radial extension attached to said joint and adapted for movement with a limb of a person at at least one point thereof; and a controller adapted to control motion of said joint and thereby motion of said radial extension.

In an exemplary embodiment of the invention, said radial extension is balanced such that said point remains stable if no force is applied and moves if force is applied by said person. Optionally, said balancing can be varied to match a weight of an attachment selectively attached to said extension. Alternatively or additionally, said balancing can be varied by said controller along a path of motion to match a change in moment on said point. Alternatively or additionally, said balancing can be set to provide a neutral buoyancy to said limb.

In an exemplary embodiment of the invention, said joint is a ball joint.

In an exemplary embodiment of the invention, said joint comprises two orthogonal hinges with a common center of rotation.

In an exemplary embodiment of the invention, said controller comprises a mechanical controller.

In an exemplary embodiment of the invention, said controller comprises an electrical controller.

In an exemplary embodiment of the invention, the device comprises at least one brake adapted to selectively resist said freedom motion. Optionally, said brake is continuously controlled by said controller. Alternatively or additionally, said brake is uni-directional in only one of said Phi and Theta directions. Alternatively or additionally, said brake is operative in both said Phi and said Theta directions.

In an exemplary embodiment of the invention, the device comprises at least one motor adapted to move said joint. Optionally, said motor is adapted to apply at least 10 Kg of force at said point. Alternatively or additionally, said motor is continuously controlled by said controller. Alternatively or additionally, said motor cannot be back-driven by said extension.

In an exemplary embodiment of the invention, the device comprises at least one resilient element adapted to provide resilient compliance when said person moves said point in a trajectory other than a trajectory for which motion is controlled to move by said controller. Optionally, said controller sets a degree of said resilient compliance.

In an exemplary embodiment of the invention, said element is extendible.

In an exemplary embodiment of the invention, element includes a conduit for electrical power.

In an exemplary embodiment of the invention, the device comprises at least one position sensor which reports on a angular position of said joint.

In an exemplary embodiment of the invention, the device comprises at least one force sensor which reports on a force applied to said joint.

In an exemplary embodiment of the invention, said controller is configured to control said motion and provide at least one of assisting motion by said patient limb, resisting motion by said patient limb, guiding motion by said patient limb, nudging said patient limb to move and moving said patient limb.

In an exemplary embodiment of the invention, said controllers stores thereon a plurality of different rehabilitation exercises.

There is also provided in accordance with an exemplary embodiment of the invention a balanced rehabilitation device, comprising an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume; and at least one weight that balances said actuator such that no force is required to maintain said actuator in space.

There is also provided in accordance with an exemplary embodiment of the invention a method of rehabilitation, comprising:

assisting motion in space of a patient along a trajectory, using an actuator;

providing resistance to motion by said patient away from said trajectory, said resistance including compliance in a direction away from said trajectory, wherein said compliance is achieved mechanically without an electro-mechanical feedback loop.

In an exemplary embodiment of the invention, said compliance is provided by braking.

In an exemplary embodiment of the invention, said compliance is provided by at least one resilient element.

In an exemplary embodiment of the invention, the method comprises tracking said motion of the patient with said compliance.

In an exemplary embodiment of the invention, a different force of resistance is provided at different points in space along the motion.

In an exemplary embodiment of the invention, a different force of resistance is provided at different direction at a same point in space.

In an exemplary embodiment of the invention, said compliance is at least 1 cm.

There is also provided in accordance with an exemplary embodiment of the invention a rehabilitation device comprising:

a lever adapted to move together with a portion of a patient's body;

a motor, operatively connected to said lever in a manner which prevents back-driving of the motor by said lever, said motor being operative to move the lever; and a spring coupled to said lever and providing resilience to said motion.

In an exemplary embodiment of the invention, said spring provides said resilience only when said lever is moved different from motion caused by the motor.

In an exemplary embodiment of the invention, attempted back-driving of said motor applies force to said spring.

In an exemplary embodiment of the invention, said spring has a controllable pre-load.

In an exemplary embodiment of the invention, the device comprises a damping element in parallel with said spring.

There is also provided in accordance with an exemplary embodiment of the invention a rehabilitation device comprising:

a lever adapted to move together with a portion of a patient's body;

a motor, operatively connected to said lever to move the lever;

a slot guiding motion of said lever; and a spring coupled to said lever and providing resilience to said motion.

In an exemplary embodiment of the invention, said spring is mounted on said slot.

There is also provided in accordance with an exemplary embodiment of the invention a multi-axis resilient element for rehabilitation, comprising:

a first set of at least one joint adapted to allow motion in spherical coordinates of a radially extending lever;

a second set of at least one joint adapted to allow motion in spherical coordinates of said first set;

a resilient element having a compression associated with motion of said lever thereby compliance to motion in said second set.

In an exemplary embodiment of the invention, said resilient element has a settable pre-load.

There is also provided in accordance with an exemplary embodiment of the invention a rehabilitation device comprising:

a lever adapted to move together with a portion of a patient's body;

a motor, operatively connected to said lever to move the lever; and a spring coupled to said lever and providing resilience to said motion, wherein said spring has a settable compliance.

In an exemplary embodiment of the invention, said compliance is set by a controller. Optionally, said setting is continuous.

In an exemplary embodiment of the invention, said spring is a flat spring having a settable effective length.

There is also provided in accordance with an exemplary embodiment of the invention a telescoping mechanism comprising:

at least three telescoping sections, including a central section and two end sections;

an actuating mechanism that extends said central section;

a first rack and pinion mechanism that couples motion of one of said ends and of said central portion;

a second rack and pinion mechanism that couples motion of the other one of said ends and of said central portion; and a belt operatively linking the two rack and pinion mechanisms.

There is also provided in accordance with an exemplary embodiment of the invention a portable rehabilitation device comprising:

a base for stabilization of the device to a surface or object; and an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume, wherein said device has two configurations:

a first configuration suitable for practicing rehabilitation; and a second configuration suitable for storage, and wherein said device is adapted to pass between said configurations manually, by a layman.

In an exemplary embodiment of the invention, said device is taken apart for said second configuration.

In an exemplary embodiment of the invention, said device comprises at least one quick-connection.

In an exemplary embodiment of the invention, said device folds down.

In an exemplary embodiment of the invention, said device folds flat to fit in a car trunk.

In an exemplary embodiment of the invention, said device weighs less than 30 Kg.

In an exemplary embodiment of the invention, said device is wheeled

There is also provided in accordance with an exemplary embodiment of the invention a rehabilitation device, comprising:

a lever adapted to move together with a portion of a patient's body;

at least one motor coupled to said lever adapted to interact with a motion of said lever; and at least one separable element interconnecting said motor and said lever and adapted to decouple at least a portion of said lever from said motor is a predetermined force on the element is exceeded.

In an exemplary embodiment of the invention, said element comprises a tearing pin.

In an exemplary embodiment of the invention, said element comprises a separable joint.

In an exemplary embodiment of the invention, said element is connected between a body of said lever and an attachment mounted on said lever.

There is also provided in accordance with an exemplary embodiment of the invention a rehabilitation device, comprising:

a lever adapted to move together with a portion of a patient's body;

at least one motor coupled to said lever adapted to interact with a motion of said lever;

at least one resilient element interconnecting said motor and said portion; and a controller adapted to identify a safety problem and stop said motor upon said identifying, said resilient element preventing such stopping from being immediate.

In an exemplary embodiment of the invention, said device comprises an actuator that includes a movement mechanism capable of applying a force to said lever which lever interacts with a motion of a patient's limb in a volume of at least 30 cm in diameter, in at least three degrees of freedom of motion of the lever.

In an exemplary embodiment of the invention, said controller identifies said safety problem by detecting a shout by said patient.

In an exemplary embodiment of the invention, said controller identifies said safety problem by calculating at least one position of a point of the body of said patient and comparing the result of the calculation to one or more allowed value.

There is also provided in accordance with an exemplary embodiment of the invention a rehabilitation docking station comprising:

an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

at least one actuator adapted to assist in rehabilitation by; and a docking port adapted for locking to a patient carrier.

In an exemplary embodiment of the invention, said port is adapted to engage a wheelchair.

In an exemplary embodiment of the invention, said port is adapted to engage a bed.

In an exemplary embodiment of the invention, said station is mobile.

In an exemplary embodiment of the invention, said station includes at least one port for attachment of a second actuator thereto.

There is also provided in accordance with an exemplary embodiment of the invention a method of rehabilitation comprising:

providing an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

coupling said actuator to a point on a human body;

applying a force vector to said point by said actuator, said force including a rotation.

In an exemplary embodiment of the invention, said force vector includes at least two rotations directions relative to the force vector.

In an exemplary embodiment of the invention, the method comprises applying a second force to at least a second point on said body, simultaneously with said force.

There is also provided in accordance with an exemplary embodiment of the invention a method of rehabilitation comprising:

providing a first actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

coupling said first actuator to a first point on a human body;

providing a second actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

coupling said second actuator to a second point on a human body; and applying different forces to said points using said actuators.

In an exemplary embodiment of the invention, said first actuator applies a rotation.

In an exemplary embodiment of the invention, said different points are on a same limb.

In an exemplary embodiment of the invention, said different points are on different limbs. In an exemplary embodiment of the invention, the method comprises exercising the two limbs in concert. Alternatively or additionally, the method comprises copying motion from one limb to the other limb.

There is also provided in accordance with an exemplary embodiment of the invention a method of reverse kinematics, comprising:

controlling motion of at least one point on an organ using an actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;

controlling a position of at least a second point on the organ; and reconstructing by a computer of a value of a bending of at least one joint of said organ from said motion and said position.

There is also provided in accordance with an exemplary embodiment of the invention a rehabilitation device, comprising:

an actuator that includes a movement mechanism capable of applying a force that interacts with a motion of a patient's limb in a volume of at least 30 cm in diameter;

a support for a patient; and a controller adapted to adjust a rehabilitation exercise according to the relative positions of said actuator and at least one of said patient and said support.

In an exemplary embodiment of the invention, the device comprises a distance sensor for determining said relative positions.

In an exemplary embodiment of the invention, the device comprises an imaging sensor for determining said relative positions.

In an exemplary embodiment of the invention, said controller relates to the relative placement of said patient and said actuator.

In an exemplary embodiment of the invention, said controller assumes the relative positions differ only in two dimensions.

In an exemplary embodiment of the invention, the device comprises a pointer which indicates a desired patient placement.

In an exemplary embodiment of the invention, said controller is configured to use said actuator to determine said relative placement.

In an exemplary embodiment of the invention, said controller is configured to use said actuator to indicate a desired relative placement.

In an exemplary embodiment of the invention, said controller is configured to adjust said exercise on the fly, during an exercise session and in response to patient movement.

There is also provided in accordance with an exemplary embodiment of the invention a rehabilitation device, comprising:

a memory storing therein a correspondence between exercises and payment codes;

a controller adapted to control a rehabilitating exercise and generate a report including a code from said memory corresponding to said exercise.

There is also provided in accordance with an exemplary embodiment of the invention a rehabilitation device, comprising:

at least one actuator adapted to support motion of a body part;

at lest one sensor associated with the actuator and measuring said motion; and a controller which analyses said measured motion and generates a measure of quality of motion and which modifies a rehabilitation plan responsive to said quality of motion measure.

In an exemplary embodiment of the invention, the controller modifies a selection of future exercises according to a measured quality of motion.

In an exemplary embodiment of the invention, the controller modifies a selection of parameters for future exercises according to a measured quality of motion.

In an exemplary embodiment of the invention, the quality of motion measure used is defined as the degree of matching to a $2/3$ power law.

There is also provided in accordance with an exemplary embodiment of the invention a method of rehabilitation, comprising:

causing a person to carry out at least one exercise;

estimating a mental state of said person from a result of said at least one exercise; and automatically selecting at least one second exercise according to said estimation.

In an exemplary embodiment of the invention, estimating a mental step comprises comparing performance between two exercises, one or which is expected to elicit a higher compliance.

In an exemplary embodiment of the invention, estimating a mental step comprises comparing performance within an exercise, using the maximum ability of the patient as a base line against which variation can be determined.

In an exemplary embodiment of the invention, said estimating is automatic.

There is also provided in accordance with an exemplary embodiment of the invention a method of rehabilitation, comprising:

determining a patient's ability to perform a motor task;

determining a patient's ability to perform a non-motor task; and automatically selecting an exercise or parameters of an exercise for the patient according to said determinations.

In an exemplary embodiment of the invention, said selecting comprises matching an instruction or feedback modality to a perceptive ability.

In an exemplary embodiment of the invention, said selecting comprises matching an instruction or feedback modality to a cognitive ability.

In an exemplary embodiment of the invention, said selecting comprises an exercise or series of exercises designed to rehabilitate both of said motor and said non-motor abilities.

In an exemplary embodiment of the invention, said exercise rehabilitates visual-motor coordination.

There is also provided in accordance with an exemplary embodiment of the invention a method of rehabilitation comprising;

moving a motorized actuator having a tip to a spatial position within a volume having a diameter of at least 30 cm; and instructing a patient to apply force against said tip, wherein said actuator provides a compliant resistance to said force. Optionally, the method comprises selecting the resistance according to the spatial location.

BRIEF DESCRIPTION OF THE FIGURES

Non-limiting embodiments of the invention will be described with reference to the following description of exemplary embodiments, in conjunction with the figures. The figures are generally not shown to scale and any sizes are only meant to be exemplary and not necessarily limiting. In the figures, identical structures, elements or parts that appear in more than one figure are preferably labeled with a same or similar number in all the figures in which they appear, in which:

FIG. 5 illustrates a system including limb position sensing, in accordance with an exemplary embodiment of the invention;

FIG. 6 illustrates an elbow holding attachment, in accordance with an exemplary embodiment of the invention;

FIGS. 15B-15F show various attachments according to exemplary embodiments of the invention;

DETAILED DESCRIPTION OF EXEMPLARY EMBODIMENTS

General

The methods and apparatus of some embodiments of the invention provide for controlled, partially controlled or directed motion of portions of the body. The following sections describe this equipment by first describing the design of an exemplary device (an articulated arm), followed by various rehabilitation methods and then additional rehabilitation device designs and uses. The invention should not be considered as being limited to particular devices used to illustrate particular methods. Rather, many of the methods can be practiced with a variety of devices and many of the devices can be used to practice a variety of methods.

Articulated Arm Design

Figure 1:
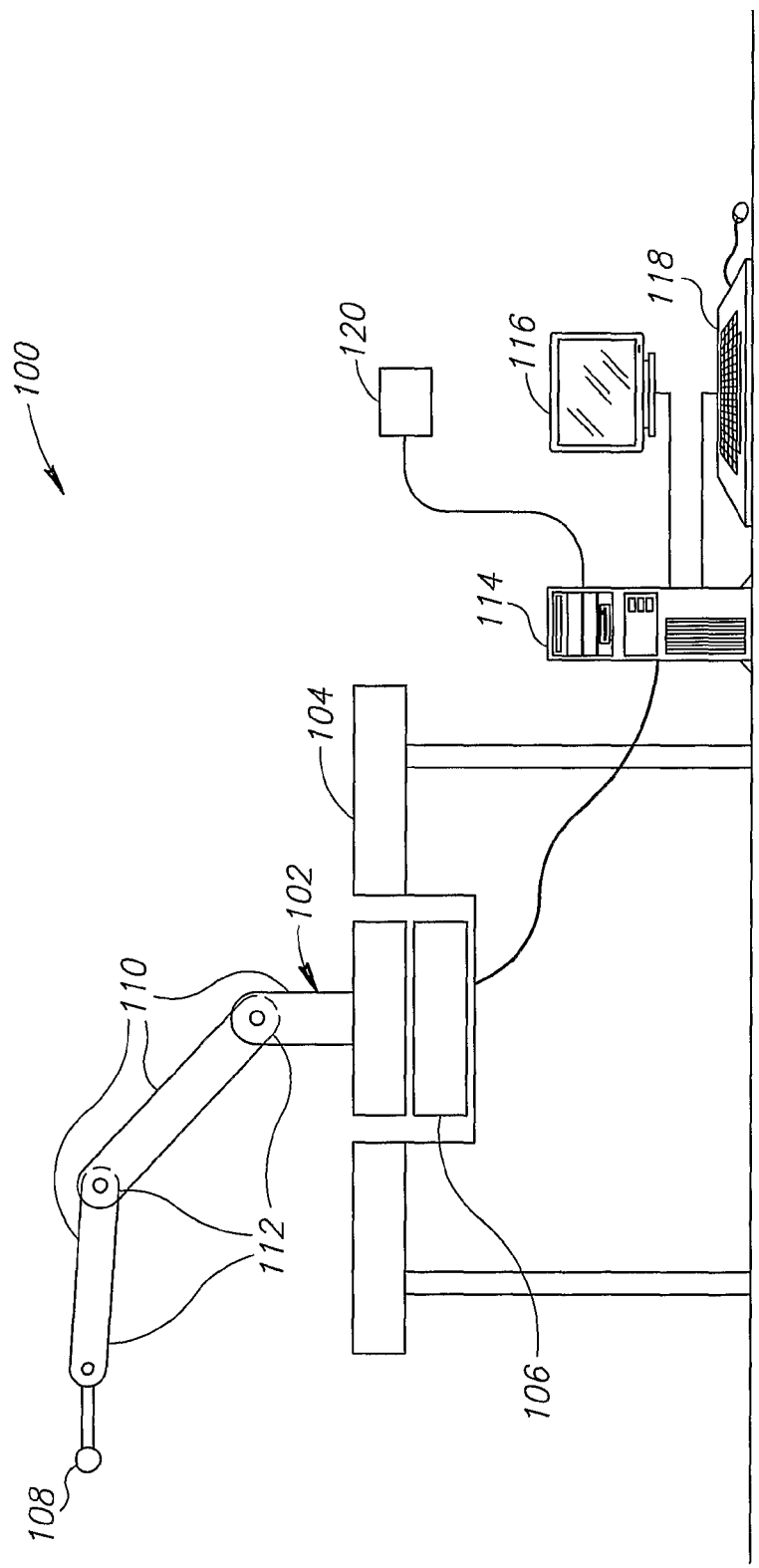
FIG. 1 is a schematic showing of an articulated-arm based rehabilitation device, in accordance with an exemplary embodiment of the invention.

FIG. 1 is a schematic showing of an articulated-arm based rehabilitation device 100, in accordance with an exemplary embodiment of the invention. In some of the description device 100 is referred to even though other devices described herein would suit just as well. The term "system" is used in some places instead of referring directly to device 100 and may also include multiple devices and monitors.

Device 100 comprises an articulated arm 102 that projects upwards out of a table or other pedestal 104. A tip 108 of arm 102 serves as a controlled point which can travel various 3D trajectories. Optionally, pedestal 104 is not attached to a floor but is instead weighted by an optionally weighted base 106 (which may be located elsewhere than shown), to prevent tipping or capsizing of device 100 during use. Optionally, base 106 includes electronics used to power the arm. Alternatively or additionally, weight 106 is a temporary weight, for example a water-filled bladder. Other exemplary general layouts are shown below.

In an exemplary embodiment of the invention, arm 102 is an articulated arm, which supports movement in 3D space. Alternative designs, for example based on a single joint and an extending arm, are described below.

In an exemplary embodiment of the invention, arm 102 comprises a plurality of sections 110 interconnected by a plurality of joints 112. In an exemplary embodiment of the invention, each joint is motorized, for example as known in the art of robotic arms. Alternatively or additionally, each joint is selectively lockable, for example as described below. Optionally, angular position sensors are provided at each joint and/or a position sensor at tip 108, so the position in space of arm 102 and/or of tip 108 can be determined. The joints may be joints with one, two, three or more degrees of freedom.

In an exemplary embodiment of the invention, arm 102 (e.g., its locking and/or force application and/or movement) is controlled by a controller 114, for example a personal computer or a dedicated embedded computer. Optionally, a display 116 and/or a user input device 118 are used for interaction with a user. Optionally, display 116 comprises (or is limited to) an audio display, for example for providing audible and/or speech instruction and/or feedback.

Figure 2:
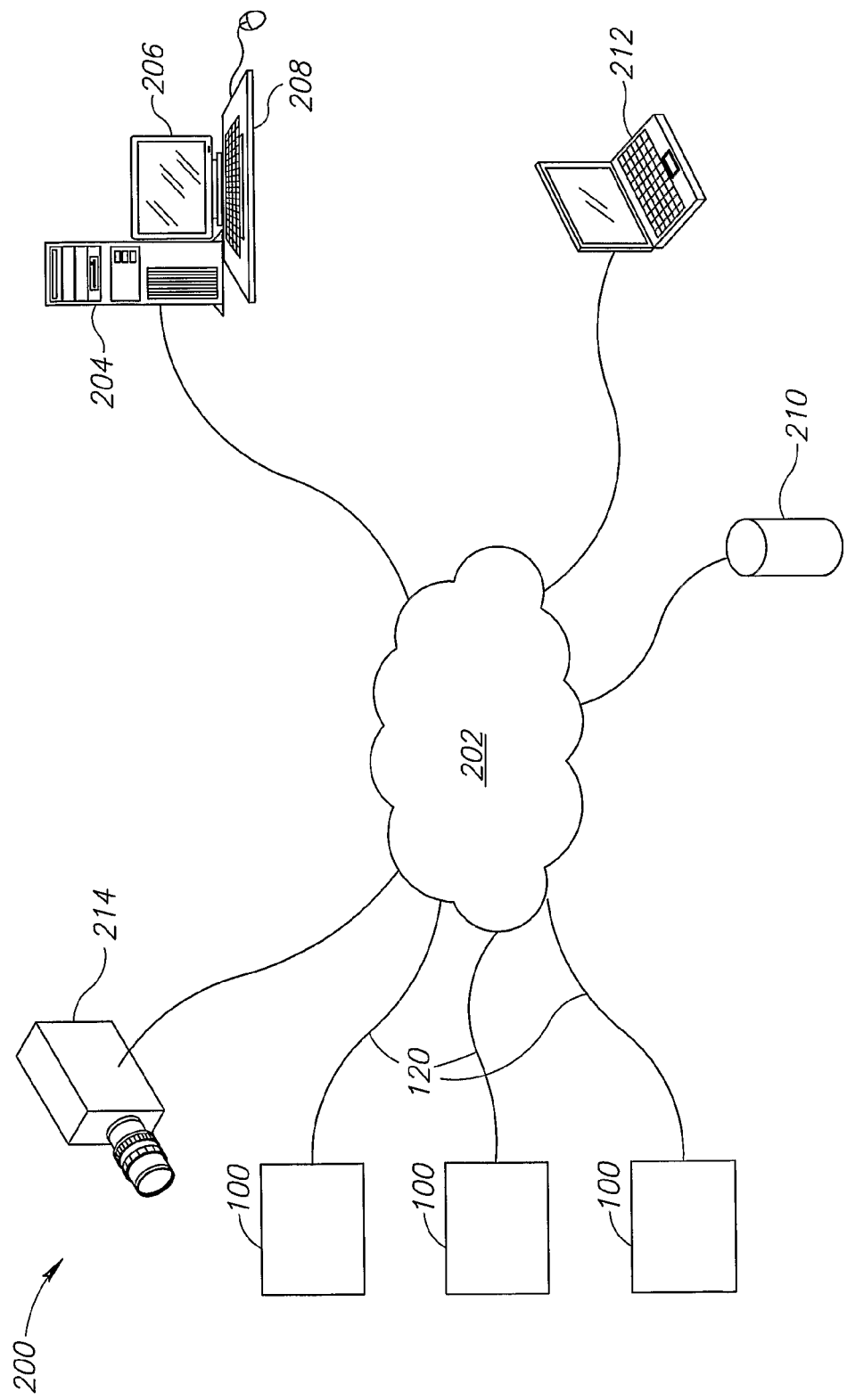
FIG. 2 is a schematic block diagram of a remote rehabilitation system, in accordance with an exemplary embodiment of the invention.

An external connection 120 for connection to a remote computer and/or other units, is optionally provided, for example for use as described in FIG. 2 below.

It should be noted that some implementations of device 100 include no computer. Some implementations require no electrical power. In one example, a mechanical computer is used to control the device parameters. In some embodiments of the invention, resistance to motion (optionally variable) is provided using a brake system.

Arm Specification

As will be described below in greater detail, various rehabilitation methods in accordance with exemplary embodiments of the invention require different types of motion and/or responsiveness from arm 102 or other devices as described below. In some embodiments of the invention the use of device 100 for rehabilitation places certain constraints on device 100, with respect to, for example, smoothness of motion, responsiveness, coupling between axes, balancing and/or supported range of motion.

For example, some types of rehabilitation in accordance with exemplary embodiments of the invention require a patient to move tip 108 along a trajectory. Resistance may be predefined along the trajectory or possibly no resistance at all is provided. In any case, it may be desirable that device 100 not adversely affect motions by the patient, at least if they are correct. In a particular example, tip 108 provides no resistance to motion along a certain trajectory and strongly resists motion not along the certain trajectory. Such a tip is termed a neutral directed motion tip.

In order to support generalized 3D trajectories in a neutral manner (e.g., not providing resistance at least along the trajectory of motion), arm 102 is optionally required to not have singularity points in a predefined and useful range of motion, for example a sphere of radius of 0.8 meters or less, for example, 0.5 meters or less. The term "singularity" is used to define a point and arm position where moving to an adjacent point passes the limits of one or more joints and requires a relatively large change in joints position, which is generally time consuming and is exhibited to a patient as a sudden resistance or delay. In addition, providing neutral motion means that a uniform (and desirably zero) resistance can be provided at any point in a desired range of motion. Possibly more important in some embodiments of the invention is that any changes in resistance be smoothly varying. In some embodiments, arm 102 provides a counter-force or even provides motion. Uniformity and controllability of such force is required in some embodiments of the invention. In some embodiments, tip 108 is configured to support a limb of a patient, so that the limb feels buoyant.

The magnitude of force that arm 102 can apply and/or resist depend on the rehabilitation methods with which it is to be used. For example, one rehabilitation type will require arm 102 to resist absolutely an incorrect motion, up to a force of, for example, 100 Kg applied at tip 108. In another example, it is sufficient that arm 102 resists motion up to a force level at which it is certain that the patient feels the resistance, for example, 1 Kg. A reminding force may be useful in some embodiments, for example, 10 Kg, which may ensure that a patient does not inadvertently move tip 108 against the force.

In an exemplary embodiment of the invention, the range of motion of tip 108 covers a volume of 50×50×50 cm. In other embodiments, a smaller or larger volume is provided. The volume need not be rectangular. Optionally, the volume also includes rotation of tip 108 around one, two or three axes. In some embodiments, the volume of movement of the tip is one or two dimensional (i.e., in a plane or along a line).

In some embodiments of the invention arm 102 is expected to respond to a patient's activity in a manner which will seem natural or at least not interfere with the rehabilitation motion. In an exemplary embodiment of the invention, the responsiveness of arm 102 is faster than 10 ms or better than 5 ms.

A general property of many mechanical systems is that due to manufacturing tolerances, sensing tolerances, design and/or non-optimality of the construction some uncontrollable freedom of motion is available. In an exemplary embodiment of the invention, the amount of uncontrolled motion in device 100 is less than 5 mm or less than 2 mm. In some embodiments of the invention, a spring-loaded mechanism is used to prevent unrestrained backlash motion.

Robotic technology for achieving such ranges of motion and responsiveness and forces are well known, albeit possibly at a high cost. Various additional suitable technologies are described below. Optionally, controller 114 controls arm 102 in a passive, active or a responsive manner to achieve these objectives. In an exemplary embodiment of the invention, such active control of arm 102 results in compensation for at least 80% or more of the moment of inertia of arm 102. It should be noted that different values may be required for different situations, for example a greater or lesser responsiveness or a greater or lesser uncontrollable freedom.

Arm 102 is, for example, 1 meter, 0.8 meters, 0.5 meters, 0.3 meters or any greater smaller or intermediate length.

Motion Types

In device 100 as illustrated, the motion which is controlled is that of a single point, i.e., tip 108. By providing various attachments for tip 108, tip 108 may be connected, for example to a bone, to a joint or to a different part of the body. The attachment may be rigid, for example using a strap or it may depend on cooperation of or action by the patient, for example, as a handle or a rest. Specific attachment devices, for example for a hand, arm, elbow, knee, ankle and/or shoulder may be provided. Further, as described below, multiple tips 108 (optionally with individual arms 102) may be provided for attachment at different points of the body, on a same or different body part.

Figure 3A:
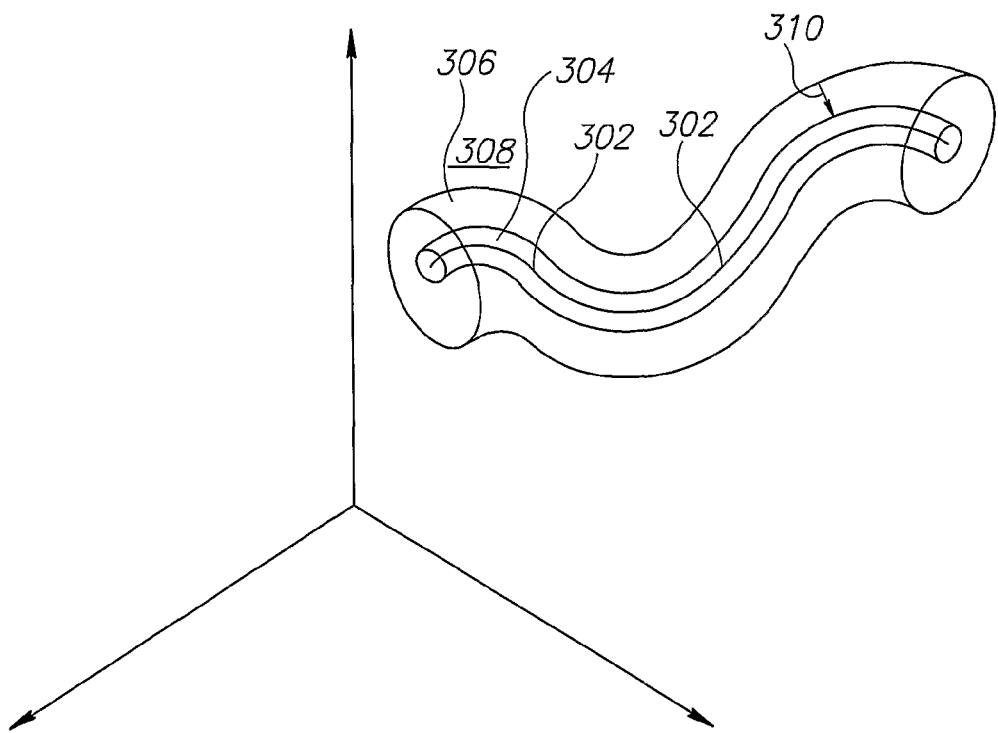
FIG. 3A illustrates a force field generated by a rehabilitation device in accordance with an exemplary embodiment of the invention.
Figure 3B:
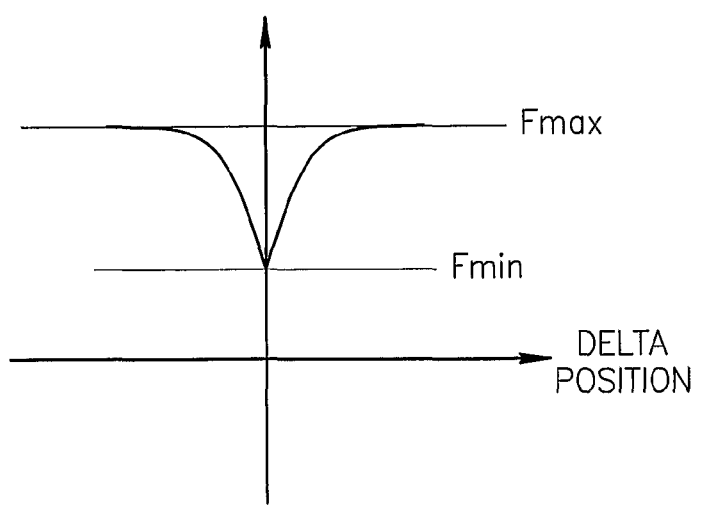
FIG. 3B shows an exemplary profile of a force of resistance.

When providing rehabilitation various types of motion may be supported, for example, one or more of:

a) Passive motion. Tip 108 is moved (by device 100) and the patient moves with it.

b) Resisted motion. The patient moves tip 108 and encounters resistance. The resistance may be of various magnitudes and may be uniform in all direction or be directional.

c) Assisted motion. When a patient moves tip 108, a positive feedback on arm 102 increases the force of motion in the direction moved by the patient.

d) Force field motion. The patient moves tip 108. Along a certain trajectory one level of resistance (or none) is encountered. Deviation from the trajectory is not allowed or meets with resistance. FIG. 3A shows an example of such a force field. Motion along a "correct" trajectory 302 can be without resistance, or possibly assisted. An increased resistance is exhibited in a volume 304 surrounding trajectory 302. An even greater resistance is exhibited in a surrounding volume 306. A prevention of motion may be provided in an outside volume 308. In an exemplary embodiment of the invention, a corrective force vector 310 is applied when not on trajectory 302, pointing towards trajectory 302. Optionally, instead of a corrective force, resistance varies as a function of distance from trajectory 302, thus, motion of tip 108 is naturally urged back to trajectory 302. FIG. 3B is a graph showing an exemplary relationship between divergence from a path and applied force. Optionally, the force is applied in the direction of the path. Alternatively, the force maybe a unidirectional force of resistance.

This type of motion may be used to help train the patient in a desired motion.

e) Mirrored motion. Motion of tip 108 is required to mirror the trajectory of motion of a different element, for example for dual limb rehabilitation as described below.

f) Free motion. Patient moves tip 108 in any way he desires, possibly receiving feedback. As the patient (or therapist or helper) moves tip 108, device 100, may record it for future playback. In a playback mode the prerecorded motion (or path) is optionally reconstructed using other modes. Optionally, the recorded path is modified (e.g., smoothed or otherwise edited), for example automatically or manually.

g) General Force Field. A force field and/or an assistance field is defined which is not related to any particular trajectory. For example, a range of trajectories may be allowed to be practiced by a user, or a real or virtual situation simulated (e.g., water, areas with obstacles).

h) Local force field. A force field which is applied to only a small locality and/or only in one or two dimensions.

i) Restricted motion. One or more points of the body of a subject are supported or prevented from moving. Optionally, the angles between such points and the moving points on the patient are measured. In one example the elbow is locked with a dedicated harness allowing only a shoulder motion. In some embodiments, the restriction is partial and/or is provided by a movable element (e.g., an arm 102).

j) Initiated Motion. The patient initiates the motion (e.g., a 1 cm motion or 100 gram force) and device 100 completes or helps the patient complete the motion in space. The completion may be of a whole trajectory or of part of a trajectory.

k) Implied motion. Device 100 begins the motion and the patient completes it. Device 100 may assist the rest of the motion in various manners (e.g., by changing to one of the modes described herein after the motion starts). If the patient fails to pick up the motion, device 100 may generate a cue, for example an audio reminder. Different parts of a single motion trajectory may each have a machine initiation definition. Optionally, if a patient is too slow in moving, device 100 begins the motion.

l) Cued motion. The patient receives a cue from the system before motion according to a different mode starts. The cue can be, for example, vibration of tip 108, stimulation pads on the skin, audio or visual cue. In some embodiments of the invention, the strength of the cue and/or its timing and/or other ongoing activities (e.g., a visual display and game) are used to help train the coordination between different modalities, for example, hand-eye coordination. A motion cue can be used to train a kinesthetic sense.

m) Teach Mode. Device 100 is taught a motion. In one example, a therapist performs a motion and motion parameters at each point are recorded and can then be used for an exercise. Another way of teaching the system is to use a path that the therapist uses. The therapist may use a control to indicate a point to be taught or a continuous mode may be defined by which an entire trajectory is learned. Optionally the path and points are edited before replay. Optionally, the paths are abstracted, for example, by smoothing or identifying motion points, before playback.

Thus, in some embodiments of the invention, rehabilitation device 100 can provide one or more of Isokinetic, Isotonic and Isostatic exercises.

It should be appreciated that a definition of a trajectory which tip 108 is to follow can include speed parameters (e.g., trajectory of path, trajectory of velocity, trajectory of force). For example, a user may be assisted, or urged, or expected, to move tip 108 at a certain speed. The speed may be, for example, absolute, or relative (e.g., requiring a uniform speed or the speed to match a non-uniform profile).

Optionally, an angular trajectory is defined, which places constraints on an angular orientation of tip 108. In some embodiments, the constraint is one dimensional. In others it is two or three dimensional.

Speed, angles and spatial trajectories in a particular rehabilitation scenario may each belong to a different one of the above motion types. For example, spatial trajectory may be of a force field type, while speed trajectory is free or assisted. The type of trajectory and/or its parameters may also vary along the trajectory, as a function of time and/or as a function of previous performance. For example, a smaller assistance at a later part of a trajectory may be provided for a type of motion which was properly (or better than expected) executed in an earlier part of the trajectory.

Trajectories may be absolute, for example, defined as a function of a resting point or a different point on device 100. In other embodiments, the trajectories are purely relative, for example, requiring a patient to move an arm in a straight line, regardless of starting point. In other embodiments, a trajectory is partially relative, in that once motion starts, this determines the shape of the rest of the trajectory, for example, a start of a trajectory indicating if a patient is standing or sitting, and thus what type of hand motion is expected.

In some embodiments, such as described below, where multiple points 108 are defined, the motion types of each point may be of different types. In some embodiments, what is defined is a trajectory as a function of two or more points in space. For example, if two points are used to define an elbow configuration (e.g., angle between bones), the trajectory constraints may be defined on the motion of the elbow. Such motion may be relative in space (e.g., a comparison of the two points) and not absolute (e.g., compared to a device reference point). In another example, different limitations are provided for different points, for example, angular limitations at one point and velocity limitations of another.

It should be noted that in some embodiments of the invention a tensor or tensor field is provided, as each point in space can have associated with it a speed, a force and/or a rotation, all of which can be scalar or a vector.

In some embodiments of the invention, different modes are defined for different parts of a trajectory or for different parts of space (e.g., for a particular arm). Optionally, a mode may be triggered based on the actual performance. For example, if motion velocity is below a certain threshold, a more assistive mode is provided. Similarly, a pause of over a threshold may imply a more assistive mode. An exact motion may imply a less assistive mode.

In an exemplary embodiment of the invention, modes may be changed automatically, for example, when nearing a patient motor limit (e.g., range of motion) or when nearing a cognitive limit (e.g., spatial neglecting zone or time neglect zone such as for long motions).

Exemplary Usage

Figure 4A:
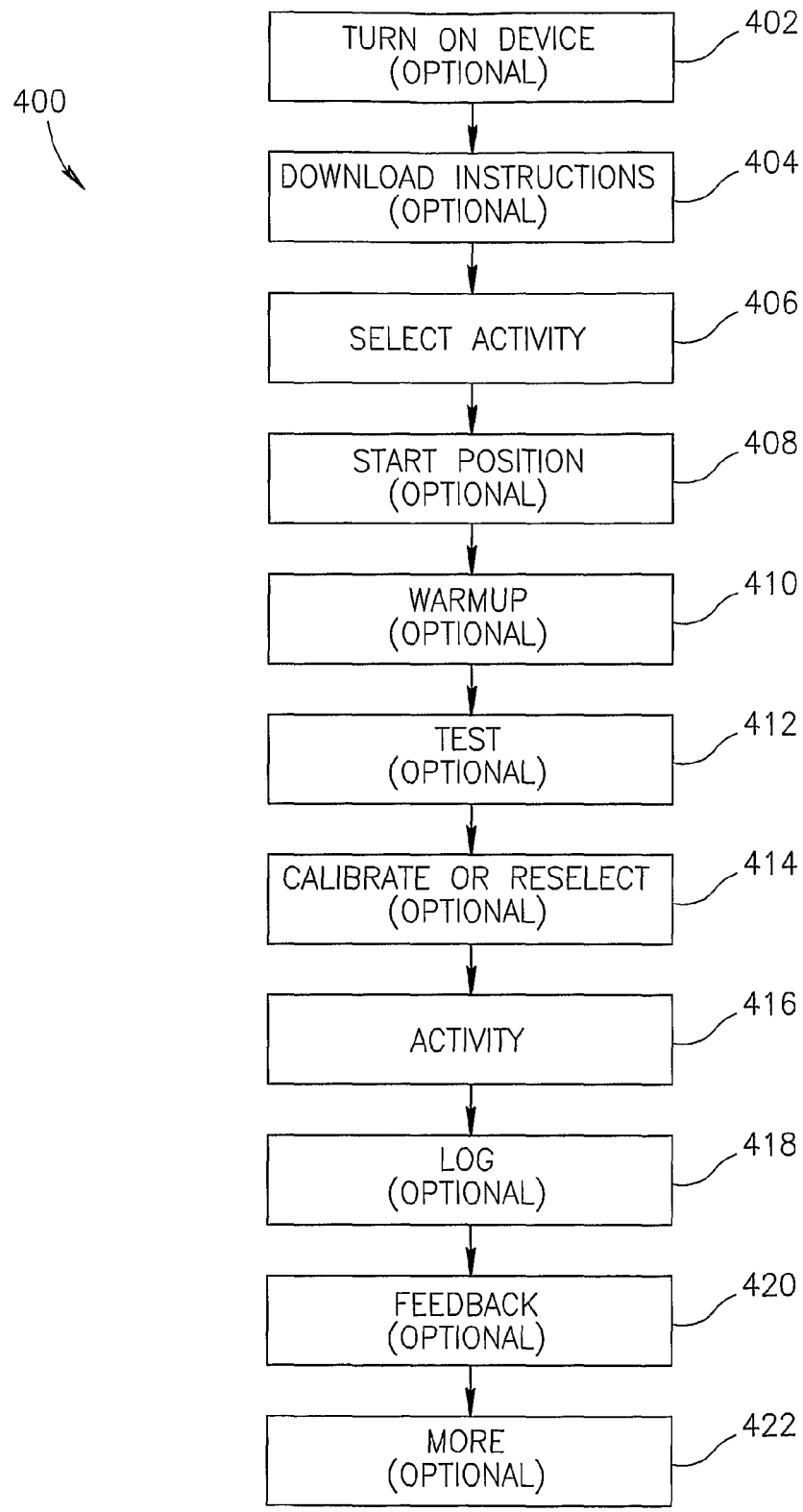
FIG. 4A is a flowchart of a method of using a rehabilitation device, in accordance with an exemplary embodiment of the invention.

FIG. 4A is a flowchart 400 of a method of using device 100, in accordance with an exemplary embodiment of the invention.

At 402, device 100 is powered on (for electrical devices). Optionally, device 100 turns on when arm 102 is touched or moved a certain amount. Alternatively, motion of arm 102 may provide power for device 100.

At 404, if remote connection 120 is used, device 100 optionally downloads instructions, for example what activities to suggest and/or what progress was expected and/or results from physical therapy at other locations. Optionally, a patient identifies himself to device 100, for example, using a code, selecting a name form a list or using a smart card or a magnetic card with user input 118. Optionally, rehabilitation information of a patient is stored or indexed on such a magnetic card or smart card or on a portable flash memory device or portable hard disk.

At 406, an activity to be performed is selected. In a more automated device, the selection may be, for example automatic or by a patient from a displayed list of options. In a less automated device, for example, a patient may follow a chart provided to him by a rehabilitation center or by a guiding therapist.

At 408, arm 102 is optionally moved to a start position thereof, for example by device 100 or by the patient (e.g., directly or by permitting device 100 to do so). It should be noted that in some trajectories no start position is predefined. Instead, the actual starting position is used to define the rest of the trajectory.

In some embodiments of the invention, the position of the patient relative to the system is indicated or measured (e.g. by vision system, by mechanical attachments) and the program is adjusted accordingly.

In some cases, device 100 is adjusted in another manner. For example, a particular handle may be attached at tip 108, or legs of the device may be raised or lowered. In a collapsible device (e.g., folding legs), the device may be set up. Optionally, such setting up is carried out before activating device 100.

At 410, an optional warm-up session is carried out on the patient, to ensure that he is ready for the activity. Optionally, one or more physiological sensors, for example a muscle temperature sensor (e.g., skin surface) are used to ensure (e.g., as a safety feature) that the patient is sufficiently warmed up.

At 412, the patient is optionally tested to confirm an expected current ability.

At 414, the results of the test are optionally used to modify one or more parameters of the selected activity or to select a different activity, for example, due to an under- or over-achievement of the patient during testing. Exemplary modifications include: slowing down expected speed, reducing expected or resistive force, reducing expected or allowed range of motion and reducing number of repetitions.

At 416, the activity is carried out, for example, continuous passive motion at 20 repetitions or motion (by patient) with resistance of 0.5 Kg, along the entire trajectory. In another example, the resistance grows as a function of speed, or if the speed is higher or lower than a defined speed trajectory, optionally using a mode or combination of modes as described above.

At 418, various measurements which are optionally made during the activity, are optionally logged. Such logging may also be carried out concurrently with the activity.

At 420, feedback may be provided based on the activity, for example, to the patient, a rehabilitation expert and/or to device 100. Optionally, feedback is provided on a patient physiological condition as well, for example, determining fatigue based on increased irregularities of motion and/or based on pulse rate or other physiological parameters.

At 422, a decision is optionally made to repeat an activity and/or to select a new activity. Such a decision may be made, for example, based on patient progress and/or fatigue.

In an exemplary embodiment of the invention, device 100 automatically generates CPT codes or other reports used for billing. Alternatively, a report is generated which a human therapist approves and/or modifies. In some embodiments of the invention the patient's progress is used to assess future expected payments and/or exercises and/or suggested human guidance. Optionally, such future factors, patient improvement, time elapsed and/or motivation of the patient in using and improving using the system, are used to decide on future financial support by a health care provider.

In an exemplary embodiment of the invention, if after a given time (e.g. several weeks) there is no improvement in function or other measurements a decision can be made to stop the financial support. In another example based on documented improvement in certain areas (e.g. patient accuracy) the treatment support can be extended. In another example, the therapy payer may insist on minimum system usage (for example if a system was delivered to the patient home). By reviewing an on going usage report (possibly on line) the payer can decide to extend or stop usage.

In an exemplary embodiment of the invention, the system can simply generate codes and/or reports, for example using a look-up table (each exercise can have an associated code) using table and also automatically generate reports regarding other factors, such as motivation and completion of plan.

Planning and Long-Term Progress

Figure 4B:
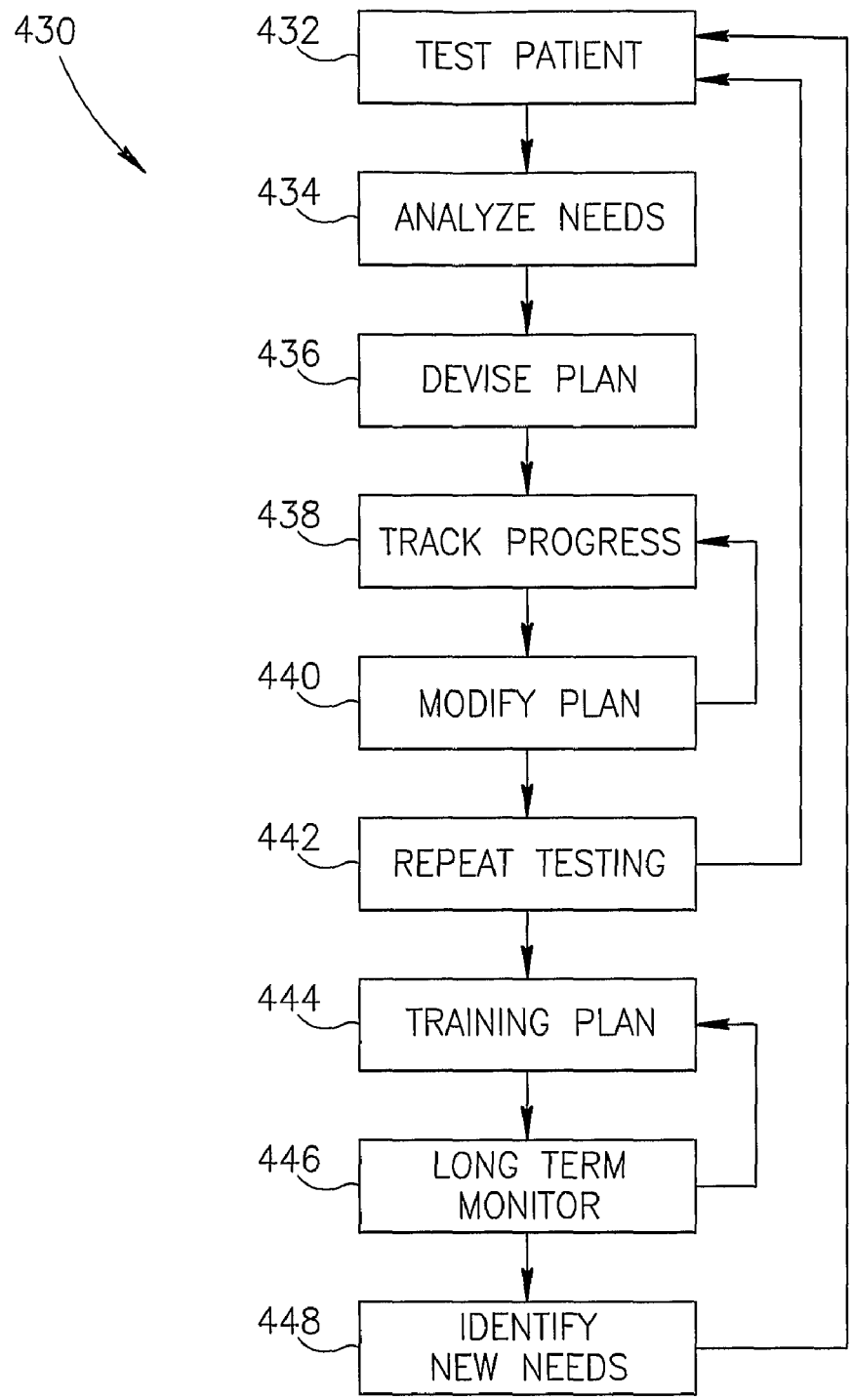
FIG. 4B is a flowchart of a long term use of a rehabilitation device, in accordance with an exemplary embodiment of the invention.

FIG. 4B is a flowchart 430 of a long term use of device 100, in accordance with an exemplary embodiment of the invention.

At 432, a new patient who is identified as needing rehabilitation is tested, possibly using device 100. For example, such tests may include range of motion tests, tests of maximum applied force at different points in space, and/or tests of fineness of force control and motion control. In an exemplary embodiment of the invention, device 100 calculates limb size (or detects them using a camera) and uses the limb size to adjust pre-stored exercises, for example to adjust their trajectories and/or starting point.

At 434, the results of the tests are analyzed to determine the needs of the patient and to formulate objectives of the rehabilitation. This act may be, for example, manual, automated or manual with support from device 100.

At 436, a rehabilitation plan is drawn up, including, for example one or more of an expected progress chart, various allowed and/or required exercises and exercise parameters for different parts of the plan, definitions of increased and decreased difficulty levels for the exercises, allowed and/or required exercise sequences, number of cycles for each exercise, warm-up requirement, list of data to log, list of patient-modifiable information, one or more safety parameters which should not be passed and/or one or more parameter alert values at which an alert should be provided to the patient and/or a rehabilitation expect monitoring the patient's progress. It should be noted that while generating a rehabilitation plan is a known activity, in an exemplary embodiment of the invention, such a plan is special, for example, taking into account one or more of the possibility of long term rehabilitation, the possibilities involved in having a device available at a home for multiple short sessions, the provision of multiple activities with a single device, the needs of remote monitors and/or the programmability and responsiveness of a device in accordance with some embodiments of the invention. The plan may be generated manually, automatically or manually with the assistance of device 100, for example an initial plan generated automatically and then annotated or approved by a human.

At 438, the plan is carried out, while being monitored. In an exemplary embodiment of the invention, the monitoring is manual. Alternatively, at least some of the monitoring is automatic.

At 440, the plan may be modified in response to the monitoring, for example, if slow progress is detected, the plan time frame may be changed.

In some cases, as rehabilitation progresses, new problems may come up or become emphasized. In some cases, the plan may be modified (440). In others, testing may be repeated (442), generally to a lesser extent than when the patient was initially evaluated.

In some plans, periodic testing (for example on device 100 at the patient's home) is part of the plan. Such evaluative testing may also be used to determine when rehabilitation is complete.

At 444, rehabilitation is mostly completed and a training plan is optionally made, for example to ensure maintenance of the rehabilitation or for other reasons (such as prevention of worsening or prevention of limb or joint neglecting).

At 446, long term monitoring of the patient may be performed, for example, testing the patient's abilities once a week or once a month.

At 448, new needs of the patient may be identified, for example based on the monitoring or based on a periodic general test. In one example, a patient being rehabilitated for stroke may be determined after a time to need rehabilitation for a progressing arthritic condition. In an exemplary embodiment of the invention, a personal profile is created for a patient. For example, such a profile may include a series of items to work on, for example smoothness of motion, which can be tackled one by one over time or if a certain threshold value is detected during testing (e.g., quality of motion went below a threshold).

As noted herein, a particular property of some embodiments of the invention is that device 100 may be used over a wide range of situations, including long range treatment and following a patient from initial rehabilitation through follow-up rehabilitation (e.g., to maintain an ability) and diagnosis.

Scoring and Time Estimation

In an exemplary embodiment of the invention, the ability and/or progress of a patient are scored. In an exemplary embodiment of the invention, such scoring is used as an aid in deciding on the need and/or type of future rehabilitation. Alternatively or additionally, scoring is used to monitor the effect of rehabilitation exercises and/or help select between exercises. Alternatively or additionally, scoring is used to ensure that a patient's needs (e.g., personal rehabilitation needs or need for balanced rehabilitation) are met. In an exemplary embodiment of the invention, scoring is used to identify areas where progress was made and areas where additional therapy or modified therapy may be needed, due to lack of progress.

In an exemplary embodiment of the invention, one or more of the following measures are used to score a patient's ability and/or progress.

a) Motor scores may include one or more of Range of motion, time of motion, force, smoothness, lack of tremor, degree of tremor, spasticity, muscle tone, accuracy, quality of motion and/or force finesse (control of force, e.g. not breaking an egg). These may be defined for a single joint or for a complex motion, for example for pinching between fingers, holding in a hand, moving of an arm. In addition some functional scores may be used to e.g.—the speed at which the patient can move a filled glass, and the ability to pick and place an object.

b) Cognitive scores may include one or more of coordination between motion (motor skills) and senses (e.g., visual, auditory), speed of reaction, % of successful task completion, quality of completion, mistakes, planning ability, level of instruction complexity used (e.g level 1 is a simple visual & auditory instruction such as a forward arrow on screen & audio verbal instruction, while level 5 is a complex screen to motion interaction, such as following a 3D path as shown on screen).

c) Mental stores may include one or more of: successful task completed at patient capabilities and/or pain envelope, measure of self work, amount of nudging required from the system, consistency of use (e.g., at home).

In an exemplary embodiment of the invention, scoring of the patient is calibrated to other patients, for example, using a database of similar injuries, or using scores of patients that are being rehabilitated at a same time. Alternatively or additionally, scoring is carried out between a healthy and a non-healthy limb.

In an exemplary embodiment of the invention, scoring is used as an aid in diagnosis. In an exemplary embodiment of the invention, when diagnosing a patient, scores are generated (e.g., by providing suitable exercises) for individual body part abilities and for general abilities. In an exemplary embodiment of the invention, device 100 can analyze a patient's abilities by generating experiments and then analyzing the results. In one example, device 100 tests whether a patient will respond better to one type of exercise or to another by generating a series of exercises including both types of exercises. The results of the patient's performance are then analyzed to extract trends which indicate which of a controlled variable had a better or a desired effect on the patient. Optionally, a human therapist selects the initial possible exercises. Alternatively or additionally, a human therapist determines what percentage of time may be spent on such exercises. The scoring method or resolution may be adjusted by the therapist per the patient condition for example, adjusting the accuracy of measurement or the dynamic range of the score or the expected results (e.g., for qualitative measures).

In an exemplary embodiment of the invention, a patient may show an increase in a muscle strength score but not show a corresponding increase in accuracy (correspondence may be, for example according to a table or according to a previous trend of the same patient, possibly with a same limb). In such a case, the exercise plan for the patient may be modified to include more accuracy-focused exercises and fewer muscle building exercises. It is noted that not all rehabilitation plans aim for concurrent improvement in multiple measures. In some plans, one measure is focused on and once a desired improvement in that measure is achieved, a different measure is focused on.

In an exemplary embodiment of the invention, a score in progress is used to estimate a time to reach a goal. Optionally, such estimation is based on one or more of the following variables: motivation, innate ability and current disability. Optionally, innate ability is estimated by tracking the progress. Optionally, a set of results and estimated times for different situations are stored in a database and used to generate an estimate. Optionally, a neural network is used. Motivation is optionally estimated using methods as described below. Alternatively, manual estimation may be provided. Optionally, a time estimation also includes thresholds of different scores which must be met. For example, an estimate may be conditioned on a certain motivation being maintained. Detection of a reduction in motivation may be used to prompt an update in expected progress or suggest certain treatment.

Home Use

In an exemplary embodiment of the invention, device 100 is adapted for home use. Such adaptation may include one or more of the following features:

a) Small size. For example, device 100 may take up less than 1 square meter of floor space. Optionally, device 100 is sized to fit through standard door ways (e.g., of width of 60 cm, 70 cm or 80 cm).

b) Simple interface. In an exemplary embodiment of the invention, device 100 has a simple interface to a user, for example including a small number of options to choose from, graphical and/or speech instructions of use and/or feedback designed to be understand by a typical adult. In an exemplary embodiment of the invention, a wired or wireless pendant or wrist-worn controller is used. For example, such a controller can have a limited set of commands, including, an exercise selector dial, a button for selecting a dry-run or a slow version of the exercise, an activation button to start or stop an exercise, a scale or a pair of buttons to increase or decrease exercise difficulty level, and a LED or LCD display for feedback (e.g., red LED for bad and green LED for good). In an alternative embodiment, device 100 is voice activated and controlled, for example using an IVR (interactive voice response) type menu system.

c) Flexibility. In an exemplary embodiment of the invention, device 100 is designed to be used by a range of different sized patients (or persons living in a home) and for a range of different treatments, for a plurality of different body parts and/or appendages, for example, 1, 2, 3 or 4 limbs or body parts or more. In some cases, various attachments may be provided. Optionally, device 100 is adapted for positioning at various orientations and/or in proximity to home activities, such as at a table for rehabilitation of feeding and or activity of daily living.

d) Lack of fixation. In some embodiments of the invention, device 100 is either simply fixed to a surface or not fixed at all, simplifying installation and de-installation.

e) Mobility, detailed below.

f) Other home settings are optionally supported as well, for example, when the patient is in bed, in the living room and/or in a backyard.

In an exemplary embodiment of the invention, device 100 is connected to home appliances such as a TV or HiFi system. In an exemplary embodiment of the invention, the patient can be instructed from the TV or the user can play with the system using the TV as feedback. In another example, a set-top box is used as a local processor and/or a communication port to a remote station.

In an exemplary embodiment of the invention, use is made of the fact that device 100 is at home and conveniently located for the patient to use many times a day. In one example, rehabilitation activities are designed to cover a larger part of the day than is possible at an institute, for example, half or all of a day, while still allowing a patient to have a life with non-rehabilitation activities. For example, a rehabilitation plan can call for ten 5-minute sessions spread over an entire day, spaced by an hour.

In another example, device 100 interacts with real-life activities and/or using real-life objects, as described in more detail below. In particular, this allows a rehabilitation plan to show (and achieve) a real progress in the patient's ability to deal with real life situations, such as eating and getting dressed.

In an exemplary embodiment of the invention, devices in separate houses are interconnected, for example, within a family or between friends. Optionally, one of the participants may interact using a computer, rather than a device 100 (e.g., using mouse motions to emulate device manipulation, or as a player in a game using standard computer interfaces).

In an exemplary embodiment of the invention, device 100 communicates with an outpatient clinic so that home activities and clinic activities are synchronized. Optionally, the patient carries a memory unit (e.g., a USB memory card) that includes his personal data.

In an exemplary embodiment of the invention, the home system generates reminders to the patient to exercise, for example, audio reminders or e-mail or SMS reminders.

Remote Use

As noted above, device 100 is optionally used as part of a distributed system. FIG. 2 shows an exemplary distributed rehabilitation system 200.

One or more homes with rehabilitation devices 100 are shown. A network 202, for example an Internet, a cable network, a cellular network or a telephone network, connect device 100 to a remote site. In an exemplary embodiment of the invention, a remote site is a rehabilitation center including a computer station 204 with a display 206 and a user input 208. A single station 204 can monitor multiple devices 100, optionally in real time. A plurality of stations 204 may be provided, at a same or different sites. Optionally, a plurality of stations 204 are used to monitor a single device 100. For example, each device 100 may have a low level monitoring by a semi-skilled person, who shows difficult problems to a skilled monitor who is in charge of or associated with many unskilled monitored.

Also shown is an optional portable connection 212, for example using a laptop computer.

Also shown is an optional remote database 210, which may store data for one or more patients, for example, 100 or 1000 patients or more. While the database may be at the rehabilitation site, this is not required. In some cases the database is distributed, for example, among rehabilitation sites and/or user devices 100.

In an exemplary embodiment of the invention, a group of patients are collected into a network based on them having similar (or overlapping) aliments, treatment and/or prognosis and/or according to personal matching. In an exemplary embodiment of the invention, the progress of members of the group are presented to other members, possibly spurring competition. For patients with a lower motivation, a support group may be provided, for example, one in which the patient is more advanced than other members or one in which a group effort is being carried out instead of a competition.

In one example of a group activity, each of a plurality of patients has a role in a role playing game. The difficulty of each patient/role may be set according to the patient's ability. A group leader may be selected. In another example, each player is required to copy the movements and/or instructions of the group leader. Optionally, each player is protected from over-reaching his abilities by his device 100.

Other types of users may be supported in addition to monitors, for example, a patient's general practitioner physician, or a family member or caregiver may be able to log on and review a patient's progress.

Remote rehabilitation can follow several paths, for example, one or more of:

a) Real-time monitoring. Optionally, a camera 214 is provided adjacent device 100 to allow a therapist to detect problems and/or give advice to a patient. Optionally, the data is analyzed by the therapist in real time. Optionally, a real time reconstruction with animation software or VR (virtual reality) is used. Alternatively, off-line analysis is provided. Different pay schedules may be provided for different types of monitoring. In addition, different rehabilitation needs may indicate the level of interaction between a remote therapist and a patient. Optionally, camera 214 is controllable by the therapist, for example to zoom and/or pan to certain parts of the patient. Optionally, the path of the camera is pre-planned to track planned or actual motion by the patient and/or of various points on a body of the patient. Alternatively or additionally to camera 214, real-time monitoring may be provided by various position and orientation sensors associated with device 100. This may also require only a reduced bandwidth as compared to visual monitoring.

In an exemplary embodiment of the invention, a therapist can provide real-time feedback, for example using audio-visual methods and/or by commanding device 100 to respond in a certain way, for example, to increase force, to change a trajectory or to prevent a patient going past a safety limit.

b) Live start. A rehabilitation session is started live (e.g., on camera) and once the therapist is convinced the patient can work on his own, monitoring is stopped. Optionally, a patient can request help, for example during an activity or between activities.

c) Planning. Plans including exercises and/or programming for device 100 are provided by the remote site, for example, weekly, or at the start of each session. In some embodiments, planning is automatic and optionally performed with or without patient input at device 100.

d) Monitoring. A remote site can specialize in analyzing data uploaded to it from device 100 or another location and suggest changes. Other types of monitoring can also be practiced, for example, checking to see how regularly a patient uses the system and/or for following complaints. A rehabilitation center may perform, for example, weekly checkups and possibly require periodic testing. Optionally, a patient may be called to come to the rehabilitation center, for example, for testing, teaching and/or additional therapy.

e) Testing. In an exemplary embodiment of the invention, a remote site uses device 100 to administer tests to a patient and assess his condition and/or progress. In an exemplary embodiment of the invention, such testing is used to assess the efficacy of drugs and/or other treatment prescribed for the patient. Optionally, periodic testing is used to select a most useful drug, for example, for a patient with Parkinson's disease or for a spastic patient.

f) Home therapist. In some embodiments of the invention, a therapist will come to the patient's home for a rehabilitation session. For example, the therapist can set up device 100, mark correct starting positions, calibrate device 100 for the particular patient (e.g., size) and/or teach the patient the use of device 100. Optionally, the therapist can access and/or be in contact with a remote site, for example, for advice and/or monitoring of his work. When a therapist comes for later sessions, the remote site may assist with comparing current and past performance, for example. Optionally, a therapist brings device 100 with him. Optionally, a therapist brings two devices. Optionally, a device brought by the therapist is used to control a rehabilitation device already at the patient's home.

g) Remote maintenance. In an exemplary embodiment of the invention, device 100 can be maintained from a remote location, for example, including one or more of reporting by device 100 of technical problems; remote testing of mechanical abilities of device 100, with or without patient assistance; remote testing of sensing abilities of device 100, with or without patient assistance; downloading and uploading logs; and/or downloading and uploading software. Optionally, device 100 collects billing information which is remotely accessed. Optionally, device 100 collects usage information which may be used, for example, by an insurance company. In some embodiments, remote access to device 100 is designed to maintain a patient's privacy, for example by hiding patient identifying information, by limiting access to various logs and records and/or using password and other authentication schemes.

h) Remote motivation session. In an exemplary embodiment of the invention, device 100 is used to detect a reduced motivation level and a live therapist (optionally provided at need) can provide live encouragement and/or instruction. Live remote sessions in general may be provided.

In an exemplary embodiment of the invention, virtual reality methods, for example goggle mounted displays are provided at the remote location, to help the remote operator feel in better control. Alternatively or additionally, the operator can manipulate his viewpoint. In an exemplary embodiment of the invention, various sensors (for example as described below) are used to move a model of the patient, for remote and/or local feedback.

Other Usage Scenarios

Device 100, in some embodiments thereof may be used in other ways than described above. For example, in one embodiment of the invention a supervised group is provided, in which one or more therapists watch/monitor/support a plurality of patients, each on a different device. In such a supervised group, one or more of the following scenarios may be acted out:

a) Bring along—a therapist brings a plurality of devices 100 to a civic center or old age home or the like, and teaches a session to a group of users.

b) Game—each patient plays a part in a game and a score is kept. In the example of an adventure game (e.g., a role acting game), patients can earn life points, weapons, abilities and other items by improving their abilities using rehabilitation exercises. The game may be personally adapted to one or more patients, for example by providing assistance to those patients who require it. In an exemplary embodiment of the invention, the games require a patient to carry out certain physical activities. The activity may vary between patients according to their needs for rehabilitation. VR or simpler display technologies, such as screens may be used to help patients become immersed in the game and focus less on the other players. Such games can be played also when the patients are distributed and interconnected by a network, such as the internet.

c) Call-in group—the patients can join an existing group or game or session, to form a virtual "therapy room". Optionally, a chat line is provided concurrent with the rehabilitation exercises. Optionally, a rehabilitation server is provided for devices 100 to connect up to and register requirements, obtain connections to other devices and/or control access to a therapist.

In an exemplary embodiment of the invention, a group is supervised by a therapist and the therapist can monitor the group using a web cam, for example. Alternatively or additionally, patient's exercises can be reconstructed on the therapists system using VR or simulation. Alternatively or additionally, the therapist can review data generated by the system, such as scores. Optionally, different levels of interaction between the therapist and patients can be provided, for example, based on payment plan. In one example, a live connection is available to only higher paying patients. In another example, a web-cam interface is available only to higher paying patients. Similarly, the payment plan may dictate other parameters of treatment, for example, complexity of exercises, level of review, interaction between patients and quality of audio visual effects and/or games. Optionally, the amount of rehabilitation actually provided by the system also depends on the payer. Alternatively or additionally, the payer is billed according to the rehabilitation performed.

d) Test and/or train—In an exemplary embodiment of the invention, the group is used by the therapist to try out new therapy ideas and receive feedback form the patients, in real-time on the relative benefits and problems with different methods. Optionally, such a group is used for training purposes, for example to allow a therapist to view multiple patients at same and/or different conditions, substantially simultaneously. Optionally, if differences are identified, the therapist can be trained to detect such differences and/or be shown how to differentially rehabilitate for them.

In an exemplary embodiment of the invention, a linked-system scenario is carried out. In one example, two devices are connected using a master-slave relationship for example using a wired or wireless (e.g., BlueTooth, Cellular or WiFi) connection between them, or using a network connection between them. A master can be, for example, a son (or daughter) and the slave is an aged parent whom the son is assisting in rehabilitation. This allows a paretic parent to use the rehabilitation exercises as a means for maintaining contact with the family. Alternatively or additionally, the paretic parent may receive support from family members. Such support may also include advice on how to use the system and/or on what exercises to try.

Another exemplary usage of linked devices 100 (or a single device with multiple arms 102) is for child play. In an exemplary embodiment of the invention, a paretic child plays with a healthy child, each child manipulating a separate arm or device. Optionally, the motor abilities of the paretic child are compensated for by device 100, for example, providing speed enhancement or providing periodic automated action. If the children play a role-playing game or a sport simulation (e.g., tennis), device 100 can supplement the abilities of the paretic child, while still allowing the child some control over the game, for example, allowing the paretic child to actually perform 20% of the moves. Device 100 can control the level of support for the paretic child to ensure a level playing field.

Feedback and Patient User Interface

Various types of feedback are envisioned for use with exemplary embodiments of the invention, for example, one or more of:

a) Feedback from a patient. Optionally, a patient can provide feedback to a therapist, for example, using voice annotations or text annotations. In one example, such feedback is provided during an activity. In another example, a patient reviews a recording of the activity and then adds comments. In some activities supported by exemplary embodiments of the invention, a patient is requested to manipulate a control, when a certain situation is reached, for example, a maximum force. Feedback may also be provided by the patient for a plan or progress, not only for individual activities.

In some embodiments of the invention, patient feedback is processed by device 100 to modify and/or decide on current or future activities and/or their parameters. For example, if a patient marks that a certain force is a maximum force, later activities will not pass that force. In some embodiments of the invention, no explicit user feedback is required, instead, the system can implicitly determine when a maximum force is approached, for example based on difficulty in control, and model future activities on the thus determined force.

b) Feedback to patient. In an exemplary embodiment of the invention, feedback is presented to a patient, for example, during an activity, in rest breaks and/or after an activity. For example, such feedback can include an indication to the user that he is performing an activity incorrectly, that future cycles should be done differently and/or a comparison between current and past performance and/or other statistics. It should be noted that in many cases positive feedback is as important or even more important than negative feedback. This may depend on the rehabilitation method used. A positive feedback can be, for example, an auditory encouragement, a sound of clapping hands, a visual pleasing screen and/or a score increase.

Various feedback modalities may be provided, for example, speech and audio feedback, a display containing text or graphics, a marked up video image, force or vibration feedback on device 100 (e.g., by tip 108), using a separate element (such as the above pendant) and/or using virtual reality devices, such as goggle mounted displays, in which the type, position and/or other parameters of a mistake (or correct action) are shown overlaid on a real or virtual image of the activity.

As described, for example, in U.S. Provisional Application 60/633,429 filed on Dec. 7, 2004, also being filed as PCT application on same date as the present application and by the same applicant, entitled "Rehabilitation with Music", the disclosures of both applications are incorporated herein by reference, the disclosure of which is incorporated herein by reference, music may be used as a feedback modality, especially for patients with limited cognitive speech and/or visual ability. For example, music can be used to indicate a quality of motion, be generated by the motion or be used by device 100 as instructions or cues to the patient.

c) Feedback to therapist. In an exemplary embodiment of the invention, a local or remote therapist is provided with feedback. Such feedback can include, for example, one or more of extent of use (e.g., including whether patient is exercising when therapist is not paying attention), force levels, an indication of mistakes, a notification of missing, exceeding or meeting certain parameters, a predefined alert, a motion quality (described below) a safety situation and/or a statistical analysis of a current and/or a past activity.

d) Feedback from remote therapist. In an exemplary embodiment of the invention, feedback is provided by a remote therapist, for example as indicated above of feedback that a patient may receive. Optionally, such feedback includes instruction to device 100 whether to repeat a certain exercise and/or modify parameters. In an exemplary embodiment of the invention, an exercise is defined with, or a therapist can add, break points, at which the therapist, patient and/or device 100 (depending for example on implementation) can decide, for example, if to modify future parameters, impose a rest and/or repeat an activity if a desired result was not achieved. Such a breakpoint need not be notice by a patient, if no decision is made by him and a decision is made fast enough or during a short, pre-defined, break.

e) Feedback from device 100. Depending on the automation level of device 100, feedback can be provided by the device, for example indicating a threshold was past or indicating a safety problem.

f) Feedback from sensor patches attached to or image based analysis of the patient and/or device 100. Exemplary such patches are described below with reference to FIG. 5.

g) Feedback from one device to another, for example, in a master-slave mode of operation.

In an exemplary embodiment of the invention, speech is part of the rehabilitation process. In one example, device 100 responds to or expects voice commands. In another example, device 100 generates voice instructions.

Simple interfaces may be required for some users. In one example, instructions to a user (patient) are simple red/green lights, to indicate go and stop.

A plurality of different types of cues may be provided to indicate a need to act by the patient, for example, audio, tactile, vibration (of device 100 or of a patch), motion of opposite limb, visual (e.g., flashing screen) and/or change of speed. In an exemplary embodiment of the invention, a jolt, for example an audio blast (or shout) is used to alert an otherwise non responding patient, for example.

In an exemplary embodiment of the invention, a dummy body is used to show the patient the effect of the motion of device 100 (e.g., arm 102) on the patient.

Optionally, the complexity of the interface used increases as the patient rehabilitation progress and the patient's cognitive abilities improve and/or the patient has more attention to spare. Optionally, for example as described below, the user interface is used for performing concurrent cognitive, perceptive and motor rehabilitation, for example, by selecting the interface used to match an ability of the patient and/or train the patient in certain non-motor activities.

Mental State

As noted above, the progress of rehabilitation of any particular patient typically depends on one or more of the following: cognitive ability (if the patient cannot think clearly, motor planning is difficult or impossible), mental ability (if the patient has no motivation, rehabilitation is difficult) and motor capabilities.

In an exemplary embodiment of the invention, one or more of these may be measured and/or supported by device 100. Optionally, changes in the degree and/or type of support are determined by system 100. Alternatively or additionally, changes in support are determined by a user, or a plan of how to change support according to scores, is set by a user.

Support of cognitive abilities is, for example, by providing a simple display, multiple modes of presentation of information, reminders and/or multiple cues. Cognitive abilities may be tested, for example, by providing tests or by assessing performance in games where cognitive ability is required. In some cases a distinction is made between cognitive abilities and perceptive abilities.

In an exemplary embodiment of the invention, the patient is required to execute a motor task (e.g. move forward) his ability to understand the task depends on the cognitive capabilities. The ability to see a target on the screen or actually receive the instructions (e.g., visual or verbal) depends on his perceptive abilities.

Support of motor capabilities is, for example, by the various modes of motion described above. Measurement of motor capabilities is, for example, by providing exercises having a standard range of results and placing the results on a known scale.

In support of the mental state, various methods are provided herewith in some embodiments of the invention:

(a) Device 100 (or a remote controller) can supply the initiative instead of the patient, for example, initiating motions and initiating exercise repeats.

(b) Device 100 can provide incentive, for example, scores, special feedback elements, such as images, jokes, funny icons, laughter and/or rest periods.

(c) Device 100 can support groups, where members of the group provide motivation for each other, for example, via cooperation and/or competition.

(d) Device 100 can provide games.

(e) Device 100 can indicate a lack of motivation which suggests a need to provide consoling.

(f) Device 100 can increase patient motivation and reduce fear by presenting safety features and/or features design to reduce pain (e.g., a user indicating a pain range and device 100 ensuring that the pain range is exceeded only when the patient is forewarned). In an exemplary embodiment of the invention, a user indicates a pain range to device 100 by pressing a control when a pain point is reached or by a therapist doing so. Specialized pain sensors may be used as well, for example, detecting nerve activity or detecting physiological changes such as sweating or increased pulse.

(g) Device 100 can selectively provide positive feedback or negative feedback.

(h) Device 100 can be set to more or be less forgiving of errors.

(i) Device 100 can track which exercises seem to inspire more motivation and/or cooperation from a patient.

(j) Device 100 can provide attention instead of a patient, for example, continuing attention to ensure that a motion once started is carried out. If a mistake occurs, instead of the patient being required to notice it, device 100 can detect the mistake and provide a cue to correct the motion—thereby reducing the mental and cognitive load on the patient.

While motivation and other mental states such as depression and withdrawal may be estimated by a human, in an exemplary embodiment of the invention, they are measured or estimated by device 100 by detecting their effect on performance. In an exemplary embodiment of the invention, device 100 assesses, for example, one or more of: how hard a patient works, how well the patient carries out his task, progress within and between sessions, expected responses to stimuli and/or variability between different tasks and/or along a task.

In one measurement method, a patient's performance on a task is compared to the patient's performance (e.g., range of motion, speed accuracy) in a game. Under the assumption that playing a game increases motivation, differences in performance between a game and an exercise, may indicate the degree of motivation difference between desired and undesired tasks.

In another measurement method, device 100 is used to measure the range of a patient's abilities, for example, ROM (range of motion), pain limit and the like. It is assumed that a diagnosis session can be trusted to provide relatively accurate information about the patient's ability, at least for the reason that the patient knows the diagnosis session is limited in scope. Thereafter, exercises at the edge of the patient's ability are provided to the patient and a determination is made of the number and success of attempts to reach the edge of the range. This determination may be used as an indication of motivation (e.g., willingness to achieve what is known the patient can achieve). In an exemplary embodiment of the invention, the exercise comprises providing performance targets to the patient and the patient is expected to reach for the targets.

In another measurement method, a self-calibrating method, a patient plays a game in which some of the targets are at the range of the patient's ability. As this ability might not be known in advance, a variety of targets of different levels of difficulty, are provided. In an exemplary embodiment of the invention, motivation is assessed by analyzing the game to determine, first, what the patient's abilities are and, second, how often the patient tries to reach the edge of his abilities.

Another method of measurement is tracking how hard a patient works (e.g., how long are rest periods). Another method is determining the hardest a patient works in any particular exercise. Another method is determining if a patient provides attention, involvement and/or activity in a free-play session, where a patient can exercise if he wants to, to any degree of difficulty the patient wants. Attention is optionally determined by comparing trajectories of motion at different times, for example to see the range of variability (e.g., does a patient suddenly slow down—maybe his attention wandered). Involvement is optionally determined by tracking modifications requested by the patient, for example in exercises where a patient can select one of several trajectories.

In an exemplary embodiment of the invention, mental state is estimated by analyzing handwriting or gross motor movements, for example, detecting unusual tremors, ticks or other signs of tension and/or lack of control (e.g., as compared to other times). It should be noted that mental states, in some cases, may be provided as a relative state rarer than absolute values.

Exercises

In an exemplary embodiment of the invention, existing physical rehabilitation exercises are used for device 100. However, various measures can be provided not currently available. In some cases, the exercise is modified to take into account limitations of device 100 or abilities of device 100. Optionally, correct motions are determined with exactitude and/or with a degree of control not possible manually. In addition, some exercises are described herein which are not possible without robot support (or other techniques described herein).

In an exemplary embodiment of the invention, exercises are modified manually. In an exemplary embodiment of the invention, exercises are recorded by a therapist and then annotated (e.g., to mark desired measurements). In another example, exercises are directly programmed into device 100. Optionally, device 100 suggests limitations or additions to exercises, for example, safety limitations or device limitations and/or suggest where a less supportive or more supportive motion mode may be appropriate (for example at an end of a motion a more supportive mode may be advisable).

In an exemplary embodiment of the invention, a reaching exercise is performed by the patient. In such an exercise, various muscle groups can be trained and various levels of difficulty can be provided.

In an exemplary embodiment of the invention, reaching movements are defined by one or more of the following exemplary parameters:

Reach Distance:

Close—touching the body or several inches from the body

Mid—in the mid range from full to close

Far—almost at full arm extension

Reach Direction:

Up/Down—from a lower/higher reach location to a higher/lower location

Out/In—moving away/to the body

Lateral/Proximal—moving out from the body laterally/moving toward the body

Reach height:

Above head

Eye level

Shoulder level

Torso level

Reach target:

Free reach—movement to general location in space with no target

Target reach—movement to a physical target

Simulated target—movement to a target presented on a computer screen

A particular "Reach" is defined by the starting location and the ending location of the hand as defined by its distance, direction, and height. Any reach may also be further understood in terms of the involvement of the arm joints and the ability of the patient to individuate the joints to achieve the reach.

In an exemplary embodiment of the invention, one or more of the following measures is defined:

Ability of the patient to perform the reach;

Smoothness of motion;

Time to achieve the reach end point;

Accuracy of the reach;

Work or power performed;

Comparison of motion trajectory to normal trajectory patterns for reach movements;

Number of repetitions of the reach the patient can perform;

The stability of the performance with subsequent repetitions.

In an exemplary embodiment of the invention, a reach training comprises the following general steps:

5 to 10 repetitions to reach under guided motion. Patient will be instructed to attempt to move with the device 100.

5 to 10 repetitions initiate mode. The magnitude and direction of force of the patient will be measured by device 100. When the threshold for correct intention is exceeded, device 100 will guide the patient to accomplish the reach.

5 to 10 repetitions assisted mode. The patient will attempt to perform the reach independently. Device 100 will measure the intention and assist the patient to move. Over time, the amount of assistance will be reduced as the patient is able to move more independently.

5 to 10 repetitions of free motion. Patient will attempt to perform the reach free of assistance from device 100.

Another exemplary exercise is mimicking of daily activities, such as moving a full cup between points and lifting a book.

Programming

In an exemplary embodiment of the invention, various aspects of a rehabilitation process can be planned and inputted as instructions to a computer (e.g., device 100), including, one or more of:

a) designing a new exercise;

b) modifying an exercise for a particular situation and/or patient;

c) designing and modifying a rehabilitation plan; and d) designing and modifying decision logic (e.g., breakpoints, thresholds and repetitions).

Permissions may be different for different users of system 200 and/or device 100, for example, different permissions may be allowed for one or more of adding new, copy, modify, delete and/or edit. These activities may apply, for example, to one or more of patient data, activity, plan, statistics and/or data logs. Particular activity parameters which may be created and/or modified in accordance with exemplary embodiments of the invention include: trajectories, locations and ranges (e.g., minimum and maximum speed and angles); force parameters, number of repetition cycles, stop decision(s) and/or rest periods length and frequency.

In some embodiments of the invention, one or more libraries are provided as a basis for modification and for storing programs, for example, a plan library, a per-patient library and/or an activity library.

In an exemplary embodiment of the invention, entering a new trajectory is by physically manipulating tip 108 (e.g., by a patient with a good hand or by a therapist). Optionally, the resulting trajectory(s) are then edited on a computer. Alternatively or additionally, a 3D CAD/CAM program may be used, optionally one in which a human body is modeled and various constraints can be placed on movement of points on the body and/or a desired or allowed range of motion for such points defined. Optionally, a graphic design program is used, for example, with a user indicating a few points of a trajectory and the program completing them with a line or a curve. Alternatively or additionally, a user may define various geometrical shapes, such as a circle, for example by providing points and/or a formula. Alternatively or additionally, a user may make a drawing and scan it into system 200 (e.g., at a station 204 or at device 100).

In an exemplary embodiment of the invention, an exercise is calibrated for a particular patient and/or situation. Such calibration may include, for example, one or more of:

a) calibration to patient abilities, such as angular range of motion of a joint or ability to apply force or maintaining fine positional control;

b) calibration to a size of a patient, for example, the length of a limb or a bone;

c) calibration to progress, for example, a plan may have its time span and/or its step size changed based on exhibited or expected progress.

As noted above, a path carried out by a patient or by a therapist may be edited and used for an exercise. In an exemplary embodiment of the invention, editing includes one or more of smoothing, adding points and/or path sections, converting the motion into primitive motions elements, Exemplary Programming Language Table I, below, describes an exemplary high-level programming langue which is optionally used to program device 100, in lieu of learning a robotic programming language. In an exemplary embodiment of the invention, this language is used by the therapist and/or other user. Optionally, existing exercises are storable and modifiable.

This high-level language is based on library of Icons (each representing a command) that can be draged into a program area in order to build (or edit) a program. Each icon represents a command; with 3 types of command defined (more may be added):

a. Motion command—basic motions, such as line and circle.

Each command has start point (P1) and stop point (P2), for every motion command the speed, force acceleration/deceleration time can be set. Setting the points (P1, P2) can be done by pressing the enter key while tip 108 is at the desired point.

b. General command—such as start/stop program, delay and record.

c. Accessories command—a set of command that handle the external devices and accessories that can be attached to device.

Every command has a set of parameters that may be entered (if not, a default parameter value may be used). An operator can add comments to each command. Device 100 generates a description for each command., to every command the operator can add comments, and every command has a description. Not shown are commands for instructing users and parameters which define what behavior device 100 should carry out under certain conditions. Optionally, each path section may include one or more triggers, which, upon activation, execute short sections of code. One example is a trigger activated when a user varies his speed more than 10%, in which case a warning is provided or a more assistive motion mode is provided.

Table II is a sample program, using the language shown in table I. A program structure has several columns; the first one is the main command that are sequential, the second and third columns are for commands which operate in parallel.

When a new program is started, the start and stop commands optionally are provided automatically. Other commands are manually inserted between the start and stop.

Table II is a sample program of a path having 3 straight lines (can be rectangular), with a delay in between, and during the second line an external device is operated (for example— waiting for input from handle). All data during the second and third lines is recorded and the entire program is repeated 5 times. Modifiers for the repetition (e.g., increase speed, increase required accuracy) are optionally provided as parameters. General program parameters, such as type of scoring, expected quality of motion are optionally provided as well.

TABLE I command types

| | | | | | |
|---|---|---|---|---|---|
| Motion commands | Line | Left | p1, p2, F, S, Text | Press @ P1 & press @ P2 | F- force S - Speed |
| | Curve | Left | p1, p2, p3, F, S | Use P1 to start P3 as end & P2 as Via point and curve | system interpolates |
| | Circle/ ellipse | Left | C, R1, R2, F, S, Tex t or P1, P2, P3 | | For ellipse use R2 not 0 |
| | Teach points | Left | P1 . . . Pn, F, S, Text | system interpolates between points | |
| | Teach Path | Left | Path, F, S, Text | System samples path | sample rate |
| General commands | Start | Both | Text | first program command | |
| | stop | both | TXT- Text | end of program | |
| | Delay/Pause | Left | T-Time (second) or B- (button name); TXT N; No. Of | | can be used for waiting on certain button press |
| | Cycle | both | repeated cycles; TXT | | allow to disply No. Of cycles |
| | Record | right | 3 level data accuracy: Normal Fine coarse | Position, force, speed, accelaration,, jerk, I/O state, preload, brake setting | Indicate record mode on/off |
| | analysis | right | | use "eval" command, for example logic may be used with if input | |
| | read input | both | Read (string); TXT | use as input mechnism | |
| Accessories commands | Handle pinch | | Handle 1 pinch (on/Off, force range(kg/Lb)) | | pinch/grip handle |
| | Handle grip | right | Handle 1 grip (on/Off, force range(kg/Lb)) | | pinch/grip handle |
| | wrist motion elbow | | Handle wrist 3x range of force | | wrist handle |

TABLE II program sample

| Prog name | description | date | file name: | | |
|---|---|---|---|---|---|
| trial1 | glass grip | auto date | xxx.prg | | |
| Commands | optional command | optional command | Parameters | comments | |
| 1 | | start | | | |
| 2 | line | | | P1(start point) P2 Force (PA[VALUE]/PP) | PA (value) patient active must exceed force value; PP Patient passive-no force value |
| 3 | delay/pause | | | D(1 sec) | |
| 4 | | handle pinch | record | 1 kg < force <5 kg | display grip force during run if not in range display warning message |
| 5 | line | handle pinch | record | P1 P2 Force (PA[VALUE]/PP) | |
| 6 | delay/pause | handle pinch | record | D(1 sec) | |
| 7 | line | | record | P1, P2(start point) | |
| 8 | cycle | | record | N = 5 | |
| 9 | | stop | | | |

A particular type of control provided in accordance with some embodiments of the invention is spatial programming control. In this type of control, certain gestures or positions in space of tip 108 are translated into commands for device 100. In one example, such gestures may be used by a therapist or by a patient to fast forward past an exercise section.

In another example of a shortcut, wrist movements of a therapist will be translated into arm (or other limb) motions, thus allowing the therapist to make smaller motions and only with his hand, rather than the limb whose motion is being programmed.

Sensing and Control of Limb Position

In device 100, as illustrated, only one point of the patient is controlled, the point in contact with tip 108. However, this means that multiple different arm motions can result in a same spatial trajectory. For some situations this is not a problem. For example, for recovery from stroke, in some cases, any motion is useful. In other rehabilitation scenarios, it is desirable to better dictate or know the positions of all the moving body parts. In some exemplary embodiments of the invention, the position of other body parts is fixed. For example, a patient may be strapped to a chair (e.g., the shoulder of the patient) and/or a rest may be provided for an elbow. This restricts possible motions by a hand holding tip 108.

FIG. 5 illustrates a system 500 including limb position sensing and/or restricting, in accordance with an exemplary embodiment of the invention. Correct motion of other parts of the body than the hand that contacts tip 108 may be provided, for example, by detecting the positions and providing feedback, for example, audio or visual feedback, to the patient.

A patient 506 sits in a chair 514 and uses device 100 (or a device as described below in which the arm is mounted on a ball). One or more cameras 502 image the arm and/or other parts of patient 506 and determine the spatial position and/or velocity thereof. Alternatively or additionally, one or more cameras 516 are mounted on device 100 for such imaging. In some implementation of image based reconstruction of body positions, it is useful to include one or more fiduciary markers 504, for example strap-on patterns or LEDs.

Alternatively to image based position sensing, magnetic, electric, ultrasonic or other contact-less position sensing and orientation sensing methods may be used. Many such position determination methods and devices are known in the art and may be used. In an exemplary embodiment of the invention, a reference position is provided on device 100 and/or on tip 108. Optionally, such position sensors are used for determining the state of device 100, instead of or in addition to mechanical sensors in device 100.

Alternatively or additionally to using contact-less position sensing, mechanical based position sensing, for example using an articulated arm, may be used.

It should be appreciated that in some embodiments of the invention no arm 102 is provided, instead position sensors of some type are used. Feedback is optionally provided via virtual reality type displays and feedback (e.g., vibration to emulate force). However, this may not allow direct force feedback and resistance to be applied, as desired in other exemplary embodiments of the invention.

In an exemplary embodiment of the invention, patches 504 are used to provide feedback or cuing to a patient. In an exemplary embodiment of the invention, a patch includes a wireless receiver, an optional power source and a stimulator, for example a vibrator, pin-prick, a pincher or a heating element. Upon command from device 100, patch 504 can provide a stimulation to the patient. Patch 504 may be wired instead of being wireless.

In an exemplary embodiment of the invention, sensed positions of body points are used for one or more of:

a) determining if a body motion is correct;
b) determining what motions are possible (e.g., based on angles of joints);
c) learning desired motions from an example;
d) monitoring a patient's ability (e.g., for testing or limb measurements); and/or
e) determining if a body posture is correct during, before and/or after exercise and when changes occurred.

Alternatively or additionally to position, orientation and velocity sensors, physiological sensors may be provided, for example one or more of pulse measurement sensors as known in exercise machines and grip and/or pinch force sensors in tip 108. Alternatively or additionally, one or more physiological sensors may be provided on the patient, for example, breath rate sensors.

Referring back to FIG. 5, alternatively or additionally to position sensors, a body rest 508 may be provided for one or more body parts. In the example shown, rest 508, attached to chair 514 by a (optionally adjustable) bar 510 prevents motion of the chest and/or shoulder. In an alternative embodiment, one or more straps are used to hold body parts.

In an exemplary embodiment of the invention, reverse kinematics method are used to estimate the motion and/or dimension of a patient's joints and/or bones. For example, if a limb is fixed to rest 508, movement of tip 108 can be used to estimate the actual motion of the joint. When harness 508 used to lock the elbow is in a fully extended position, the distance from the shoulder to wrist can be calculated as the patient moves the arm. If the handle of FIG. 15F is used and patient is restricted by a shoulder harness then the forearm length can be determined Alternatively or additionally, a force field can be used to restrict the motion in a manner which will guarantee that limb dimension can be determined.

In an exemplary embodiment of the invention, a model of the patient is constructed for use in such reverse kinematics calculation. Also, in safety calculations, such a model may be used. For example, a motion may be prevented as being unsafe if a patient can possibly reach a configuration of joints where the motion is unsafe. The reach of each joint may be dependent, for example, on fixation of the patient (e.g., harnesses), measured ROM and assumed ROM.

Optionally, chair 514 is fixed to device 100, possibly in an adjustable manner, for example, using a fixation bar 512. Optionally, an initial calibration process is carried out, for example when first doing a new activity or during device setup. In one example, bar 512 includes graduations and during calibrations the correct setting of the chair relative to the graduations is determined.

In some embodiments of the invention, device 100 comes with a built-in chair 514. Exemplary positioning of a movable chair is described below.

In an exemplary embodiment of the invention, positioning sensing is to better than 1 cm, 5 mm, 2 mm or 1 mm, over the entire working volume of the device. In some embodiments, a lower absolute positioning accuracy is tolerated if a relative accuracy, within an exercise is maintained.

In an exemplary embodiment of the invention, accuracy of force control is better then 100 gr, 50 gr, 10 gr or better. Optionally, the balancing of the arm is within these values. Similar accuracies may be provided for measurement. Optionally, sampling rate of better than 10 Hz, 50 Hz, 100 Hz or more is provided.

Patient Positioning

In some embodiments of the invention and/or exercises, the patient position is not important. However, in many exercises, correct targeting of a certain joint, tendon and/or muscle group may require precision in motion of tip 108 relative to the patient and/or in the posture of the patient and or other body part.

In an exemplary embodiment of the invention, straps, a harness and/or rest 508 are provided to set the position of the patient. Optionally, one or more bars 512 links chair 514 to device 100. Alternatively to a bar, reference 512 represents a spring-loaded wire, which includes a position sensor to indicate its retraction and thus the position of chair 514 relative to device 100. Optionally, a plurality of retractable wires are used. Optionally, each wire includes a ring into which a leg of chair 514 is placed. Optionally, if the chair moves during a session, the exercises are corrected on the fly to account for the new relative position of chair 514 and device 100. Alternatively or additionally, if motion of the patient is detected during a session, for example motion from one posture to another, the exercises are adapted to reflect the new position. Optionally, a plurality of typical static postures of the patient are learned and the system uses these learned postures to distinguish ongoing motion from semi-permanent postures. Optionally, change in posture is detected by changes in pressure on various pressure sensors, or using cameras which image the chair, device and/or patient. Alternatively or additionally, changes are detected by detecting changes in the actual trajectory followed by tip 108.

Optionally, a mat 518 is provided. In one option, mat 518 is a pressure sensitive mat for detecting positions of chair legs or patient legs. Optionally, calibration is performed for the chair that the patient actually uses. Alternatively or additionally, the mat is used to allow manual entry of relative position. Alternatively or additionally, the mat includes markings that are recognizable by a camera that images the mat.

In an exemplary embodiment of the invention, tip 108 is used to determine the position of chair 514. In one example, once chair 514 is locked in place, tip 108 is used as a digitizer by contacting points on chair 514 and/or the patient. In some cases an adaptor tip may be placed at tip 108. Optionally, once a patient position has been digitized once (e.g., under therapist guidance), next time chair 514 is brought to device 100, tip 108 is moved by device 100 to indicate a desired position of chair 514 or the patient.

Optionally, a laser or light pointer is attached to tip 108 (or other part of arm 108 or device 100) and serves to generate a light marking of a desired location for a chair and/or patient part. Device 100 optionally converts between the coordinate systems of the pointing device, arm 108 and/or chair.

In some embodiments of the invention, it is not tip 108 which has to be at a certain position, but the patient's hand or finger. Optionally, a dummy hand is placed in device 100 and used for such calibration.

Figure 19A:
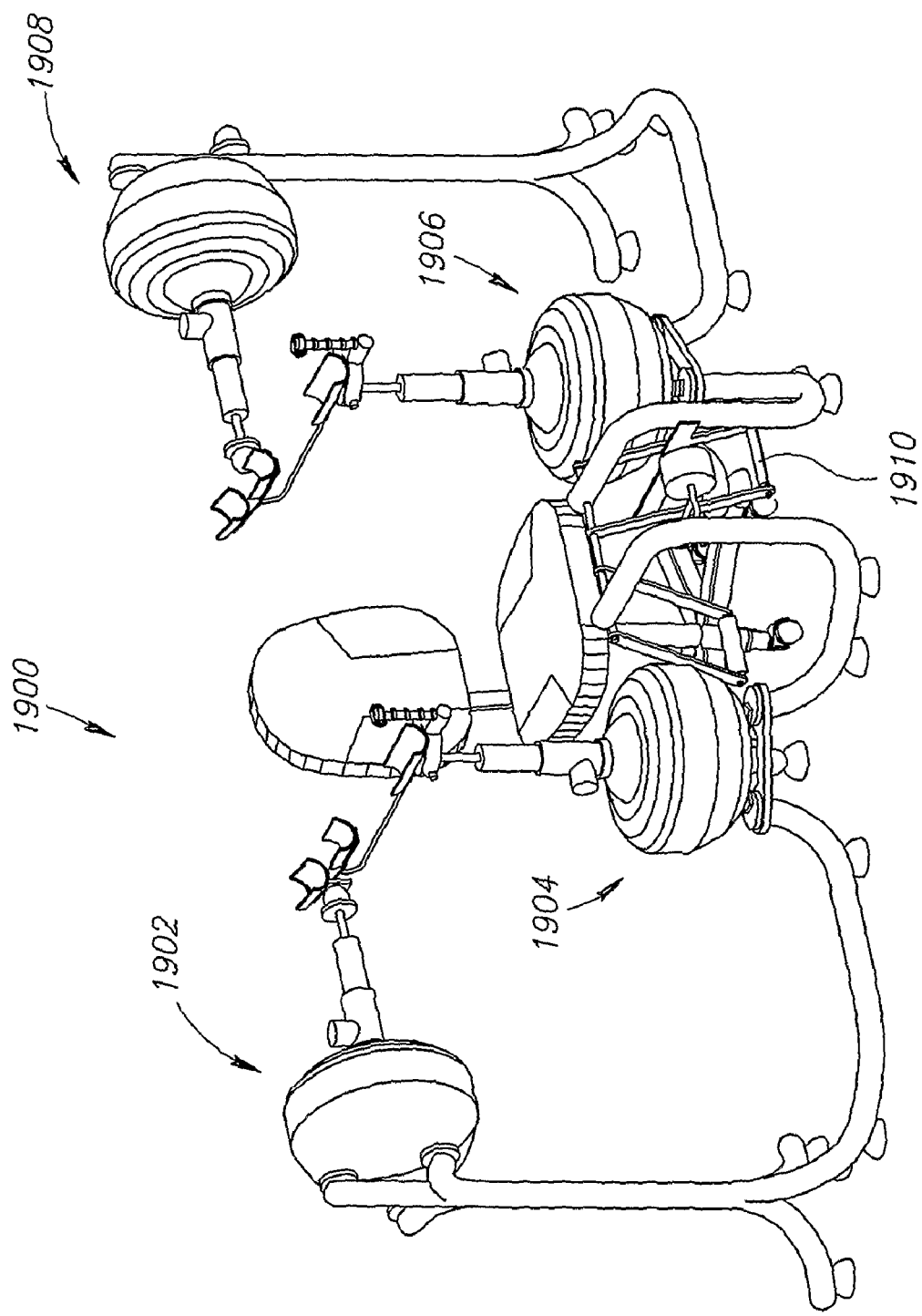
FIG. 19A shows a rehabilitation device for two sides of a body, in accordance with an exemplary embodiment of the invention.
Figure 19B:
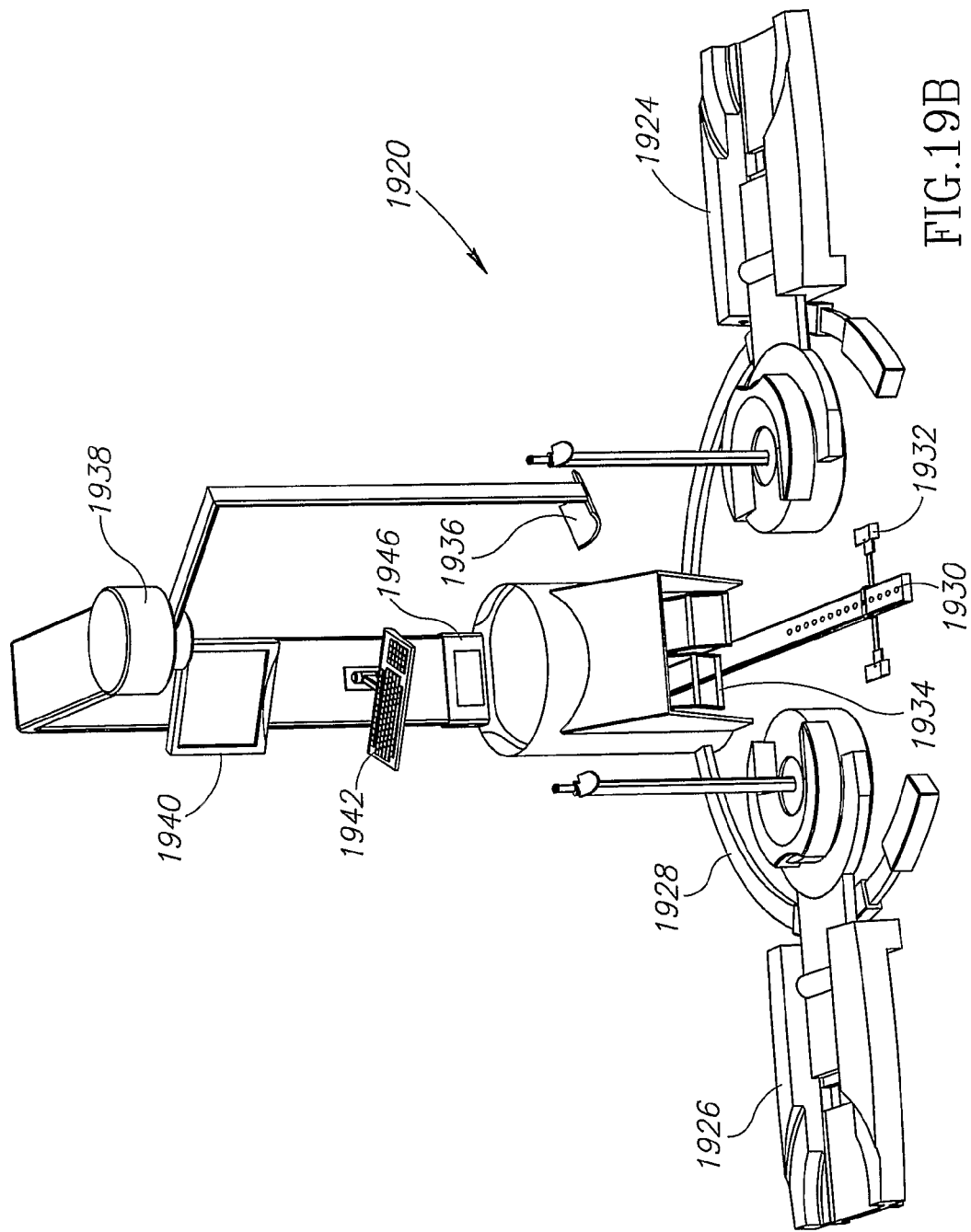
FIG. 19B shows a docking station, in accordance with an exemplary embodiment of the invention.
Figure 19C:
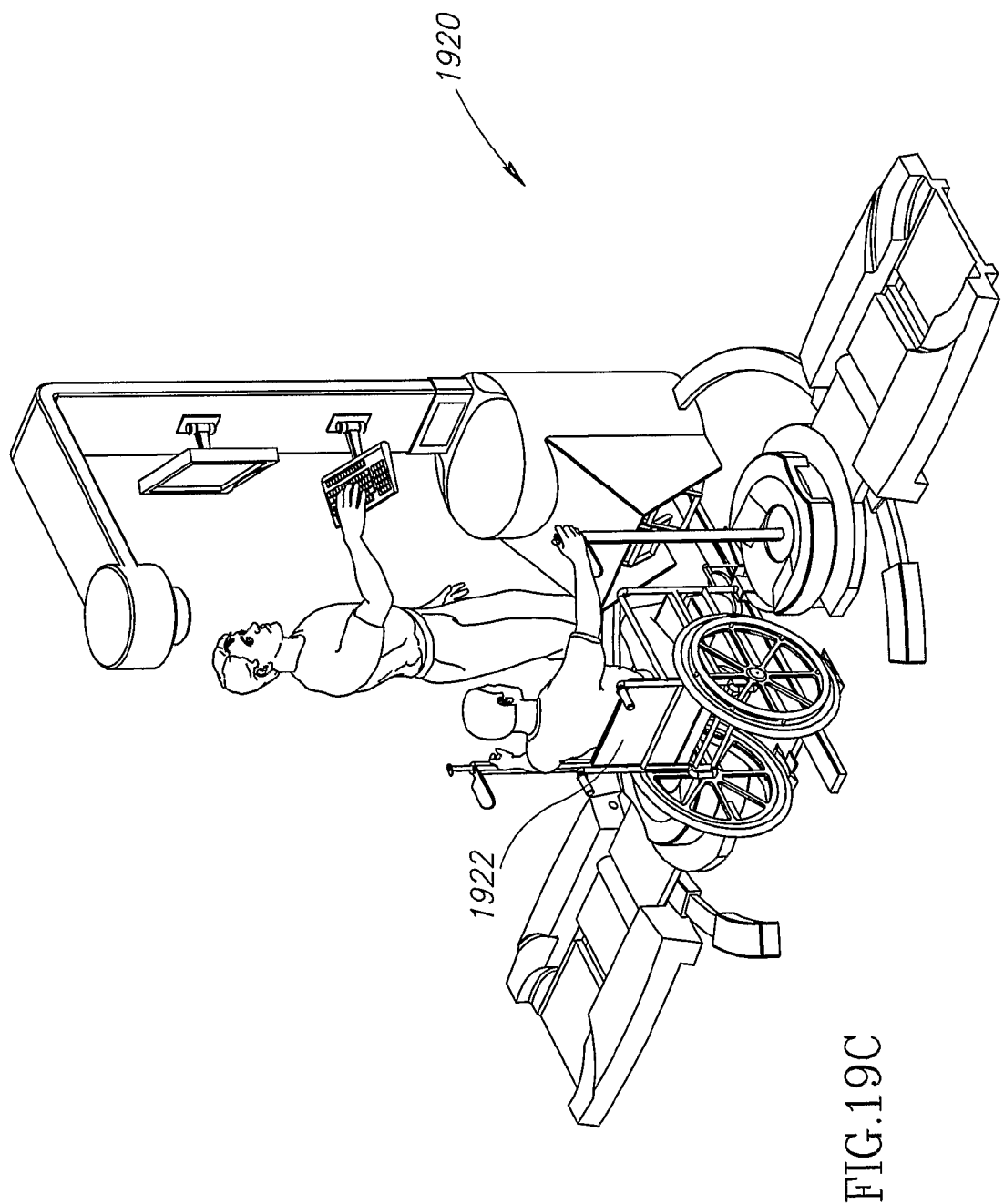
FIG. 19C shows an occupied docking station of the type shown in FIG. 19B.
Figure 19D:
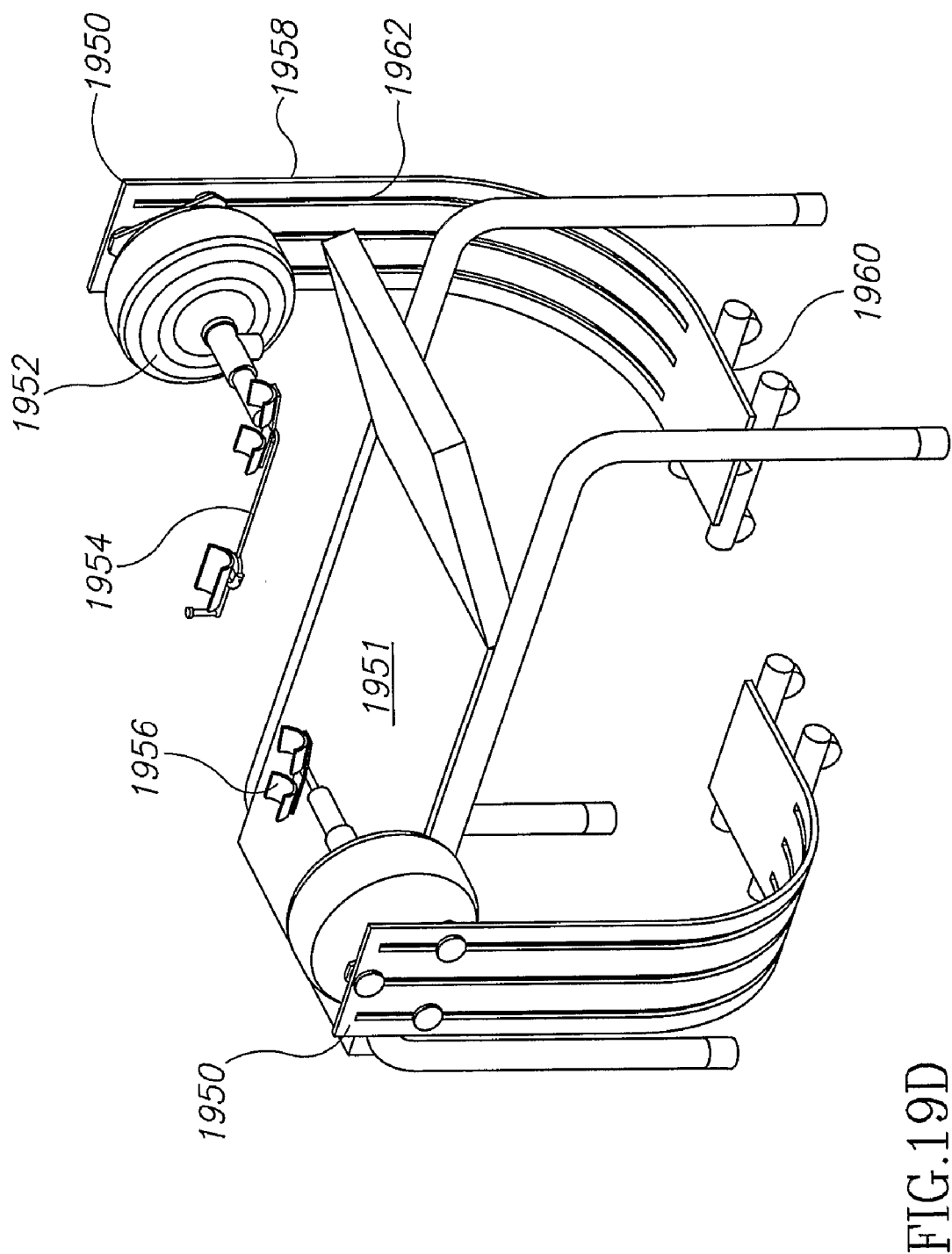
FIG. 19D shows mobile rehabilitation devices positioned near a bed, in accordance with an exemplary embodiment of the invention.
Figure 19E:
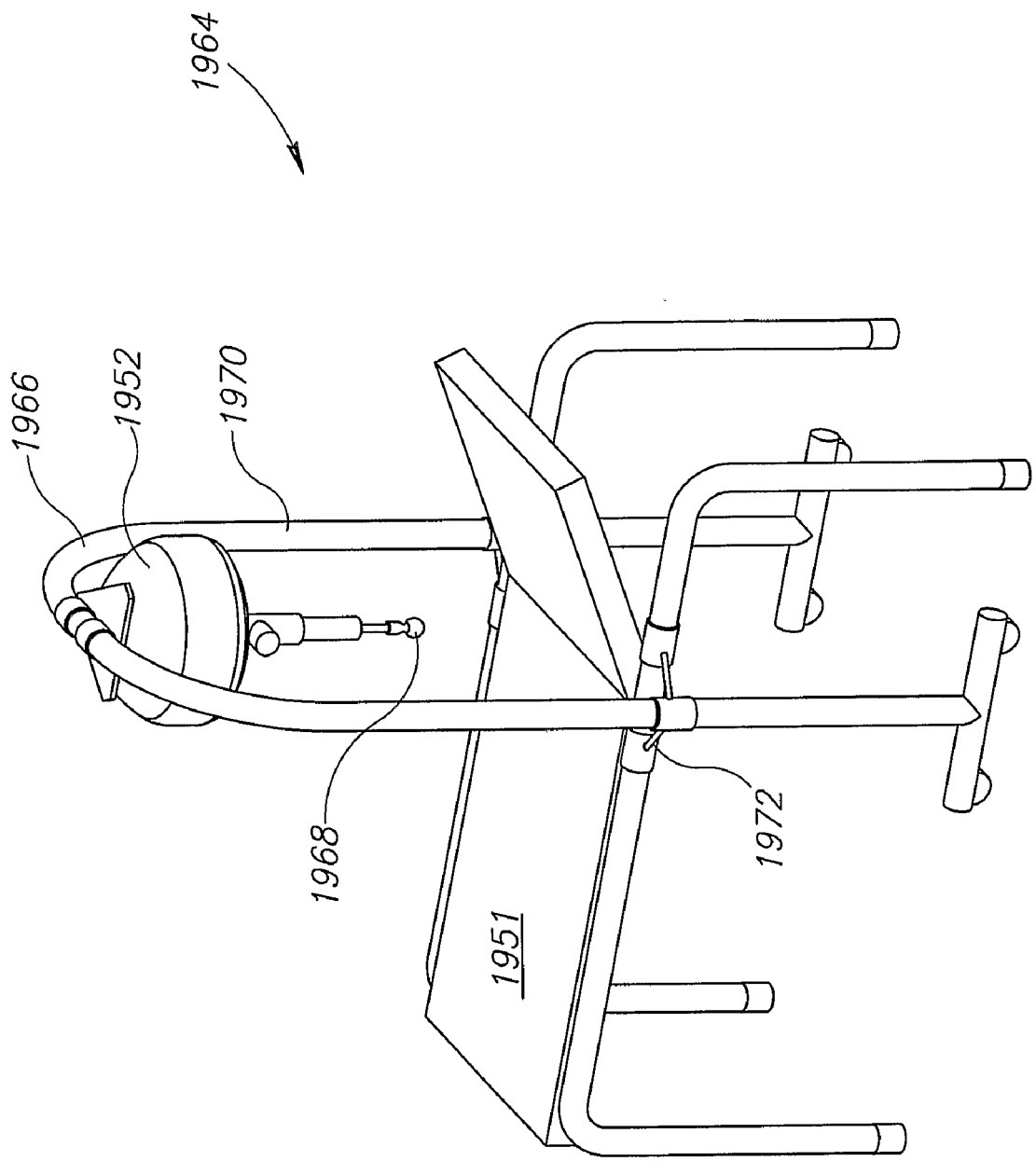
FIG. 19E shows an alternative mobile rehabilitation device, coupled to a bed, in accordance with an exemplary embodiment of the invention.
Figure 19F:
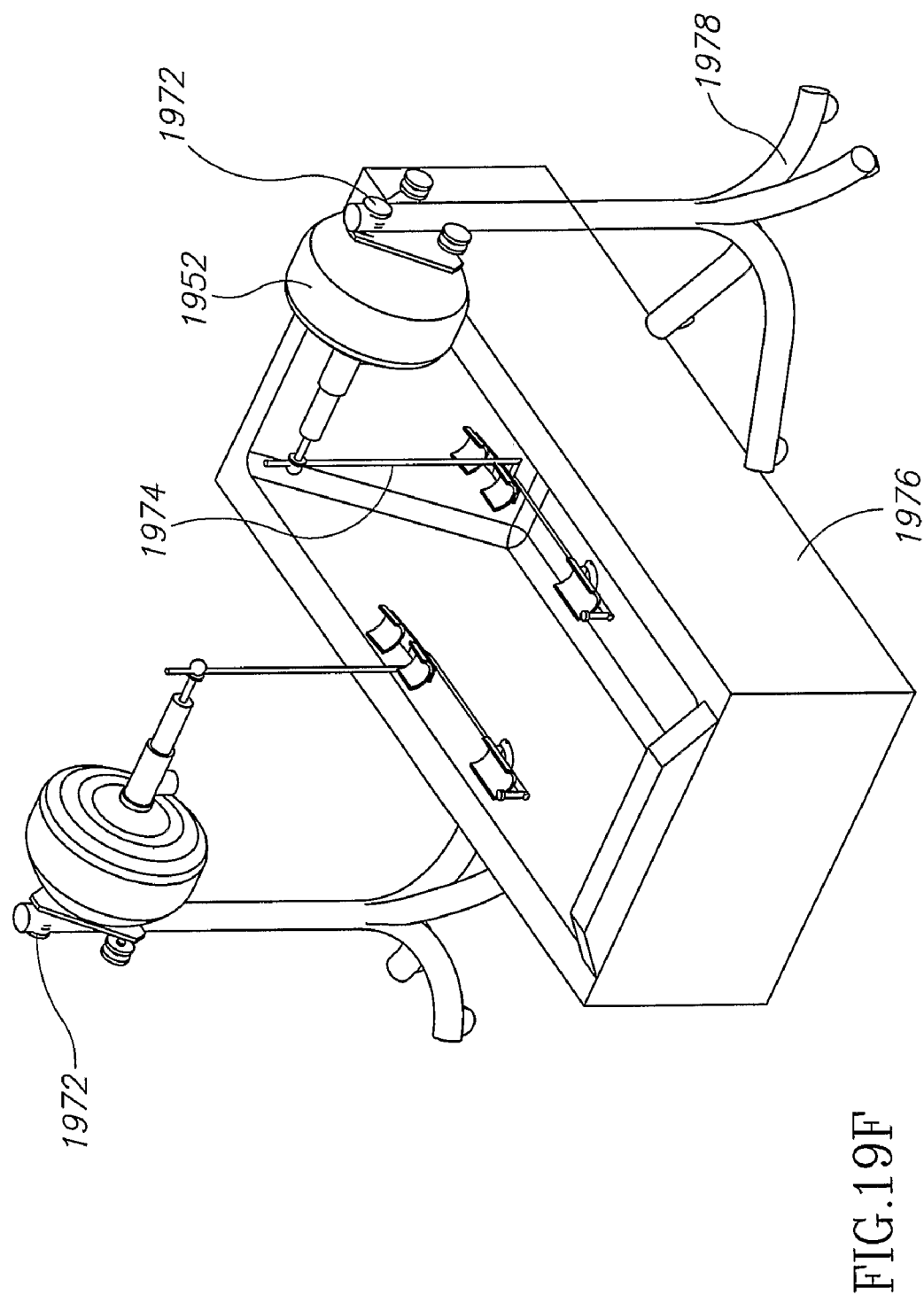
FIG. 19F exemplifies the use of mobile rehabilitation devices in a bathtub, in accordance with an exemplary embodiment of the invention.
Figure 19G:
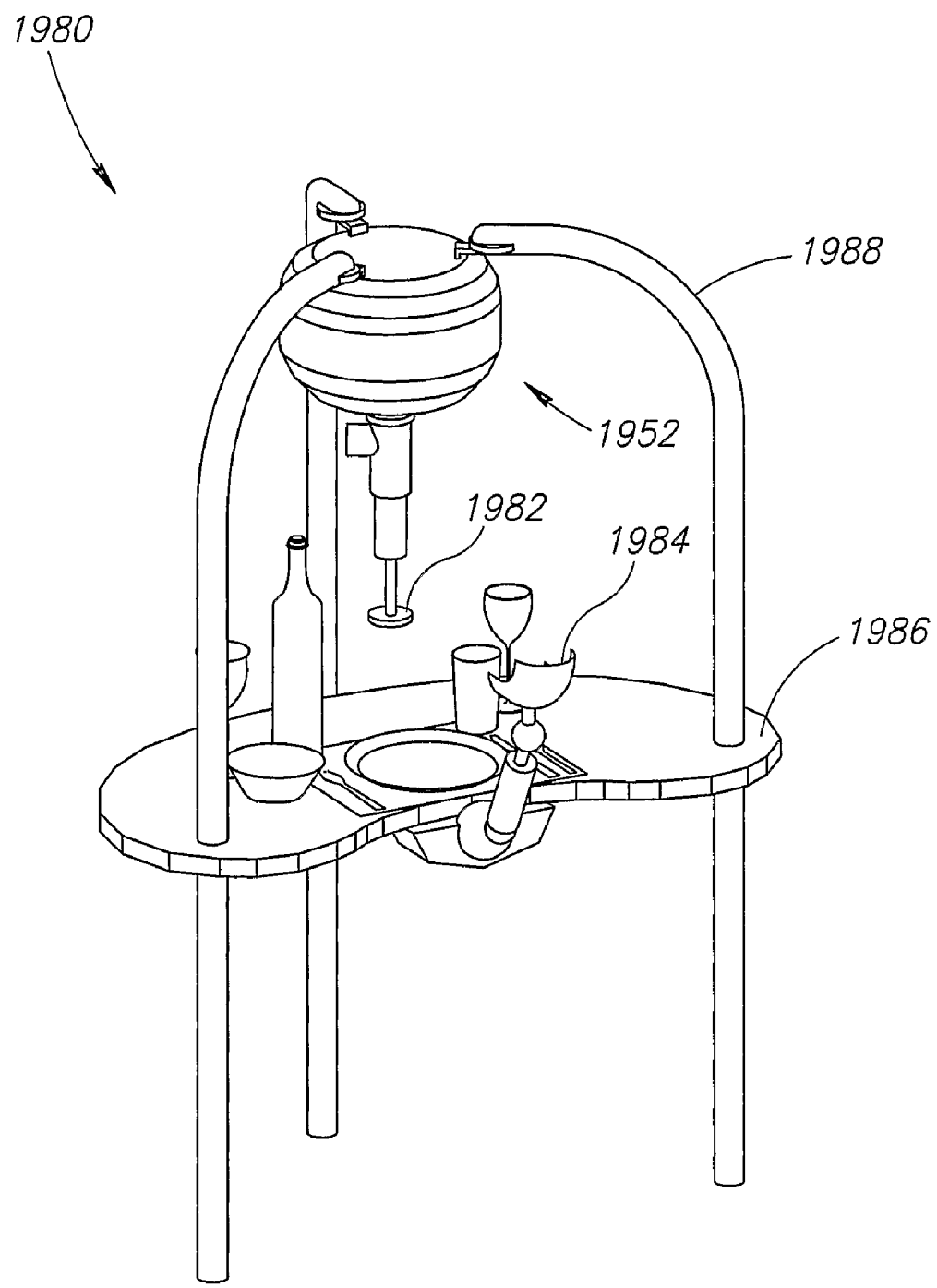
FIG. 19G shows a rehabilitation device configured for use for daily activities, in accordance with an exemplary embodiment of the invention.
Figure 19H:
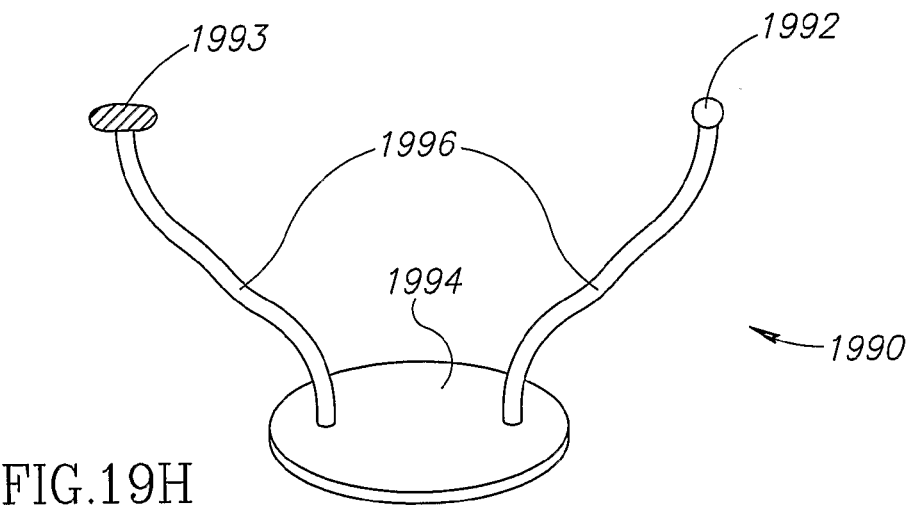
FIG. 19H shows a device for assisting in training for activities of daily living, in accordance with an exemplary embodiment of the invention.

It should be noted that positioning methods as described herein may also be used for positioning other parts of the rehabilitation system, for example, a table, a glass, a second device 100 or a kit for daily living, for example as shown in FIG. 19H.

In an exemplary embodiment of the invention, patient positioning is determined by patient kinematics. In an exemplary embodiment of the invention, once a patient is positioned, the patient performs one or more exercises and the patient position is determined based on the actual trajectories followed. In some cases, a previous ability of the patient, for example, joint range of motion, needs to be known in order to determine the patient position.

In an exemplary embodiment of the invention, the patient performs swinging of the arm, without bending the elbow. The radius of the motion indicates the position of the shoulder joint. If the patient cannot straighten his elbow (or keep it straight) this information is optionally used.

In an exemplary embodiment of the invention, it is assumed that patient movement between sessions is mainly translational motion in a 2D plane, so only one motion of the arm is sufficient for position calibration. Optionally, two arms are moved, to assist in detecting body twist.

Optionally, alternatively or additionally to determining patient position, an initial set of patient movements are used to extract basic information about the patient, such as range of motion and freedom of motion. Optionally, device 100 first applies or suggests a series of exercises meant to warm up muscles and joints, before taking measurements.

Attachment to Body

In FIG. 1, tip 108 is held in a patient's hand. To attach to other parts of the body, other means may be used. In one example, a strap or elastic ring is provided at end 108 instead of a ball-like handle. In another example, a rod-like handle is provided instead of a ball-like handle.

FIG. 6 shows an elbow holder 600, in accordance with an exemplary embodiment of the invention. Such an elbow holder can be used, for example, when the motion required is of the shoulder, so an elbow 616 is what moves along a trajectory. A base 602 is adapted for attachment at tip 108. A hinge 604 allows relative motion between a first part 606 and a second part 608 on which an arm 614 rests. Optional straps 610 and 612 optionally attach arm 614 more firmly to holder 610. Optionally, joint 604 has a varying resistance, for example settable by the patient and/or by device 100. Alternatively or additionally, joint 604 includes an actuator for applying force to close or open elbow 616. Alternatively or additionally, joint 604 includes an angle sensor. Optionally, holder 600 can vibrate the elbow, for example as a therapeutic effect or to help prevent freezing of the joint. Such vibration may be applied to other joints and body parts as well, for example, using suitable attachments.

In an exemplary embodiment of the invention, holder 600 functions as a spastic harness in one example, joint 604 is locked (or is not a joint) and arm 614 is forced open and held by straps 610 and 612.

In an exemplary embodiment of the invention, parts 608 and 606 are raised so that joint 604 has a center of rotation which is substantially the same as elbow 616, in one or more planes.

In other embodiments of the invention, attachment to other points on the body is provided. In particular, it is noted that in some embodiments of the invention, what is constrained is a joint, while in other, what is constrained is a bone or a certain location on a bone. As noted above, various types of constraints can be provided, for example, constraints on angular and/or spatial dimensions. Additional attachments are described with reference to FIG. 16 below.

In an exemplary embodiment of the invention, the attachment includes a coded circuit or other means so that when attached to arm 102, device 100 is aware of the type of attachment.

In some embodiments, the attachment is fitted with a quick connecting elements made out of two mechanical quick connect parts (e.g., spring loaded pin and slot arrangement) and an electrical quick connect (e.g., spring loaded small needle contacts), this allows a fast change over from exercise to exercise or from patient to patient. In an exemplary embodiment of the invention, each attachment includes a chip and receives power form the connector and sends data (if any) on a bus, for example a packet-type bus. Alternatively, the electrical connector is used to directly interface measurement means (e.g., a potentiometer) of the attachment, to device 100.

Instructing of User

Device 100 can provide instructions to a user in many modes, including, one or more of (for various embodiments of the invention):

a) recorded speech.

b) computer animation display.

c) instruction videos.

d) motion of device 100, while patient is not attached.

e) motion of device 100 while patient is attached, possibly at a slower speed and with commentary.

f) motion of device 100, with a dummy attached.

g) using musical notes, for example as cues or to set a tempo of motion.

h) motion of a second device 100, for example as a demonstration or in sequence with the patient's own motion.

Training, Teaching and Quality of Motion (QoM)

While one part of a rehabilitation plan is often exercising a body part to maintaining or increase strength or range of motion, in an exemplary embodiment of the invention, rehabilitation includes teaching a patient quality aspects of motions and/or what motions are correct.

In an exemplary embodiment of the invention, one or more of the following qualities of a motion are of interest:

a) degree of utilization of available joints and/or joint range of motion;

b) usage of muscles where they can apply sufficient force;

c) motion where joints and/or muscles can achieve a better accuracy of control;

d) motion which does not approach thresholds of ability;

e) motion which does not approach danger areas (for example for a patient with unstable joints);

f) smoothness in motion and/or rotation;

g) distance traveled;

h) maximum force required;

i) spatial and/or energy efficiency of motion, e.g., extra motions; and/or j) motion with minimum jerk In an exemplary embodiment of the invention, quality of motion is judged using a power law, which characterizes motions by healthy individuals. Paretic individuals are optionally characterized as to how closely they reach this law and for which joints and/or motion types it is reached.

Optionally, 'Healthy movement' is described by basic kinematic characteristics that define quality of motion. For the arm, one such characteristic is a smooth transition of the hand from one point to another following roughly the shortest path between the two points. A second characteristic is that the velocity of the hand is constrained by the curvature of the path (Viviani P, and Terzuolo C. Trajectory determines movement dynamics. J Neurosci 7, 1982: 431-437, the disclosure of which is incorporated herein by reference). The larger the curvature of the path, the slower the movement of the hand is, at a constant ratio of 2/3. These kinematic descriptions are defined mathematically, and thus, they can be used for an objective quantification of the quality of movement.

A "Minimum Jerk" can explain the smooth and shortest movement characteristics often observed in healthy people, while the "Two-thirds Power law" has been developed to validate the relation between path curvature and hand speed. More recently, both rules have been unified (Viviani P, and Flash F. Minimum-jerk, two-thirds power law, and isochrony: converging approaches to movement planning. J Exp Psychol: Hum Percept Perform 17: 32-53, 1995, the disclosure of which is incorporated herein by reference) and mathematically defined as two aspects of the same intention (Richardson M J E, and Flash T. Comparing smooth arm movements with the Two-Thirds Power Law and the related segmented-control hypothesis. J Neurosci 22: 8201-8211, 2002, the disclosure of which is incorporated herein by reference). These two rules combined in one single description can be adopted for testing quality of movement before, during and/or after treatment with device 100. Optionally, power law fitting is determined by providing the patient with a range of motions, at different speeds and extracting power-law information from the results. The law may be applied to other joints and limbs, such as lower limbs.

Another law which may be applied relates to the relative motion of each joint in a coordinated motion. In healthy persons such motion takes into account the relative distances of the various joints from the target of motion and the different accuracies of such joints. Another law which may be applied is Fits law which relates a size of target to a time to hit the target.

These qualities may be general for a motion or particular for a patient with certain abilities and lacks.

In an exemplary embodiment of the invention, such qualities of a motion are taught to a patient by example, for example, leading an arm through correct and incorrect motions. Such motions may be entered for example by the therapist or by the patient or be pre-programmed. Alternatively or additionally, a patient motion is recorded and corrected and then the patient is paced through the incorrect and the corrected motions. In a pre-defined motion, the motion may be calibrated for the particular user, for example for the user's size.

Optionally, a threshold of correctness is defined, for a patient to attempt to keep all his motions as being of a quality (in one or more parameters) above the threshold.

Alternatively or additionally, such qualities are taught by a commenting in real-time or off-line on a patient's motions.

Thus, in some embodiments of the invention, a substantial part of rehabilitation comprises exercising a patient in motions which are correct or teaching the patient how to know if a certain motion he has performed is of a higher or of a lower quality.

Other types of training are not related to motion correctness. For example, a patient may be trained to not ignore a damaged limb. In a related aspect, however, a patient may be trained to use a damaged joint as part of "correct" motion, so as not to reduce a range of motion of the joint.

In one example, the relative motion expected between an elbow and a wrist is known (e.g., or is inputted by a therapist, such as by example) for certain motions, such as moving objects on a table surface. If a patient deviates by a certain amount (e.g., defined by the therapist) feedback is provided.

Paired Motion

In an exemplary embodiment of the invention, motion with a good arm limb is used to train a bad limb. For example, a good arm can be used to trace a circle and then the bad arm is trained to trace the circle. One advantage of such training is the intimate feedback that a patient receives by better understanding exactly which joints and muscles are used for each motion. In an alternative application, the "good" motion is provided by a therapist or other caregiver.

In a single arm device 100, the following process may be used:

a) Device 100 optionally illustrates a correct motion, in actuality or on a display.

b) A motion is executed with a "good" limb. Optionally, the motion is corrected, using methods as described above for editing.

c) The motion is repeated with a "bad" limb, for example using passive motion, free motion or a force field. Optionally, the "good" motion is corrected before being applied to the bad limb, for example, an expected speed reduced, a range of motion reduced or a force reduced.

d) Feedback is provided to the patient during and/or after the motion (e.g., as a display).

e) The motion is optionally repeated.

Figure 7:
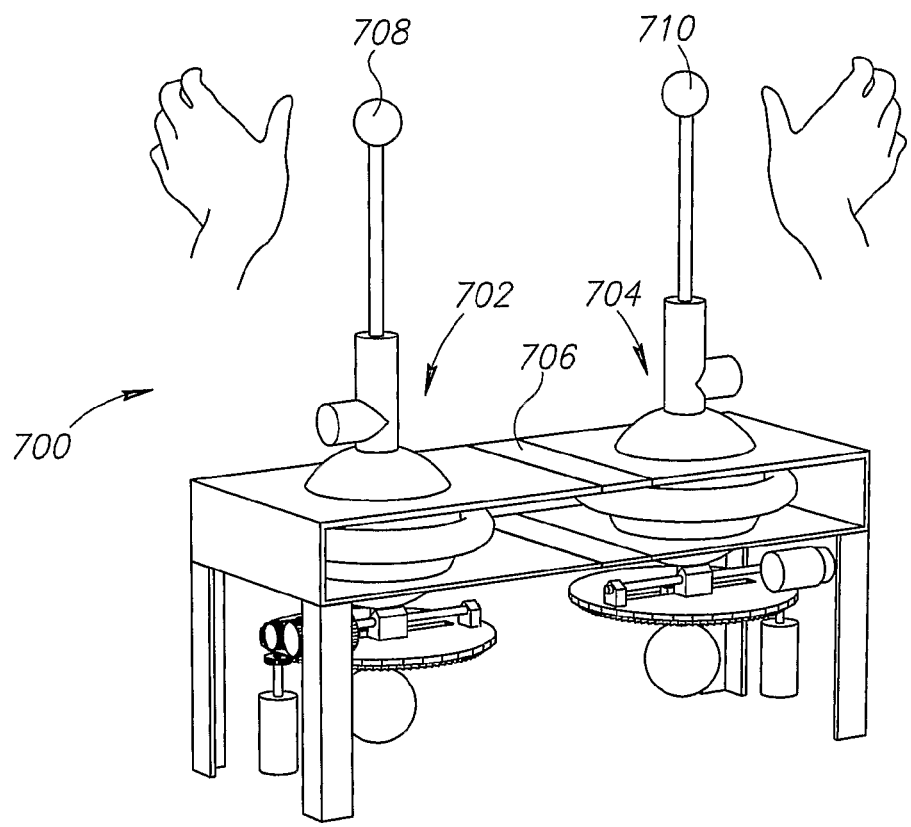
FIGS. 7 and 8 illustrate two hand rehabilitation devices, in accordance with exemplary embodiments of the invention.
Figure 8:
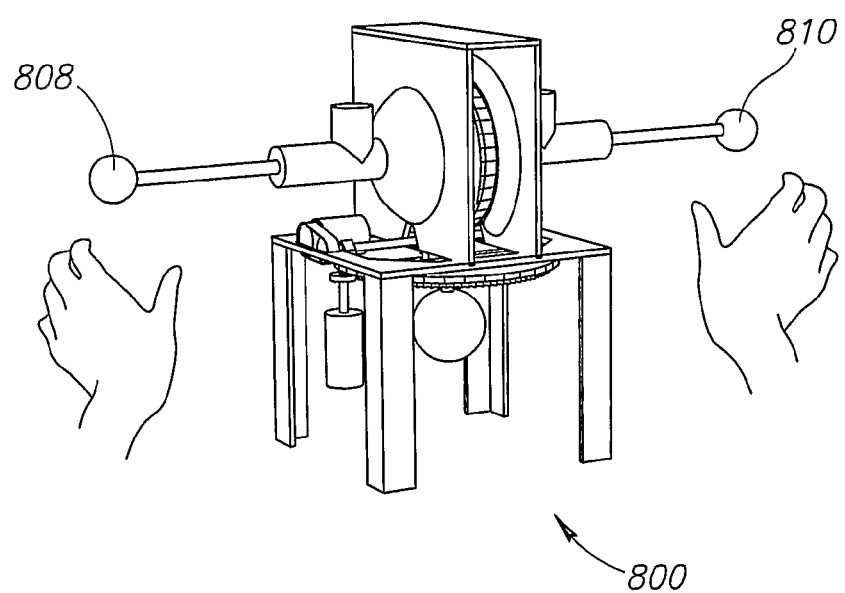

FIG. 7 and FIG. 8 shows two handle devices 700 and 800 respectively, in which two arms can be moved simultaneously, with optional coupling. In an exemplary embodiment of the invention, this is used to have one arm passively move the other arm, for example so the patient can sense with the good arm what a bad arm is doing, or vice versa. Alternatively or additionally, one handle is moved by the device, so the patient can see what is expected of him. Optionally, two arm devices are used for children, for example as a game between paretic children and healthy children or grownups.

In device 700, two separate rehabilitation devices 702 and 704 are optionally attached by a base 706 and coupled by computer, electrically and/or mechanically, so that an arm 708 of one mimics the motion of an arm 710 of the other. The arm moving mechanism is optionally a ball based mechanism as described below.

In device 800, a single joint links two arms 808 and 810. As a result, the motions are reversed. Optionally, arms 808 and 810 are extendible (as described below, for example) and are linked together so that they both lengthen and shorten together, for example, the two arms including extensions that are engaged on opposite sides of a gear with a fixed center of rotation (e.g., a rack and pinion mechanism).

In an exemplary embodiment of the invention, mirrored motion is provided using other devices. For example, in an application using standard devices, mirrored motion is provided by a user holding one mouse in either hand (or in a same hand sequentially) and applying the above transfer of motion form one hand to the other. In another embodiment, one or two force-feedback joysticks are used. It should be noted that for this and other embodiments a plurality of devices may be used. In particular, for specific applications, relatively simple and/or standard hardware can be used, for example force feedback joysticks or haptic displays.

Complex Motion

Figure 9A:
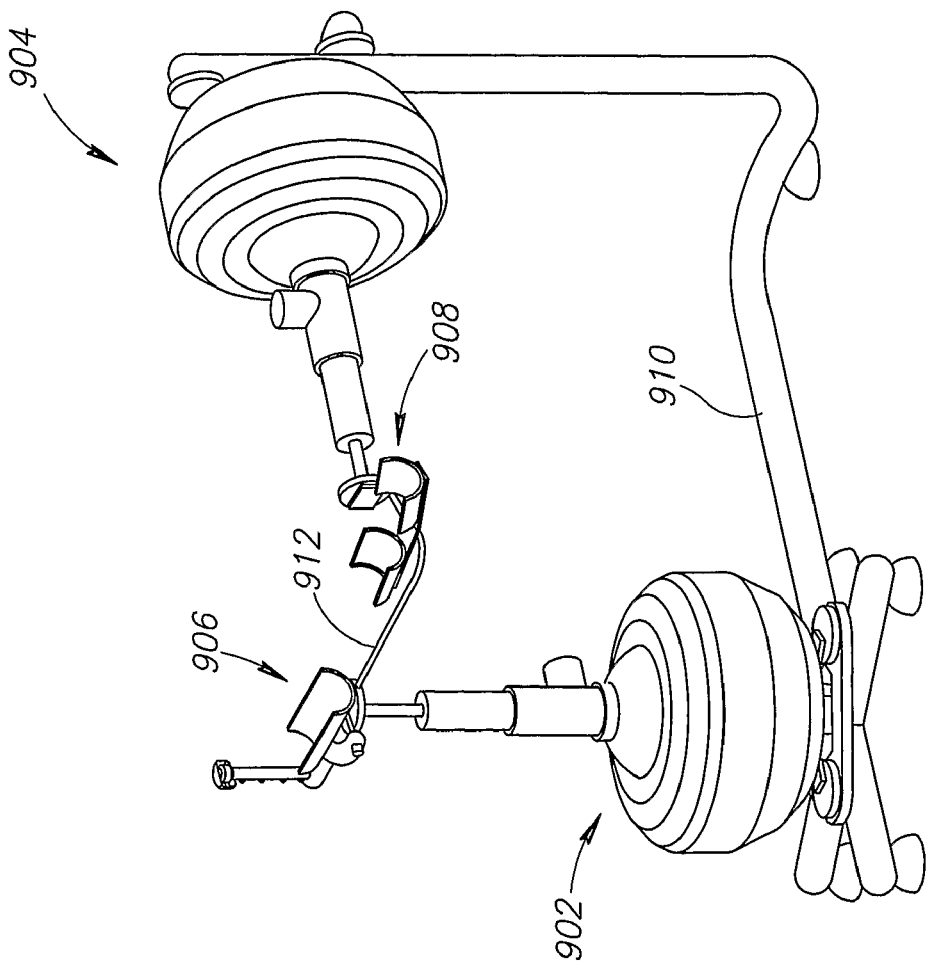
FIGS. 9A and 9B illustrate devices for controlled motion of more than one point in a body, in accordance with exemplary embodiments of the invention.

FIG. 9A illustrates a rehabilitation device 900 comprising two sections, a first section 902 associated with motion of a wrist and a second section 904 associated with motion of an elbow. Sections 902 and 904 can be ball-based devices as described below. A rigid and optionally adjustable connection 910 fixes the relative position of sections 902 and 904. A connection 912 optionally interconnects a wrist holder 906 and an elbow holder 908. Device 900 is used to exemplify control of multiple points on a limb (e.g., arm or leg) during rehabilitation.

In use, each of holders 908 and 906 can be controlled in three spatial dimensions and optionally in angular dimensions as well, thus allowing more complex motions to be tested, trained and/or provided. Optionally, the possibility of restricting certain motions is useful from a safety point of view, for example, preventing certain rotations of the joints. Optionally, a point is controlled in 3, 4, 5, or 6 degrees of freedom of motion. Optionally, the control in some of the degrees of freedom is different than in others. For example, motion in one axis may have resistance associated therewith, while an angular motion may be assisted motion with device 900 supplying some of the force.

It should be noted that in device 900, trajectories may be defined as relative trajectories in which the actual position of the device 900 is less important than the relative positions and movement in space of holders 906 and 908.

Figure 9B:
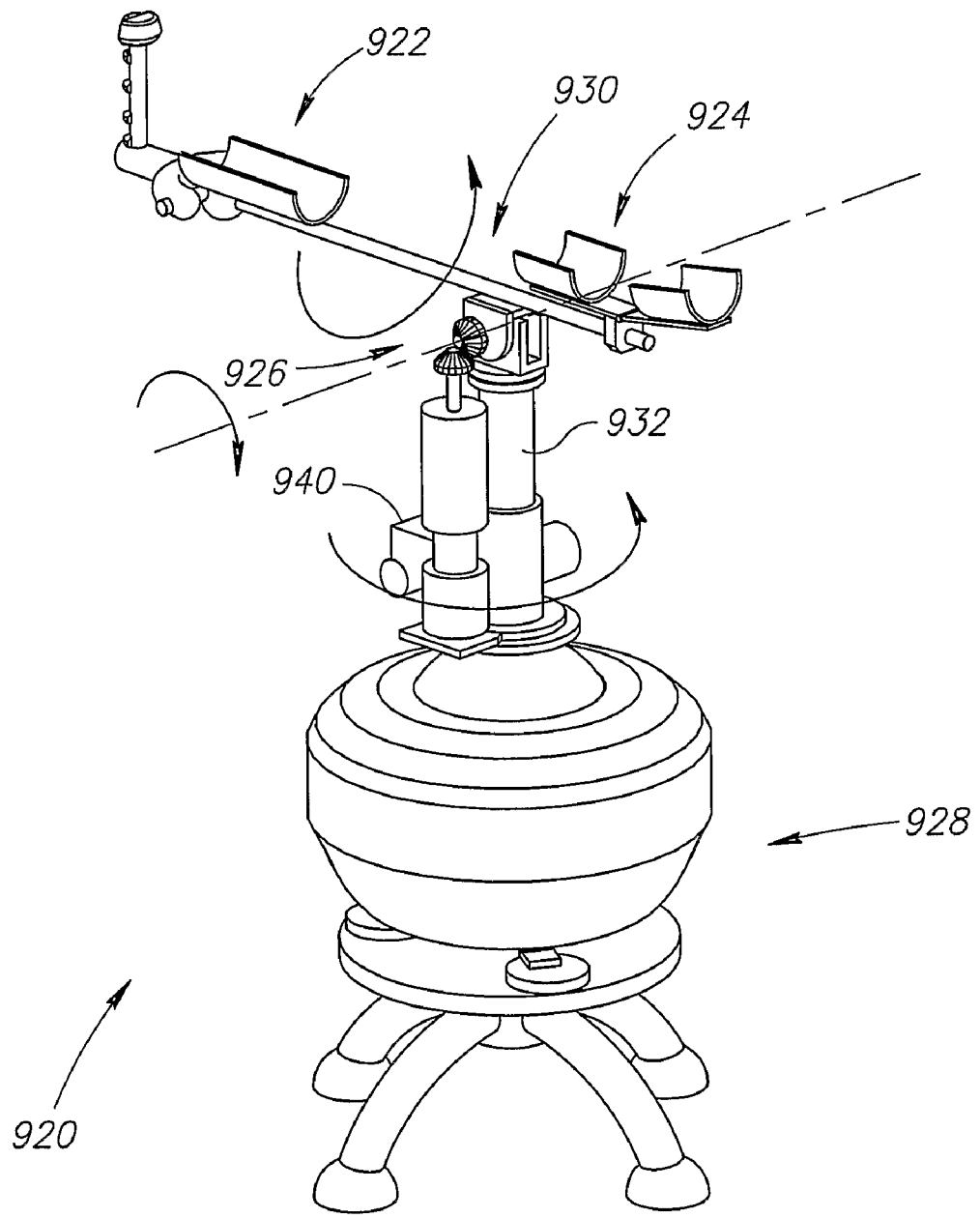

FIG. 9B illustrates a rehabilitation device 920, including a single section 928 with an arm 932, on which is mounted an arm holder 930. Holder 930 restrains both an elbow using an elbow holder 924 and a wrist, using a wrist holder 922. An optional rotation mechanism 926 is shown for rotating holder 930 perpendicular to arm 932 while an optional rotation mechanism 940 rotates holder 930 around arm 932. Alternatively or additionally, a similar mechanism (not shown) is optionally provided for rotating holder 930 around its axis.

As will be described below, another type of complex motion which can be supported by a rehabilitation device in accordance with an exemplary embodiment of the invention requires synchronized motion of several body parts, for example, an arm and a leg.

Ball-Based Device

As noted above, designs other than an articulated arm may be used for device 100. In particular, in an exemplary embodiment of the invention, the device is based on a universal joint, from which extends a rigid arm, which is optionally changeable in length.

Figure 10:
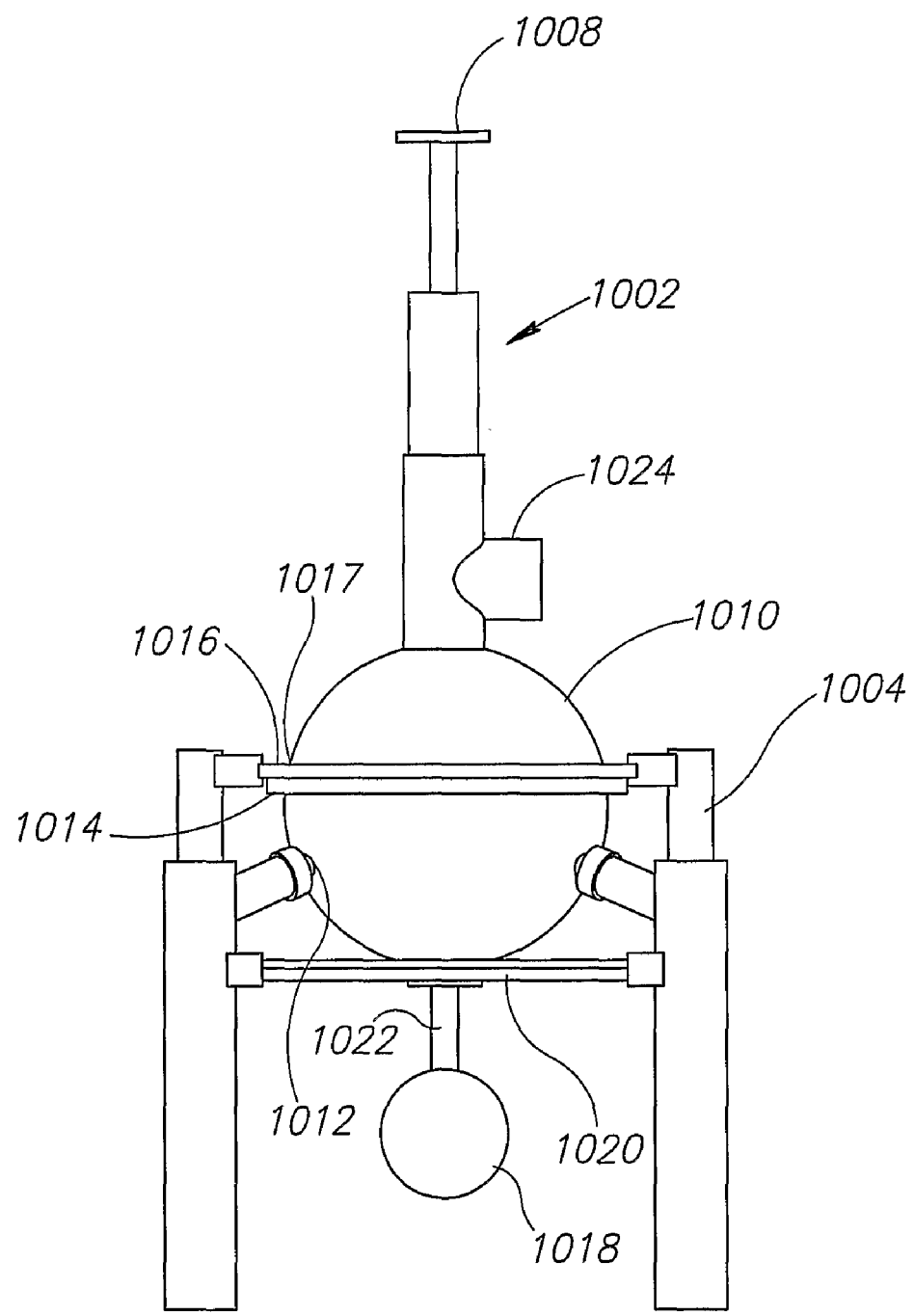
FIG. 10 shows a ball-based rehabilitation device, in accordance with an exemplary embodiment of the invention.

In an exemplary embodiment of the invention, the universal joint is implemented as a ball in socket joint. FIG. 10 shows an exemplary rehabilitation device 1000, using a ball-in-socket joint. This reference number is used in the general sense for several ball-based devices as described herein, for conciseness.

Device 1000 comprises a base 1004, for example a table containing a plate 1016, with an aperture 1017 defined therein and enclosing a ball 1010. Ball 1010 optionally rests on a plurality of rollers 1012. In an alternative embodiment shown in FIG. 11, rollers 1012 are replaced by a bottom plate 1015 with an aperture 1013 defined therein which supports ball 1010.

An arm 1002 extends from ball 1010 and is optionally balanced by a counter-weight 1018 attached by a rod 1022 to an opposite side of ball 1010. Rod 1022 optionally passes through a slot in an optional guide plate 1020, described in greater detail below.

In use, ball 1010 turns and/or rotates, allowing a tip 1008 of arm 1002 to define various trajectories in space. Optionally, arm 1002 is extendible, so that the trajectories fill a volume of space. Optionally, arm 1002 includes a motor or brake 1024 (e.g., an oil brake), to actively move or passively resist such extension.

In an exemplary embodiment of the invention, a brake 1014 is provided for ball 1010. One potential benefit of using a relatively large ball 1010 is that torque at the surface of the ball, for example as required for braking or moving arm 1002 is generally smaller than required for smaller joints, possibly allowing the use of smaller or cheaper motors or other mechanical elements. Alternatively or additionally, positional control of such motors and/or sensitivity of position sensors can be smaller, while still allowing for sufficiently precise control and feedback.

Device 1000 can be provided in various configurations. In a simplest configuration, the device is completely passive and a user can merely set plate settings (described below) and resistance settings on the brakes. In a more advanced configuration, resistance can be varied in real-time by a computer control. In another advanced configuration, sensing of ball and/or arm position is provided (e.g., using sensors, not shown). In another advanced configuration, directional resistance can be varied (e.g., using a directional brake, not shown). In another advanced configuration, motive force, optionally directional can be set or varied, for example using a plate and/or using multiple directional motors (which can also be used to provide resistance).

In an exemplary embodiment of the invention, multiple motors are used to control motion and/or force of arm 1002. The motors optionally include optical position encoders, to determine an arm position. Alternatively or additionally, stepper motors or servo motors are used. Alternatively or additionally, a separate sensor, for example, one which reads optical markings off of ball 1010, is used. In an exemplary embodiment of the invention, rollers 1012 are replaced by motors which rotate wheels. If one wheel is in a direction (relative to the surface of ball 1010) perpendicular to another such wheel, selective motion in one or both directions can be achieved (e.g., if motion perpendicular to the wheel is low-friction slipping motion). Alternatively, only one roller is replaced by a motor with a turning wheel, wherein the wheel is turned to a direction of motion desired and then rotated to achieve the motion. Directional resistance is optionally achieved using the motor. Alternatively, such resistance is achieved by a combination of the motor applying force or resistance and a general resistance applied by brake 1014. Optionally, one or more strain sensors are provided or integrated in the motor(s), to assess a direction of force being applied to arm 1002. Then, the motors can respond with a counter-force, or an assisting force or a diverting force (e.g., with a component perpendicular to the applied force), as required.

In an exemplary embodiment of the invention, brake 1014 is operated by raising and lowering the brake towards the equator of ball 1010, when the brake has an inner diameter of less than that of the ball. Alternatively, the brake is inflated and deflated as needed. Alternatively or additionally, a circumference of the brake is modified, for example, by it being formed of shape memory alloys which are heated to cause momentary expansion and/or shrinkage of the brake. Alternatively or additionally, a perpendicular brake is used which is pressed onto the surface of ball 1010 and towards the center thereof.

Alternatively or additionally to a unidirectional brake, directional brakes may be used, for example, rubber blades-like pads which resist motion of the ball along the blade by bend with relatively low friction to allow motion perpendicular to the blade.

It should be noted that when arm 1002 is extendible, forces applied to point 1008 generally include also a component along the axis of arm 1002, to which brake or motor 1024 may respond and which is optionally taken into account in the response of ball 1010.

Balance

Figure 11:
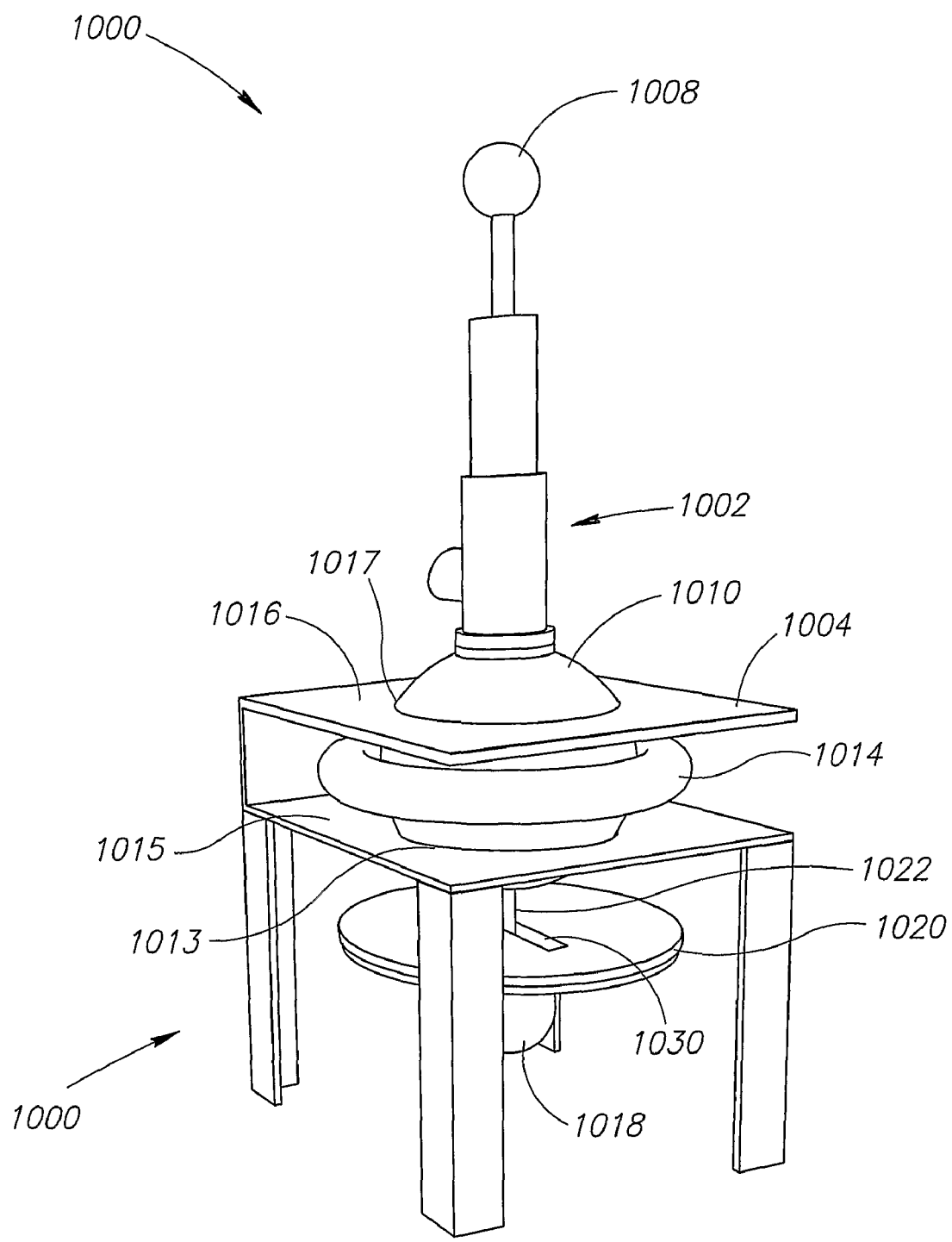
FIG. 11 shows a balancing of the rehabilitation device of FIG. 10, in accordance with an exemplary embodiment of the invention.

FIG. 11 shows a balancing of device 1000, in accordance with an exemplary embodiment of the invention. As noted above, FIG. 11 shows a variant of device 1000, in which ball 1010 is supported by plate 1015. Weight 1018 is optionally designed to exactly cancel the moment of arm 1002. Alternatively, it may be designed, or modified (e.g., by changing its distance from ball 1010 or by adding or removing a modular weight), to provide a force which return arm 1002 to a resting position or a force which tends to move it away from such a resting position. In some cases, balancing may be adjusted to correct for a weight of an attachment, or of the patient's limb.

Optionally, when arm 1002 is extendible, the extending part includes a moving counter-weight that extends away from the center of ball 1010 in a manner which maintains the center of gravity of ball 1010. This motion may be solely inside of ball 1010.

Alternatively or additionally, balancing of ball 1010 is provided by active balancing by the motors and/or brakes. Such active balancing may also be used to effectively reduce or cancel out the moment of inertia of ball 1010 and arm 1002.

When an attachment is added to tip 1008, this may change the balancing. Optionally, a suitable weight is provided with each such adjustment, for adding to balancing weight 1018. Alternatively, handle 1008 includes one or more contacts and/or circuitry which match one or more contacts or circuitry in a mating part of the attachment. This allows device 1000 to detect which attachment is being added and suitably move weight 1018 to compensate. Suitable tables are optionally downloaded from a remote site. Alternatively, the attachment includes a peg of suitable length which pushes into tip 1008 and thereby moves an arm balancing weight inside of ball 1010. Movement of weight 1018 is optionally by a motor (not shown) and may be, for example, along a rod 1022 and/or away from a line connecting rod 1022 and arm 1002. Alternatively or additionally, device 1000 self calibrates by detecting an applied torque moment and moving weight 1018 (or other weights) to compensate.

Optionally, the balancing is designed relative to an expected weight or force applied by a person during an activity.

FIG. 11 also shows rod 1022 being constrained to travel in a straight line by a slot 1030 in plate 1020.

Guide Plate

While, in general, computer controlled directional motors and brakes can achieve any desired motion, in some embodiments of the invention, a possibly more limited motion is supported by the use of plate 1020 and its associated slots 1030. A potential advantage of using guide plates is that movement perpendicular to the slot is not generally possibly, and this does not required suitable circuitry.

Figure 12:
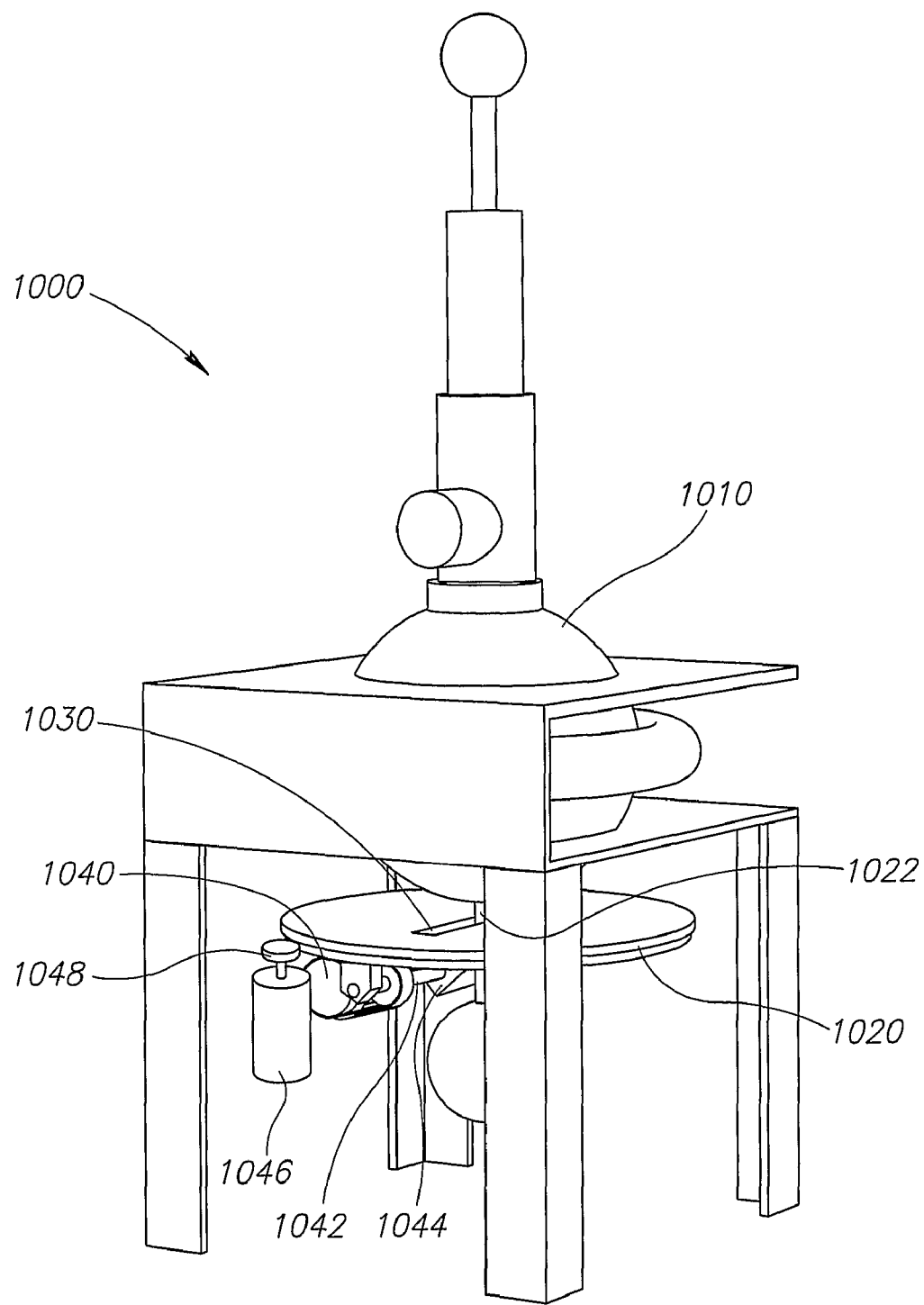
FIG. 12 illustrates a drive system for a plate-based rehabilitation device, in accordance with an exemplary embodiment of the invention.

FIG. 12 illustrates a drive system for a plate-based rehabilitation device, in accordance with an exemplary embodiment of the invention. A first, optional, motor 1046 is attached to a gear 1048 which rotates plate 1020 to allow motion of rod 1022 in other than a straight line. A second, optional motor 1040 is attached to a threaded rod 1042 on which a rod coupler 1044 travels. As coupler 1044 travels, it moves (or resists) rod 1022 along slot 1030. Other mechanisms can be used as well.

Figure 13A:
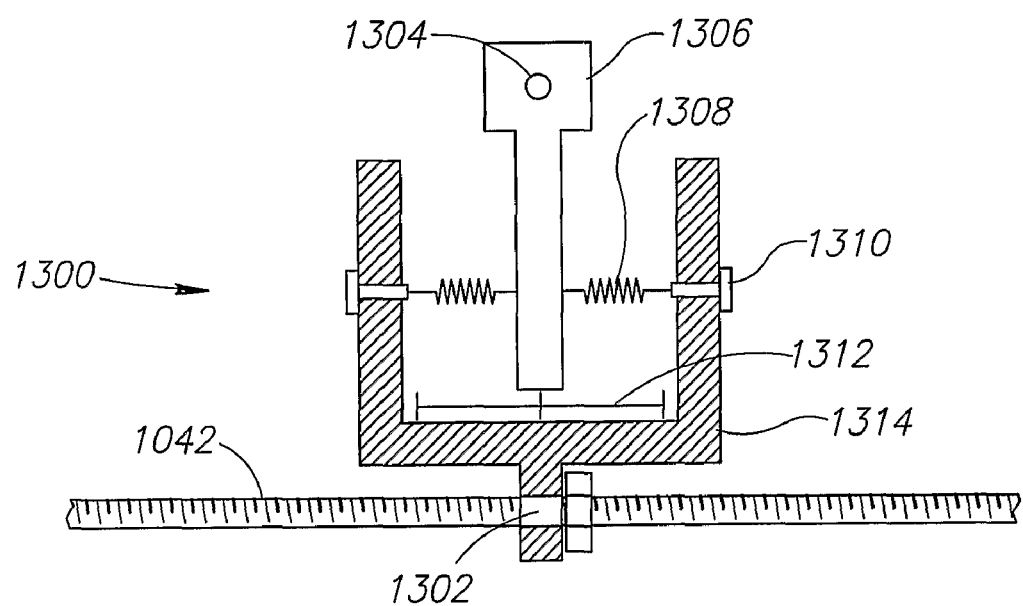
FIG. 13A illustrates a coupling device for a plate drive system, in accordance with an exemplary embodiment of the invention.

As noted in FIGS. 3A and 3B, it is sometimes desirable to provide varying, rather than absolute resistance to motion perpendicular to slot 1030. FIG. 13A illustrates an exemplary coupling device 1300 for replacing coupler 1044, and which has this property. Coupling device 1300 includes a body 1314 having an inner threaded section 1302 for mounting on threaded rod 1042. Body 1314 further comprises an apertured element 1306 having an aperture 1304 which engages rod 1022. One or more spring elements 1308 couple element 1304 to body 1314. Optionally, the tension in spring element 1308 can be adjusted, for example by a screw 1310. Optionally, a linear displacement sensor 1312 is provided to measure the error in the position of rod 1022. Elements 1308 can be provided, for example, in the direction of slot 1030 and/or perpendicular to it. Other exemplary force control mechanisms are described with reference to FIGS. 22-26.

Figure 13B:
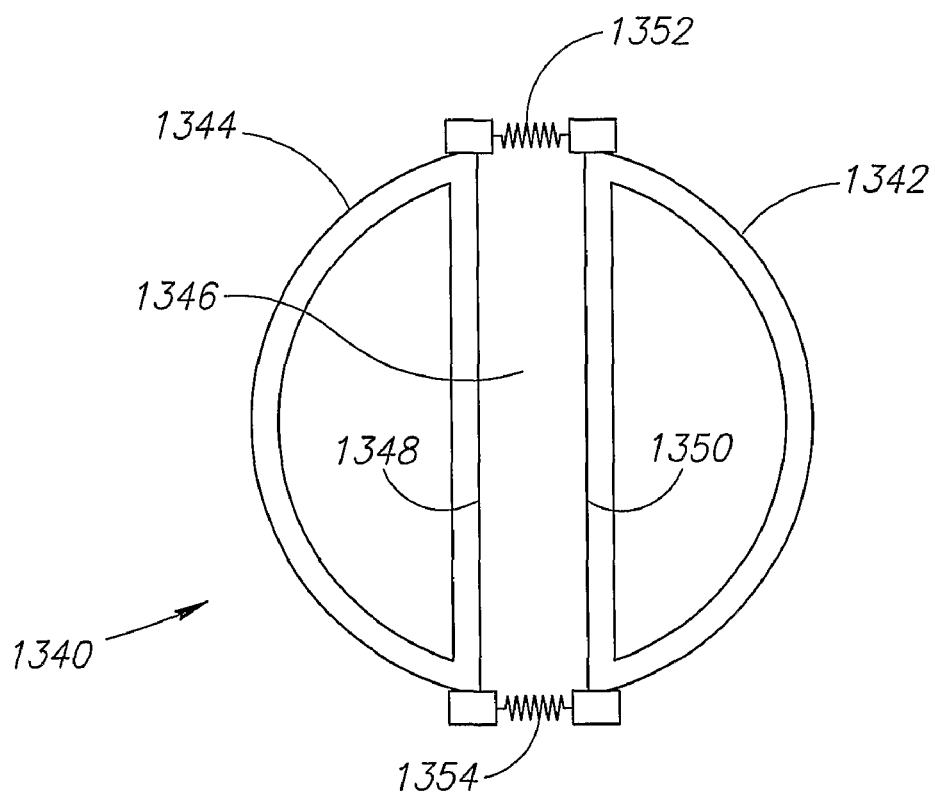
FIG. 13B illustrates a plate with a flexible slot, in accordance with an exemplary embodiment of the invention.

FIG. 13B shows an elastic guide 1340, formed of two halves 1342 and 1344 coupled by one or more springs 1352 and 1354. Thus, a slot 1346 formed between two edges 1348 and 1350 of the halves has some elastic give. Alternatively or additionally, edges 1348 and 1350 are made at least partially elastic, for example, of rubber.

Figure 14A:
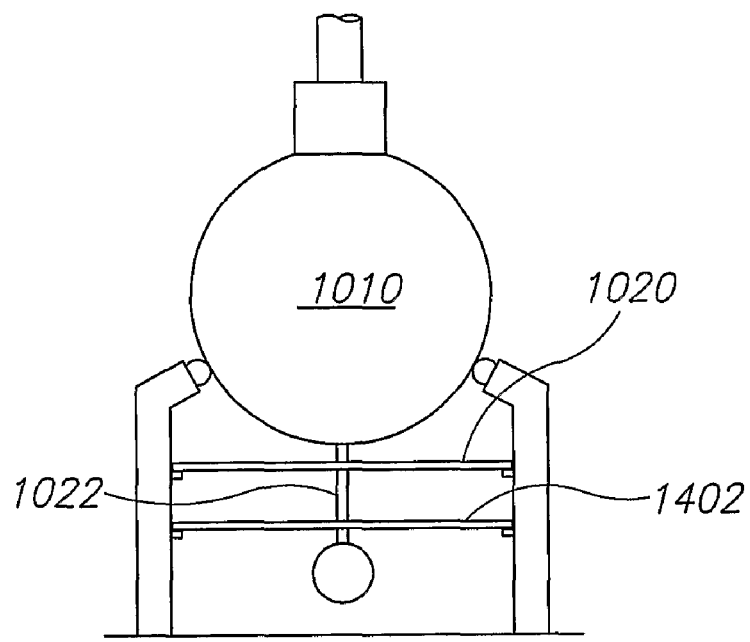
FIG. 14A illustrates a two plate rehabilitation device, in accordance with an exemplary embodiment of the invention.

FIGS. 14A illustrates a variant device, in which two guide plates are used in tandem, an upper guide plate 1020 and a lower guide plate 1402. Separate motors are optionally provided for rotating each guide plate.

Figure 14B:
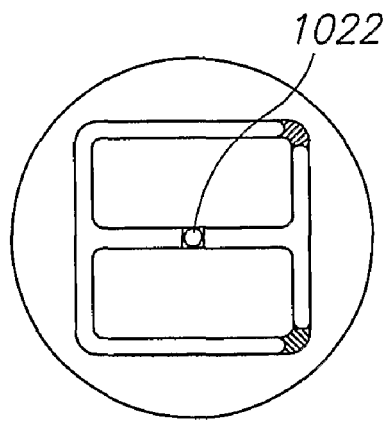
FIGS. 14B and 14C illustrate guide plates in accordance with exemplary embodiments of the invention.

FIG. 14B shows a guide plate with several slots. The solid areas are provided to prevent the cut-outs from falling out. Other methods, for example, out-of-plane bridges, may be used instead.

Figure 14C:
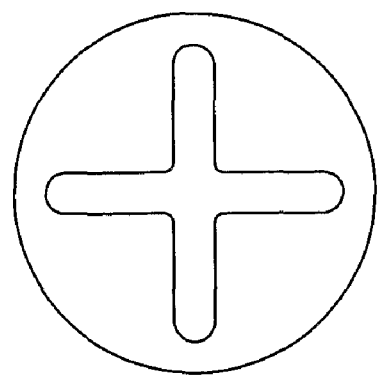

FIG. 14C shows a guide plate with an "X" shaped slot. Other shapes can be provided as well, for example a circle with a cross inside, or curved slots.

In an exemplary embodiment of the invention, programming device 1000 includes replacing slots and/or setting resistance. Optionally, when a slot in inserted, it is recognized by device 1000, for example, using a contact based detection scheme as described above or using a wireless or RF communication, for example, by embedding a smart card circuitry in the plate.

Accessories & Wrist Attachment

Figure 15A:
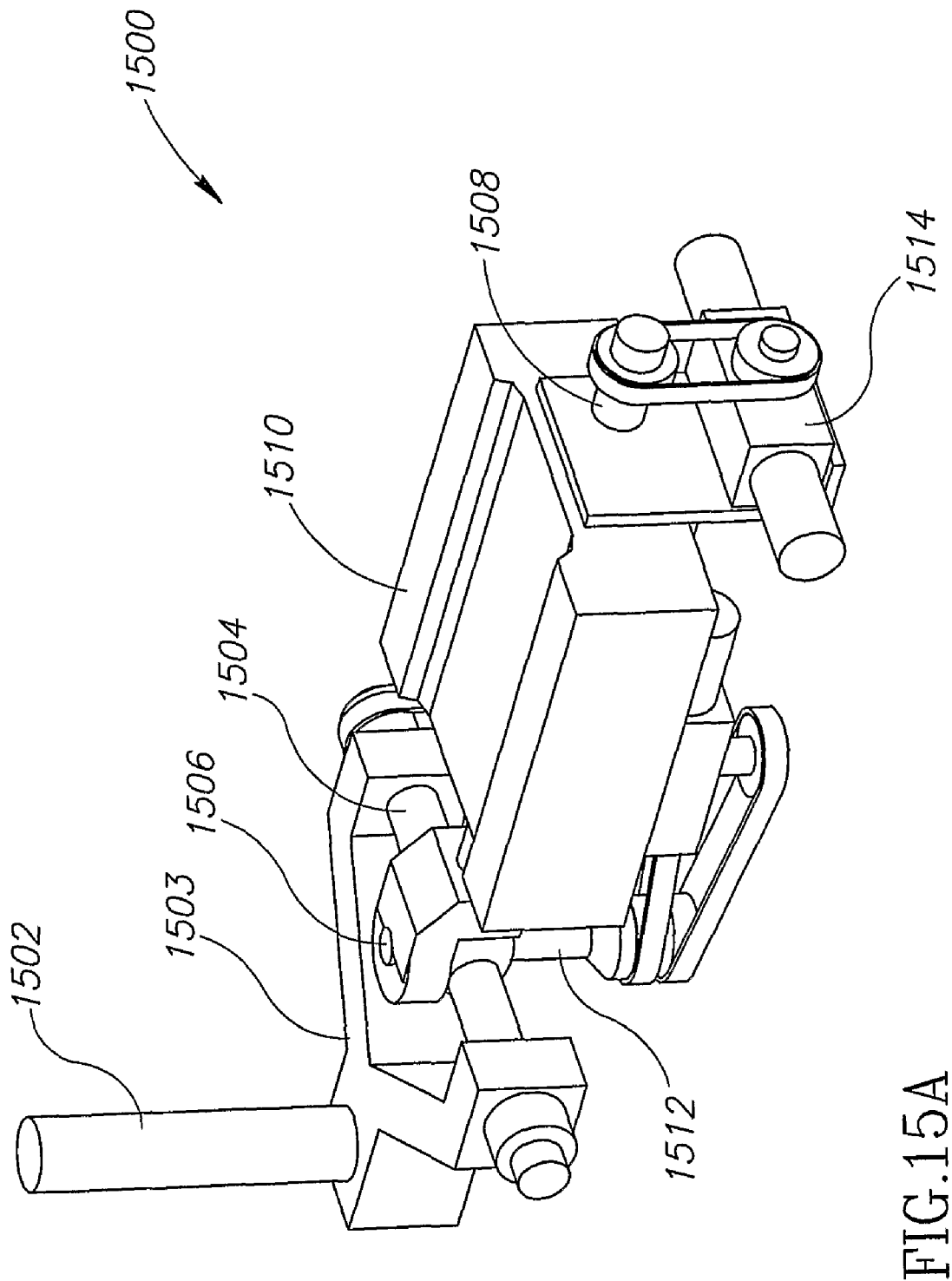
FIG. 15A shows a wrist attachment, which provides control and/or feedback for one or more degrees of motion of a hand, in accordance with an exemplary embodiment of the invention.

FIG. 15A shows a wrist attachment 1500, which provides control and/or feedback for one or more degrees of motion of a hand, in accordance with an exemplary embodiment of the invention.

A forearm is supposed to rest on a rest 1510, while a grip 1502 is grasped by the hand. Grip 1502 is gimbaled in one or more axes relative to rest 1510. In the example shown, handle 1502 is mounted on a base 1503 which includes a rod 1504. A joint section 1506 can optionally rotate around the axis of rod 1504 and/or travel along it. In addition, an optional rod 1508 interconnects rest 1510 and joint section 1506 and allow rotation around rod 1508. In addition, an optional rod 1512 meets joint section 1506 at a direction perpendicular to the other two rods and allows rotation around that third axis.

Optionally, wrist attachment 1500 is attached to tip 1508 at rest 1510 or at a base section 1514 attached to rod 1508.

Optionally, one or more of the relative motions described is supported by one or more motors and/or controllable brakes.

In some wrist attachments (or for other attachment devices), one or more springs the handle to the rehabilitation device so as to provide the varying resistance shown in FIGS. 3A and 3B, in one or more dimensions.

FIG. 15B shows a wrist attachment 1520, according to an exemplary embodiment of the invention and generally following the form of device 1500. A handle 1522 is griped by a patient, while the patient's arm rests on an arm rest 1524. Optionally, one or more straps are provided (not shown) which can attach via one or more strap slots 1526. A base 1542 affords attachment via a connector 1528 to an arm 102 (not shown, but exemplified in FIG. 15C). In an exemplary embodiment of the invention, a universal connector is used which is suitable for multiple attachments as described herein, for example. In an exemplary embodiment of the invention, the connector provides one ore more of mechanical fixation, power (e.g., electrical power) and data transfer. Optionally, the connector also provides identifying information about the attachment to device 100.

In the embodiments shown, three wrist rotations are supported, by mechanical joints 1530, 1532 and 1534. Optionally, the resistance at one or more of the joints is adjustable. In the embodiment shown, the adjustment is manual, for example using one or more of knobs 1536, 1538 and 1540. Alternatively an internal adjustment, for example, using a small electric motor, is provided. The resistance may be, for example, of a friction type or of a resilient (e.g., spring) type. Optionally, rotation sensors are provided for each joint, for example potentiometers.

Optionally, handle 1522 is replaceable, for example, using a pull-pin 1544 to selectably unlock handle 1522 for removal.

Figure 15C:
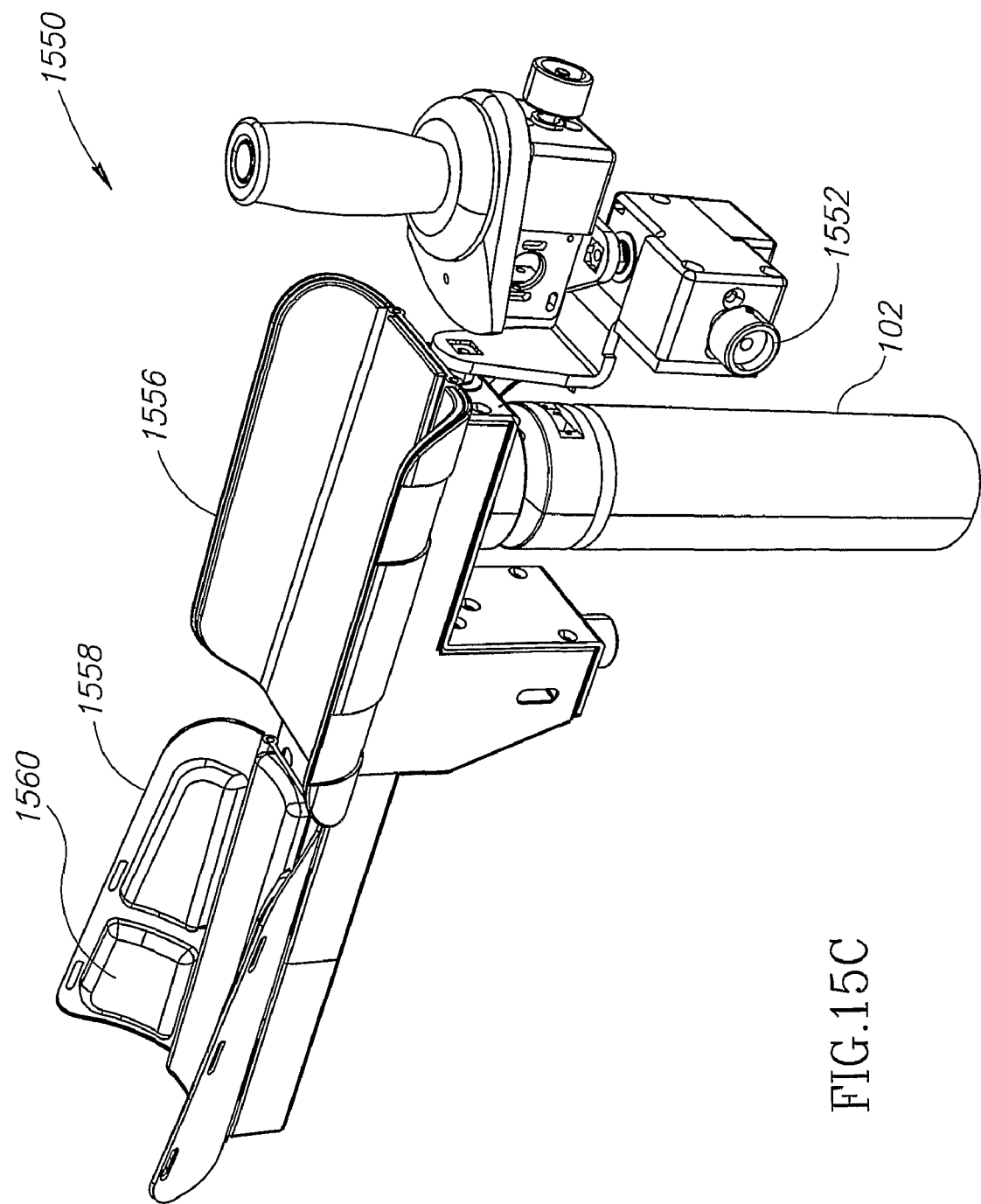

FIG. 15C shows a different version, of a wrist attachment 1550, similar to wrist attachment 1520 (e.g., a knob 1552 is at a different place from knob 1538) and shown from an opposite side. Also shown is the mounting of the wrist attachment on an arm 102. In an exemplary embodiment of the invention, the mounting comprises a ball and socket joint, optionally with friction resistance. Optionally, the socket joint is designed to disconnect if it experiences torque above a certain level, for example as a safety feature. Optionally, this safety level is settable. In an exemplary embodiment of the invention, the joint comprises a ball held between two plates, with the plates interconnected by springs with a settable resistance. A wire interconnecting the plates is optionally provided and may generate a signal is torn (e.g., springs over strained). Optionally, a safety tether is provided to keep the parts of the joint together.

Another difference is that instead of a single arm rest 1524, two arm rests, 1558 and 1556 are shown. Optionally, straps are provided only for the far arm rest (1558). Optional padding 1560 is also shown.

Figure 15D:
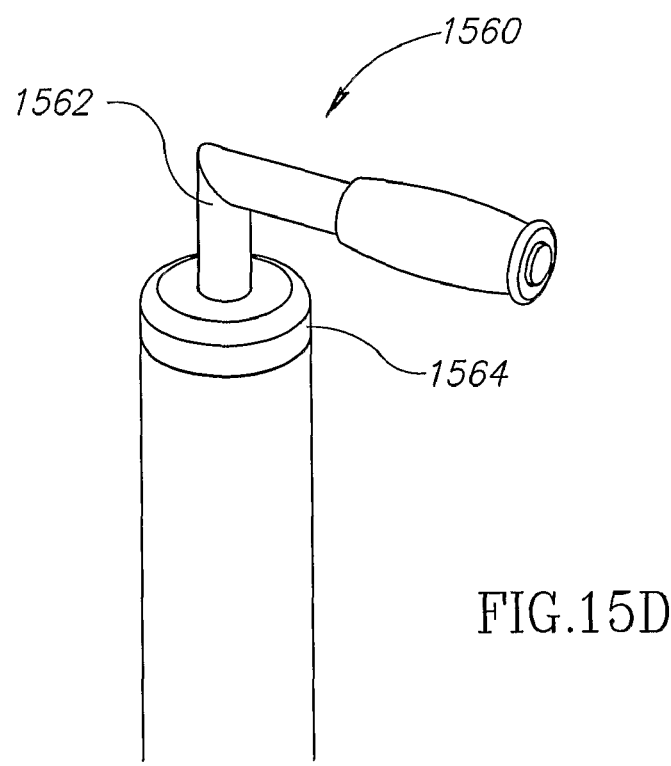

FIG. 15D shows a non-vertical handle attachment 1560. While a 90 degree angle is shown in a bend 1562, other angles, for example 45 degrees may be provided. Optionally, the angle allows better control over which muscles will act and/or may make some motions easier. Optionally, bend 1562 is adjustable, for example to preset angles, such as 0, 45 and 90 degrees.

An optional universal attachment 1564 is shown.

Figure 15E:
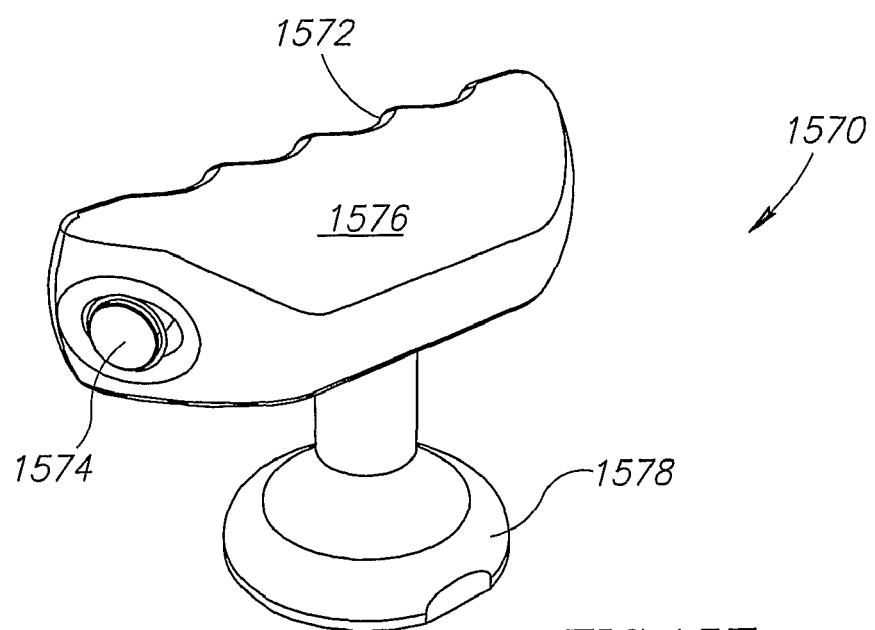
Figure 15F:
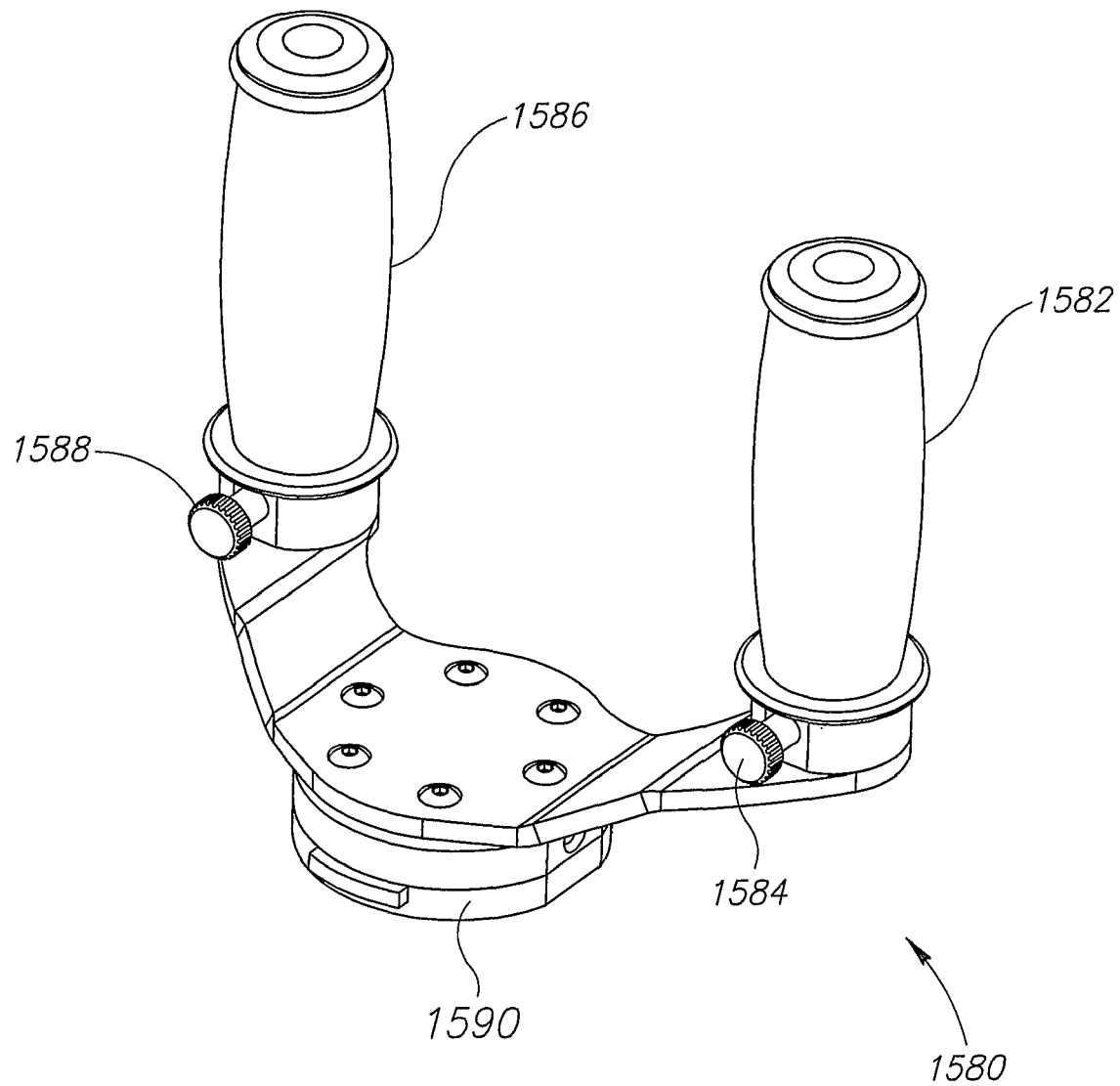

FIG. 15E shows a grip 1570 in which optional finger indentations 1572 are shown. An optional button 1574 for input form the patient is shown. Additional buttons may be provided and buttons may be provided in other embodiments as well.

Optionally, a body 1576 of handle 1570 is squeezable (as it may be in other embodiments as well). One type of squeezable body includes a gas-filled bladder. Optionally, the compression of the gas can be varied to change the resistive force.

In an alternative embodiment, body 1576 is formed of two panels separated by one or more springs.

An optional universal attachment 1578 is shown.

FIG. 15F shows a two handle embodiment 1580 including two handles 1582 and 1586, which are optionally changeable via pins 1584 and 1588. This embodiment may be useful, for example, when it is desired for one hand to assist the other hand in a motion. The two handles actually used need not be identical.

An optional universal connector 1590 is shown.

Other attachments may be used as well. In one example, a cup like attachment is used. A patient can hold the cup as a glass or hold it using a pinching action by its handle. Various sensors to measure pinching force and or grip force (as may be applied to the glass) may be provided. Alternatively, attachments known in the art can be used, optionally being modified to include a universal connector and/or suitable sensors. Optionally, an attachment with a strap to hold the hand is provided.

Optionally, the attachment used provides a sensation to the patient, for example, vibration, pricking, pinching or a surface texture. Electrical power may be provided to the attachment, as well as data, to generate and control such sensation. Surface texture may be varied, for example, by providing a smooth layer with an underlay that is bumpy. Extending the bumps or the bumpy layer, will vary the surface texture.

While the attachments are described for the arm, it should be appreciated that such attachments can be provided to other limbs and to the head and neck. In one example, a pedal is provided as an attachment for a foot. The various rotations of the wrist attachments may also be provided for the foot. Similarly, a head and neck attachment may be designed to hold the support various rotations and/or movements of the chin relative to the neck.

Another type of attachment is not mounted directly on arm 102, patches 504 for example (FIG. 5).

Elbow Support

FIGS. 16A-16D illustrate various methods of elbow support in accordance with exemplary embodiments of the invention. As noted above, for some rehabilitation methods it is useful to provide support for and/or prevent motion of the elbow (or other body parts). In an exemplary embodiment of the invention, device 100 supports the weight of the limb so that a patient can focus on moving the limb and not on holding it in space. Conversely, device 100 may be set to prevent the patient from leaning on the device, for example, with device 100 providing exactly the force expected to be applied by the limb (optionally with some leeway). Optionally, the degree of force changes along the trajectory, for example, as the limb extends.

Figure 16A:
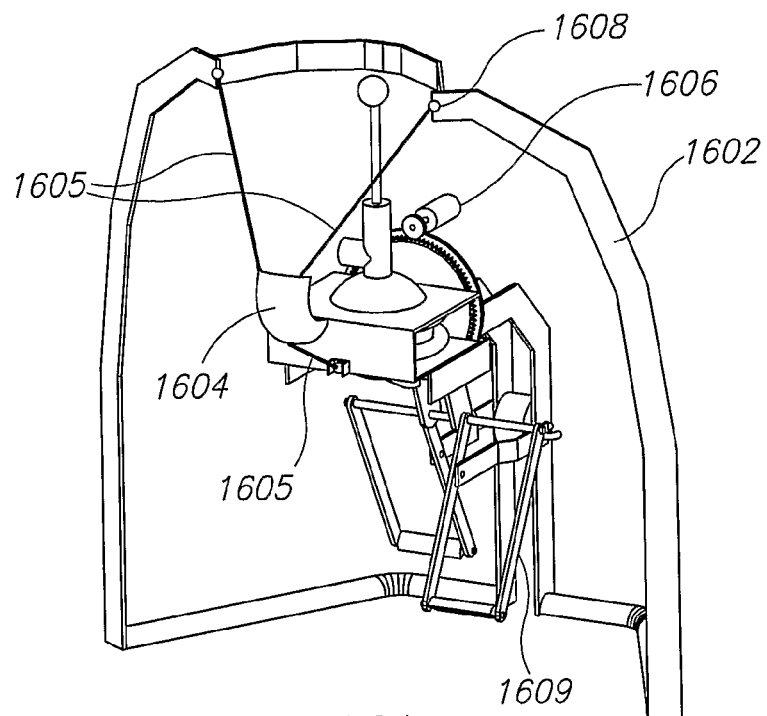
FIGS. 16A-16D illustrate various methods of elbow support in accordance with exemplary embodiments of the invention.

FIG. 16A shows an elbow support 1604 attached by wires to a frame 1602, fixed to the rehabilitation device. Optionally, frame 1602 is collapsible. Optionally, frame 1602 is designed to allow entry of a wheel chair so that a patient on a wheelchair is not required to leave the chair for rehabilitation. One or more foot pedals 1609 are provided for exercising and/or other rehabilitation activities of the legs. Optionally, the pedals are used to support coordinated exercises between arms and legs. Pedals that move in more than one degree of freedom may be provided, as well as various sensors as described herein. A perpendicular motion mechanism 1606 is shown, which may provide room for the knees of a patient sitting in a wheelchair.

In a simplest embodiment, wires 1605 are set (e.g., their length) to a desired elbow location. Optionally, three wires are used so that elbow support 1604 can be fixed in space. Optionally, more wires, for example, four wires are provided, so that even when not occupied, support 1604 does not move. While wires may be used to set an elbow support, such wires may also be used to support other body parts. Optionally, multiple sets of wires are provided, for supporting multiple body parts. Optionally, a wire based system is used instead of an arm 102 or 1002 to control the position of a tip (or attachment) or point on a body.

In an exemplary embodiment of the invention, a wire system is used for measurement of a position in space. In one example, a wire 1605 recoils and is attached to a measurement device such as an encoder. Interpolation can be used to provide XYZ coordinates of support 1604. In another example, described above as well, wires are used to measure a relative position of a chair and a rehabilitation device (e.g., frame 1602).

Optionally, a wire mechanism is attached between two limbs and used to determine their relative distance. Multiple wires may be used to determine more than just a distance value.

Optionally, a wire system is used for measuring additional parameters, for example, force applied to a limb (optionally including direction) and speed of motion. It should be noted that a combined system including (for a same point or tip 108) both robotic elements and wire elements, may be provided.

In an exemplary embodiment of the invention, a wire system is controlled, for example using a motor, to maintain a certain tension. Optionally, this is used to allow floating support of a limb. Optionally, motors are used for controlling or assisting motion, for example with a motor being used to shorten a wire or allow a wire to play out at a certain speed or if a certain force is sensed.

Optionally, a wire 1605 provides compliance against tension, for example, by providing a spring attached to a wire 1605 (e.g., at a point 1608, where a motor may be provided as well). Optionally, the tension in the spring may be varied, for example, using an electric motor. Optionally, the spring is used to provide cushioning in general.

Figure 16B:
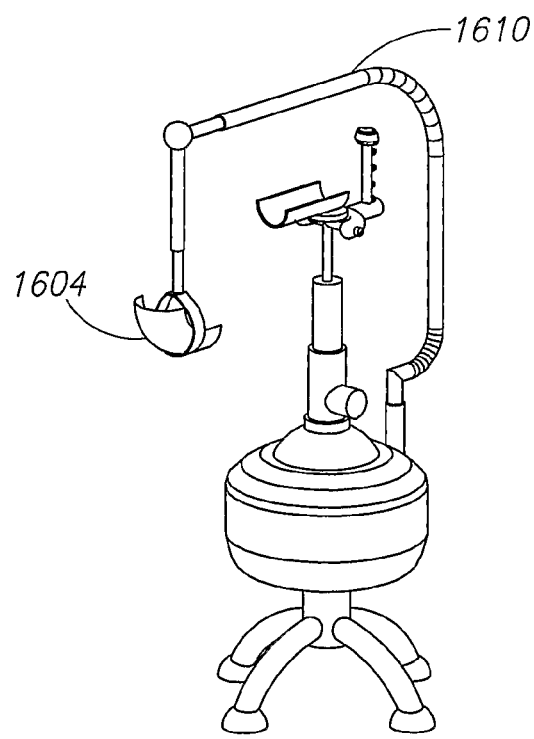

FIG. 16B shows elbow support 1604 supported by an arm 1610 which extends from the rehabilitation device. Optionally, arm 1610 includes a linear extension measurement element and two rotary measurement elements, to indicate the position of support 1604. Other embodiments described herein may also include such sensors so device 100 can calculate the position. Also, as noted, force sensors may be provided, to assist in analyzing the forces applied by the patient to support 1604.

Figure 16C:
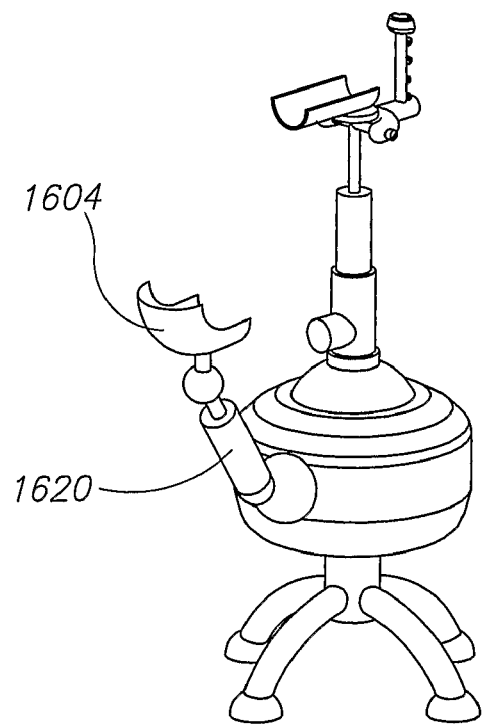

FIG. 16C shows elbow support 1604 supported by a jointed arm 1620 which extends from the rehabilitation device.

Figure 16D:
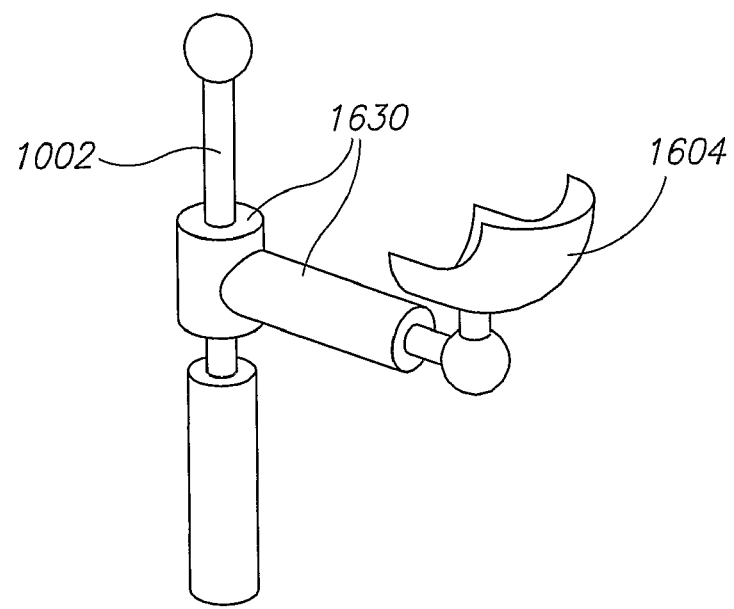

FIG. 16D shows elbow support 1604 supported by a member 1630 which extends out of (and/or is mounted on) arm 1002.

Optionally, the extending arms and members are configurable. Alternatively or additionally, the arms include motors and/or variable resistance elements. Alternatively or additionally, the arms and links include position, orientation, displacement and/or force sensors. In an exemplary embodiment of the invention, the actual position of various parts of the arm may be determined based on the fact that one or more parts of the arm are fixed and the length is known. If any joints are provided, the angle of the joint may be measured.

An additional elbow support example is shown in FIG. 19, below, in a docking station.

Varying Orientation

Figure 17A:
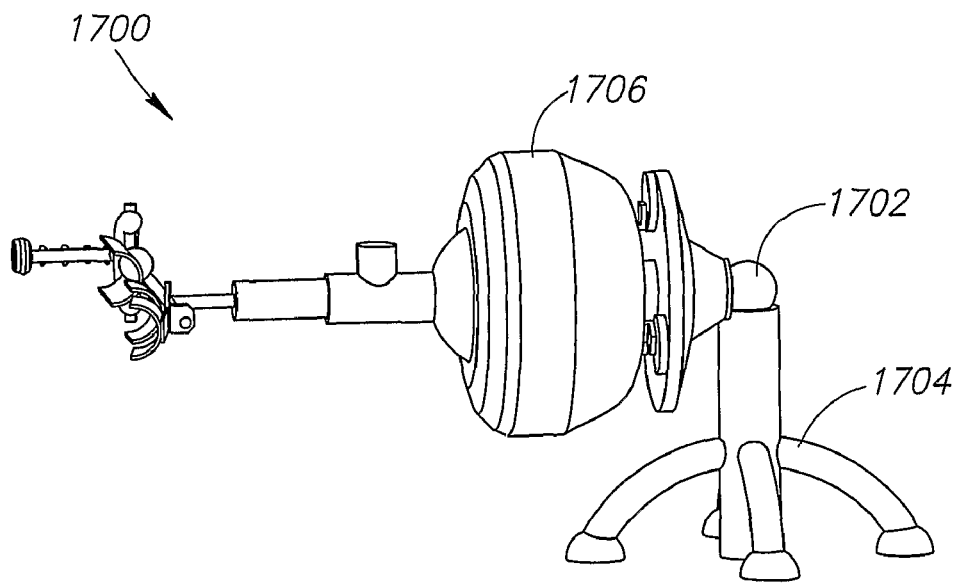
FIG. 17A illustrates a rehabilitation device with varying orientation, in accordance with an exemplary embodiment of the invention.

In some embodiments of the invention it is desirable that arm 102 have a center resting position which is not vertical. FIG. 17A shows a rehabilitation device 1700, including a joint 1702 between a base 1704 thereof and a movement mechanism 1706 thereof, which can assume multiple orientations.

Alternatively, one of the above described rehabilitation devices may be mounted on a surface other than the floor or on legs with uneven lengths. Optionally, when device 1000 is mounted on a wall or upside down, rollers such as rollers 1012 are provided above ball 1010 as well, so that they can support ball 1010, when device 1000 is on its side or upside down. Mounting is achieved, for example, by screws or using an adhesive.

One potential advantage of a varying orientation rehabilitation device is the ability to rehabilitate a patient in varying positions. For example, some exercises, for example those including reaching and balance may be usefully practiced while standing up. Some exercises, must be practiced while lying down, as the patient is bed-ridden. Some exercises may be practiced sitting and others while kneeling.

Another potential advantage is that a same system may be used to rehabilitate different body parts with a same device.

Another potential advantage of a varying orientation rehabilitation device is that many arm motion mechanisms are limited in their range of motion, coupling between axes and/or other mechanical considerations. Varying the orientation of the device allows the motion mechanism to be placed at a more optimal position. It should be noted that in some varying orientation devices, the controlled tip 108 of the device can stay in a same location even though the motion mechanism has moved. This allows, for example, that a patient remain in a wheelchair during a change in exercise.

While a manual change in orientation is shown, optionally one or more motors are used to effect the change in orientation. One or more angle sensors may be provided to detect the actual rotation of joint 1702 (in one or two directions).

Figure 17B:
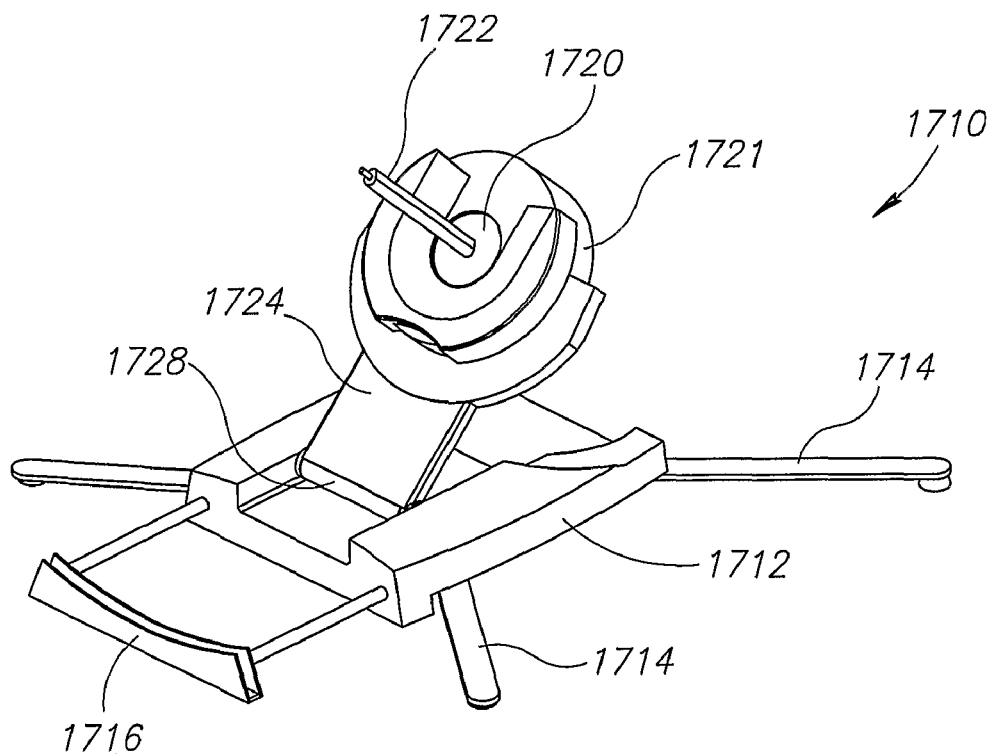
FIGS. 17B and 17C show an alternative rehabilitation device with varying orientation, in accordance with an exemplary embodiment of the invention.
Figure 17C:
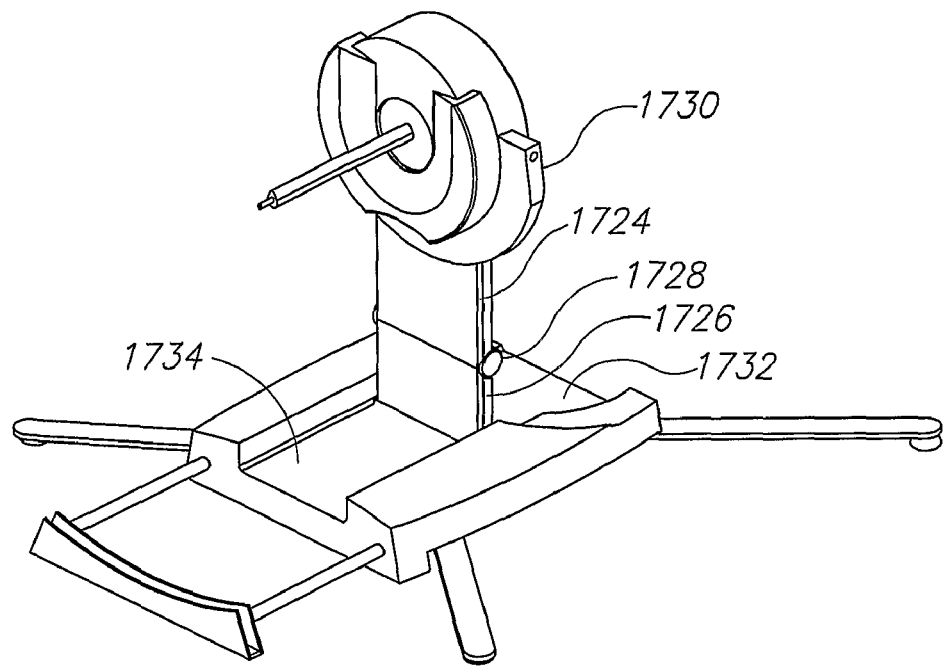

FIG. 17B and FIG. 17C show an alternative varying orientation rehabilitation device 1710, in two orientations. In FIG. 17B, an angled orientation is shown, a support slab 1724 positions a motion mechanism 1720 and an arm 1722 relative to a base 1712. Optionally, one or more extendible legs 1714 are provided for stability. Optionally, a wheelchair guide 1716, optionally extendible, is provided. Optionally, guide 1716 is slotted to allow a wheel to enter therein. Optionally, chucks are added on either side of the wheel to lock the wheel in place. Not shown is an optional bracket based locking mechanism in which one or more pins or brackets engages the wheel from one or both sides thereof, for example along the wheel axis. Such a mechanism may be electrically actuated, for example, by the patient himself. This wheelchair locking mechanism may be used in other embodiments of the invention as well.

In an exemplary embodiment of the invention, slab 1724 can be positioned at various angles. FIG. 17B shows an angle of about 45 degrees. FIG. 17C shows a 90 degree angle. Also shown in FIG. 17C, is a second support slab 1726 attached by a lockable hinge 1728 to support slab 1724. In FIG. 17B slab 1726 is flat against base 1712. Additional possible modes are a 0 degree angle, in which slabs 1724 and 1726 lay flat in a recess 1734 of base 1712. A hinge 1730 is used to rotate motion mechanism 1720 so that it faces upwards. Optionally, motion mechanism 1720 is coupled to hinge 1730 via a rotatable base 1721. Another exemplary position is with slab 1724 lying flat in a recess 1732, so that rotatable base 1721 also lies in recess 1732. This is a transport mode, in which arm 1722 may be detached and the whole of device 1710 may fit, for example, in a trunk of a car. Slab 1726 is optionally attached to base 1712, by another lockable hinge (not shown).

Figure 17D:
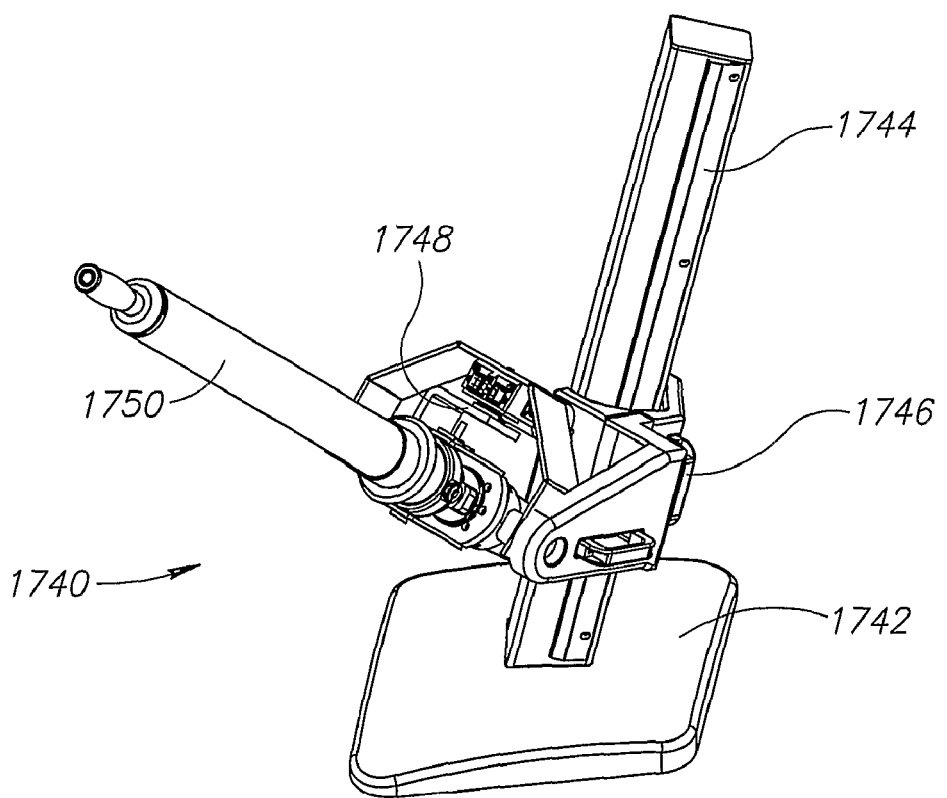
FIG. 17D shows an alternative rehabilitation device with varying orientation, in accordance with an exemplary embodiment of the invention.

FIG. 17D shows an alternative rehabilitation device 1740 with an adjustable position of a motion mechanism 1748 thereof. In this embodiment, a rail 1744 extends from a base 1742 and motion mechanism 1748 is coupled to a traveler 1746 which rides on rail 1744. Optionally, motion mechanism 1748 is attached by a hinge to traveler 1746, to better utilize the range of motion of mechanism 1748 (e.g., allowing an arm 1750 of device 1740 to be centered in a center of a motion space using traveler 1746, rather than using mechanism 1748).

Rail 1744 optionally folds for travel. Rail 1744 optionally includes an in-built data and power bus for transferring at least power to mechanism 1748. Alternatively, a flexible cable (not shown) is used. Base 1742 (as other bases shown herein) may optionally include wheels.

Multi-Limb Devices

In an exemplary embodiment of the invention, multiple limbs can be trained together, for example, for rehabilitating synchronized motion. In an exemplary embodiment of the invention, multiple modules such as used in device 1000 are attached in various configurations to achieve this effect. The attachment can be, for example, structural (e.g., preventing undesired relative motion, but possibly adjustable), mechanical, for example transmitting motion from one module to another, and/or controlled, for example, modifying the interaction at one module in response or in synchrony with interaction at another module.

Figure 18:
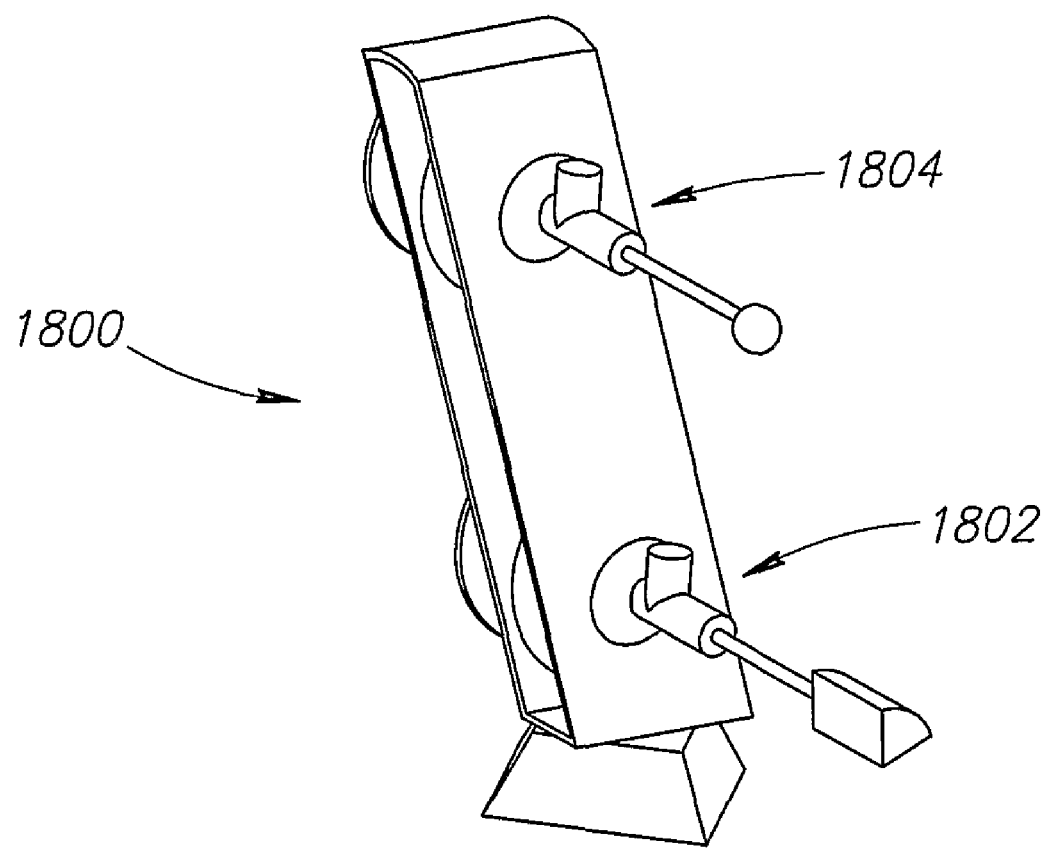
FIG. 18 shows a rehabilitation device for an arm and a leg, in accordance with an exemplary embodiment of the invention.

FIG. 18 shows a rehabilitation device 1800 for an arm and a leg, in accordance with an exemplary embodiment of the invention. Device 1800 includes a first section 1804 for exercising an arm, for example using a mechanism of device 1000, and a second section 1802 for exercising a leg, for example also using the mechanism of device 1000.

One exemplary use for this type of device is to rehabilitate a stroke victim with one side paralysis. Another exemplary use is to train synchronized motions, such as required for walking.

In some cases, two sided rehabilitation is desirable. FIG. 19A shows a rehabilitation device 1900 with four mechanism modules. A pair of modules 1902 and 1904 is used to control the movements of a right arm and a pair of mechanism modules 1906 and 1908 is used to control the movements of a left arm. The two pairs of modules can be synchronized and/or used for teaching, for example, as described above.

Optionally, one or more modules are added for exercising each leg, In the example shown, one or more pedals 1910, such as in FIG. 16A are provided. However, as noted above, devices with a greater degree of freedom can be used. Optionally, gait training mechanisms, for example as described in U.S. provisional application No. 60/633,428 filed on Dec. 7, 2004, also being filed as PCT application on same date as the present application and by the same applicant, entitled "Gait Rehabilitation Methods and Apparatuses", the disclosures of which are incorporated herein by reference, are used. Optionally, such mechanism includes a support which attaches to an ankle and can rotate and/or translate the ankle (e.g., foot) in various (e.g., 2,3,4, or more) directions so as to rehabilitate walking. Optionally, one or more mechanism modules are provided for training hip motion, even while sitting. Optionally, a tread-mill or training bicycle is provided for the patient to walk on while exercising his upper body. Motion of the treadmill is optionally synchronized to rehabilitation exercises and actual performance by the patient. Optionally, gait training includes individual training of different parts of the body and then training them together for a complete (or partial) gait.

Optionally, device 1900 is used with a wheelchair and not a standard chair.

Docking System

FIG. 19B shows a docking station 1920 and FIG. 19C shows docking station 1920 occupied by a wheelchair 1922. By docking station is meant a structure to which a patient can be brought and locked into place and then rehabilitated. From a functional point of view it is generally desirable that only a minimum of manipulation of the patient be required for rehabilitation work to start. Thus, for example, the patient can stay in the wheelchair and optionally instead of adjusting the patient's position (e.g., initially and when exercises change) the rehabilitation device moves, optionally autonomously, to ensure correct relative positioning.

In the embodiment shown, two varying orientation modules 1924 and 1926 are provided on a track 1928. Optionally, the modules are moved by hand. Alternatively, motors (not shown) change the configuration of the modules and/or move them along track 1928. Track 1928 optionally provides power and/or data to the modules. Also non-varying orientation modules or other rehabilitation devices may be attached.

An optional wheel-chair holding mechanism 1932 is shown positioned on a track 1930. Optionally, the position is changed manually. Alternatively, the position is changed using a motor (not shown). Similarly, the wheelchair-engaging mechanism can be manual or motorized.

A set of foot pedals 1934 is shown, but it could be replaced by other foot-training devices.

An optional elbow support 1936 is shown, attached to a joint 1938. Optionally, elbow support 1936 is floating with respect to the person, optionally adjusted to compensate for the weight of the patient. Optionally, the floating is in a plane, for example in a plane parallel to the floor. Optionally the location of the elbow is measured by the support and can be used for various feedbacks such as measurement of quality of motion. Support 1936 is optionally on a telescoping and/or articulating arm, for example as described in FIG. 16.

A display 1940 is optionally provided, for example for use of a therapist and/or the patient. An input system 1942, for example a keyboard and a joystick may be provided as well. Optionally, the input and output devices 1940 and 1942 can be swiveled to different positions, so that the therapist can access them while docking station 1920 is occupied.

Display 1940, input 1942 and/or joint 1938 are optionally mounted on a column, optionally a telescoping column. Optionally, a display 1946 (audio and/or visual) dedicated to the patient is provided.

A similar docking station may be provided for a gurney, for example with four motion mechanisms, one for each limb. Alternatively, as described below, the rehabilitation device is made portable enough so that it may be brought to a bed-ridden patient.

Mobility

A feature of some embodiments of the invention is that a rehabilitation device is provided which is mobile. There are various levels of mobility and various embodiments of the invention, as described herein can achieve these levels.

In an exemplary embodiment of the invention, mobility of a rehabilitation device is used to move the device within a ward or between hospital wards.

FIG. 19D shows mobile rehabilitation devices 1950 positioned near a bed 1951, in accordance with an exemplary embodiment of the invention. In this embodiment of a mobile device, a motion mechanism 1952 is mounted on a rail 1958, for example a curved rail with a base 1960. Wheels, optionally lockable and/or extending legs (not shown) may be provided on base 1960. Rail 1958 optionally includes one or more tracks 1962 (slots shown) for adjusting the position of mechanism 1952. Two different attachments are shown, 1954 for an arm and 1956, for a leg. Optionally, the wheels are used to move device 1950 into storage. Collapsible devices were described above, for example in FIG. 17B.

FIG. 19E shows an alternative mobile rehabilitation device 1964, coupled to bed 1951, in accordance with an exemplary embodiment of the invention. One or more attachment mechanism 1972 lock device 1964 to bed 1951. Wheels are optionally provided. Device 1952 may be used, for example for rehabilitation from above. In an exemplary embodiment of the invention, device 1964 comprises a frame 1970 on a top part 1966 of which a movement mechanism 1952 is mounted. Optionally, device 1952 can move along the frame. A ball grip attachment 1968 is shown.

Mobility may also be useful in other settings, for example, at home or in a small clinic. Also, as noted above, a mobile rehabilitation device may be carried by a therapist on home-calls.

In an exemplary embodiment of the invention, rehabilitation is performed in water (or a steam bath), or with water supporting the patient and/or providing heat and/or massage. FIG. 19F exemplifies the use of mobile rehabilitation devices 1972 in a bathtub 1976, in accordance with an exemplary embodiment of the invention. A wheeled base 1978 is shown, but other base types, including a fixed base, may be used. In the embodiment shown, two arm attachments 1974 with extended connections are used and the patient may be sitting or lying down.

Rehabilitation may also be carried out in a swimming pool, with device 1972, for example, being attached to a ceiling above the pool.

In an exemplary embodiment of the invention, the rehabilitation device is kept outside the water, but attachments are made waterproof. Optionally, the device itself is made waterproof or at least splatter-proof. Optionally, the rehabilitation device is made battery operated, to prevent electric-shock hazard. Alternatively, pneumatic or hydraulic motors are used instead of electric motors. Optionally, low-voltage (e.g., 24, 12, 5 volts or less) are used to power the rehabilitation device. Optionally a device without motors that includes brakes, is used In an exemplary embodiment of the invention, the mobility of the rehabilitation device is used for rehabilitation in the outdoors, for example in a person's garden (e.g., on grass) or in nature. In one example, a rehabilitation device is used for a recreational activity such as barbequing. The device can be used to help guide, diagnoses and train a patient in flipping hamburgers, for example. Optionally, large wheels are provided for better traveling over soft surfaces. In another example, the rehabilitation device is used to rehabilitate outdoor activities such as golf or fishing. Optionally, special attachments are provided for such activates, to match the range of motion of the movement mechanism used to the activity. In a fishing example, the rehabilitation device can assist for example in holding a fishing rod, generating range of motion in the shoulder to through a fly and in resisting the pull of a fish (which is a varying force). Exemplary attachments are an attachment to a fishing rod and an attachment to a tip of the rod (e.g., simulating a fish).

In an exemplary embodiment of the invention, a leveling mechanism is provided for uneven surfaces. This mechanism, for example, similar to that of FIG. 17A includes an inclination sensor which detects the level plane and adjusts the motion mechanism to be arranged suitably.

In an exemplary embodiment of the invention, a tip and or tilt detection mechanism is provided. Optionally, when tipping is detected (e.g., acceleration of the base of a rehabilitation unit), the unit generates a warning signal. Optionally, any attachments to the patient are released, to prevent damage to the patient. Optionally, the base includes collapsible sections so that if tipping is detected, the base can collapse one section thereof and cause the device to fall away from the patient.

In an exemplary embodiment of the invention, a mobile rehabilitation system for use out side of a sterile environment is made easier to clean and/or proof against spills, dirt and some weather conditions. Optionally, the electronics and motion mechanisms are sealed. Optionally, joints are covered with flexible rubber so that fewer bumps and cracks are present. Optionally, a wipe-clean plastic covering is provided on the device.

In an exemplary embodiment of the invention, the rehabilitation system is mounted on a wheelchair, for example on its side or in back, or in a car, for example, in the seat near a driver. Optionally, the device can be fitted in the back of a van and the van is configured to be used as a mobile rehabilitation unit, where a patient can enter (possibly in a wheel chair, possibly using a lift) and exercise.

Modularity

In an exemplary embodiment of the invention, a rehabilitation device optionally features modular design. Such modular design may manifest itself in one or more of the following manners:

(a) The device is capable of being broken down into modules. This allows, for example, for maintenance by replacing a defective module. Alternatively or additionally, the mobility of a device is enhanced by the ability to take it apart into components which can be quickly put together again by a layperson. In an exemplary embodiment of the invention, no special tools are required for taking apart or for putting together the device. Optionally, a simple screwdriver or turn wrench is used. Optionally, the device can be broken down/ folded up or put back together in less than 1 hour. Optionally, the time required is less than 30 minutes, less than 20 minutes or less than 10 minutes, 5 minutes or 2 minutes, for example.

(b) The device itself is a module. As can be seen for example in FIG. 19, a same motion mechanism module can be used for multiple different rehabilitation configurations. Optionally the unit as shown in FIG. 17 is used as an attachable/detachable module for the docking station of FIG. 19B.

(c) Modular attachments. As shown for example in FIGS. 16-19, various types of attachments can be added to a same basic device, thereby changing its usage. In a particular example, the device is adapted for various patient sizes, for example children with Cerebral Palsy, by replacing parts, for example an arm 102, with suitably sized parts.

In some embodiments of the invention the hand attachment includes mechanical and electrical quick connections. The mechanical quick connect may include a pin that fits to a hole with locking the electrical quick connect can includes spring loaded needles on one side and surface pads on the others. A same set of connectors may be used for multiple attachments.

(d) Modular software. Optionally, the software used by the rehabilitation device is provided as modular software, for example, separate modules for different attachments; modules which includes sets of exercises; separate modules for different motion modes; and/or separate modules for different uses of the device (e.g., group, home or clinic).

Daily Life

As noted above, in an exemplary embodiment of the invention, a rehabilitation device is used to help specifically rehabilitate a patient to achieve daily activities, such as opening doors, eating at a table, reading a book, getting dressed, brushing teeth and washing dishes.

FIG. 19G shows a rehabilitation device 1980 configured for use for daily activities, in accordance with an exemplary embodiment of the invention. A rehabilitation module 1952 is mounted upside down over a table 1986 set with various eating utensils. An elbow rest 1984 is optionally provided. In this embodiment table 1986 is attached to a frame 1988 which supports mechanism 1952. Alternatively, frame 1988 may be wide enough to surround an existing table or other home element.

In use, a hand of the patient is strapped to a movable tip 1982 of device 1980 and the user attempts to or is guided through a daily activity such as picking up a fork. Optionally, a glove with force-feedback is used to selectively rehabilitate individual fingers. Such gloves are known in the art.

In an exemplary embodiment of the invention, device 1980 is used for one or more of training a patient to do activities related to daily life, testing the patient's current ability to do such activities and/or monitoring a patient's ability. Optionally, such testing and/or monitoring are used by insurance companies to decide on compensation or assistance required. Such testing can be repeated over a period of time so that attempts to cheat may be detected by sudden spikes in ability.

It is noted that a very important goal for rehabilitation is quality of life, which is optionally addressed and/or determined by training and testing the ability to perform various daily activities.

In an exemplary embodiment of the invention, specific attachments are provided for daily activities training. In one example, a spillage indicating cup is provided, which includes an inclination sensor. In another example, a whiteboard with ability to detect a pen position is used in rehabilitation exercises involving writing on a wall. The detected position and/or pressure is reported to the rehabilitation device which optionally holds, supports and/or guides the hand of a patient.

In an exemplary embodiment of the invention, an implement of daily living is turned into an attachment by providing one or more patches, for example stickers which include a sensors, for example a position or a pressure sensors, and attaching the patch to a daily use implement, such as hammer or a wall. The rehabilitation device optionally includes a position determining means, for example a wireless unit which communicates with position sensors on the patches or a camera which images the patches, so that the rehabilitation device can determine relative positions and/or orientations of the daily use objects. In some cases, rehabilitation and/or diagnosis is carried out using the methods described herein but without mechanical support or kinesthetic feedback. Optionally, vibration or other feedback is provided to a patient by attaching a vibrating patch (under control of the rehabilitation device) to a limb which is being rehabilitated.

U.S. provisional application No. 60/566,079 filed on Apr. 29, 2004, also being filed as PCT application on same date as the present application and by the same applicant, entitled "Fine Motor Control Rehabilitation", the disclosures of which is incorporated herein by reference describes various structures useful for rehabilitation of fine motor control or the combination of fine and gross-motor control.

FIG. 19H shows a device 1990 for assisting in training for activities of daily living, in accordance with an exemplary embodiment of the invention. Rather than provide an entire table, device 1990 includes two settable points 1992 and 1993 connected to a base 1994. A pair of adjustable arms, for example goose-neck arms 1996 can be used to adjust their position in space. In use, for example for pouring tea, set points 1992 and 1993 are positioned to emulate a situation, for example pouring tea. In an exemplary exercise, a patient is required to move a cup (e.g., helped by a rehabilitation device, not shown) from point 1992 to point 1993. the trajectory is then evaluated. Set point 1993 is shown as a flat surface, on which items may be placed. Other structures and attachments, such as hooks, may be used. Optionally, set points 1992 and 1993 (more may be provided) include sensors, for example proximity sensors (to detect human or rehabilitation robot), contact sensors, pressure sensors and/or position sensors. The set points may also provide feedback, for example, lights, sound or vibration.

The relative positions of points 1992 and 1993 may be determined, for example, using position sensors or cameras. Alternatively, tip 108 is used to register their position to the rehabilitation device, by contacting points 1992 and 1993 in turn by tip 108. Optionally, a dummy arm is mounted on the rehabilitation device to calibrate the relative expected position of tip 108 and a set point, when the set point is actually being touched by a part of the user, such as a finger.

Small Chuck

In an exemplary embodiment of the invention, a joint in an articulated arm is configured to provide selective and/or directional resistance.

Figure 20:
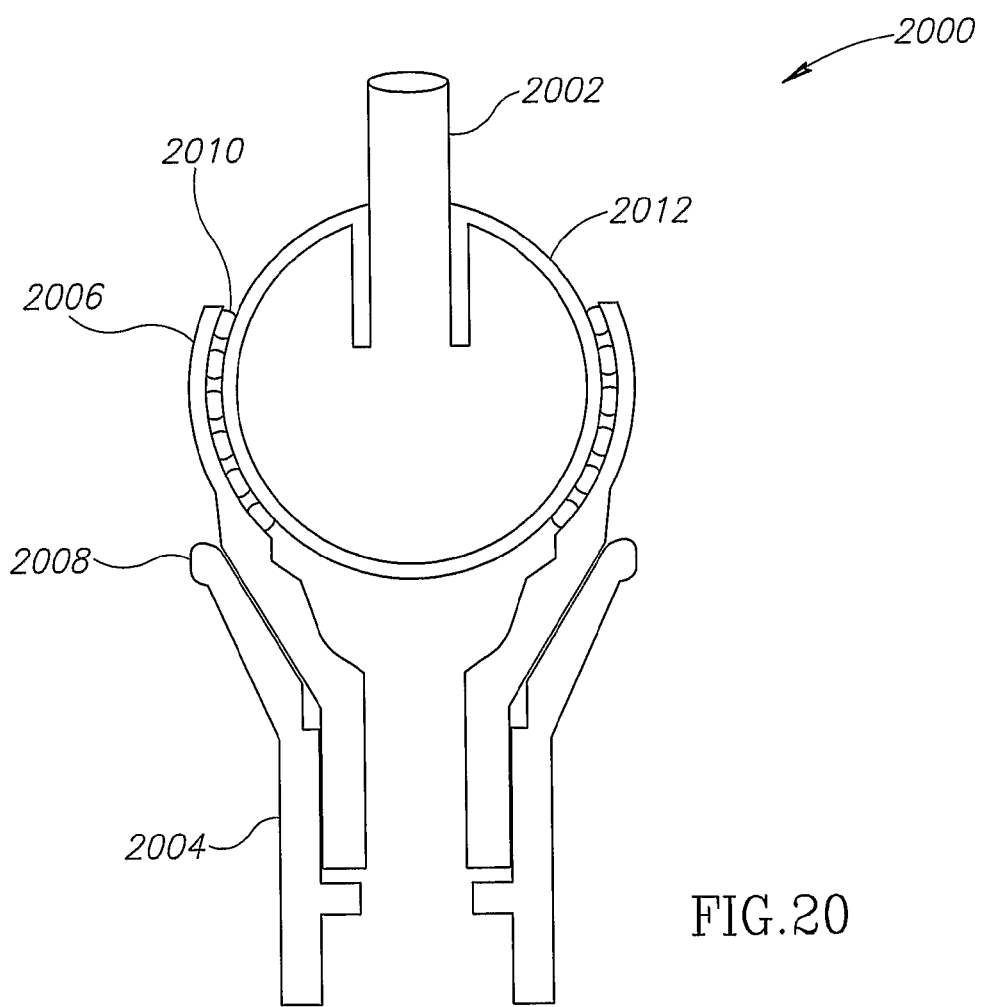
FIG. 20 shows a chuck mechanism in accordance with an exemplary embodiment of the invention.

FIG. 20 is a cross-sectional view of such a joint between a rod 2004 and a rod 2002. A chuck 2006 fits into a flaring end 2008 of rod 2004 and engages a ball 2012 attached to rod 2002. If chuck 2006 is retracted towards rod 2004, it tightens around ball 2012 and increases the resistance thereof.

Optionally, one or more strain sensors and/or optical sensors is provided between chuck 2006 and ball 2012, so that a direction of force being applied to joint 2000, can be determined. Optionally, one or more electrically activated brake elements are provided, for example piezoelectric elements, which can selectively modify a degree of resistance. This may be provided instead of or additional to a retracting chuck mechanism.

Balanced Gimbal Device

Figure 21:
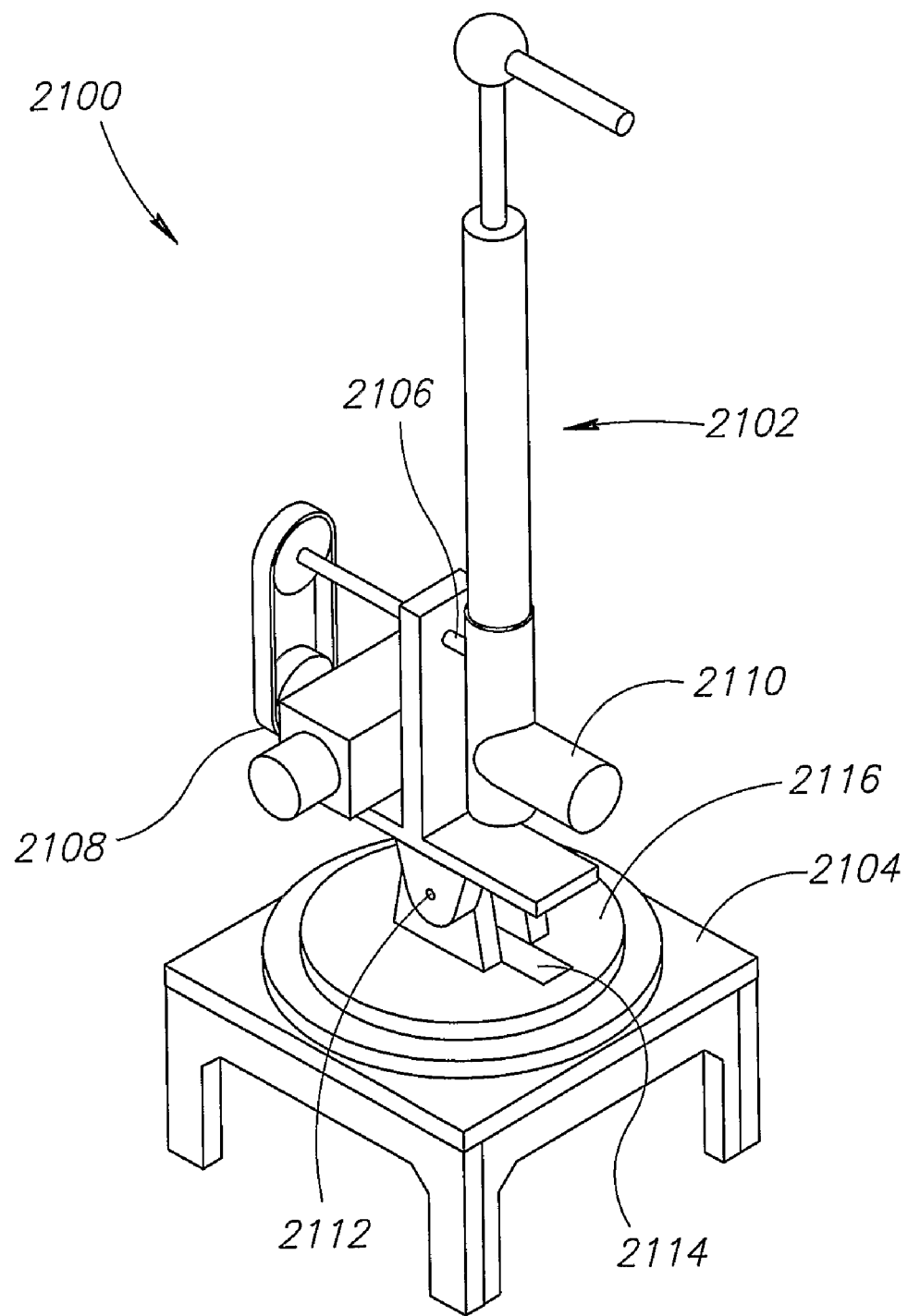
FIG. 21 shows an alternative non-ball, balanced, rehabilitation device, in accordance with an exemplary embodiment of the invention.

FIG. 21 shows an alternative rehabilitation device 2100, in which a ball joint is not used. An arm 2102, optionally extendible is optionally balanced by an optional counter-weight 2110 around an axle 2106. Counter-weight 2110 may include a motor or variable brake for controlling extension of arm 2102.

A motor 2108 is optionally provided to rotate arm 2102 around axle 2106. A second hinge 2112 is provided to allow rotation around an axis perpendicular to arm 2102 and axle 2106. Optionally, motor 2108 includes a weight so that it balances arm 2102 relative to hinge 2112. Optionally a slot 2114 is provided in a base section 2104 of device 2100, for functioning as plate 1020 and slot 1030 above. A similar structural arrangement may be used as well. Optionally, a rotatable plate 2116 is provided for carrying slot 2114. A motor (not shown) is optionally provided for rotation around joint 2112. Optionally, joint 2112 is raised to have an axis crossing the axis of axle 2106.

Alternative Gimbaled Device

Figure 22A:
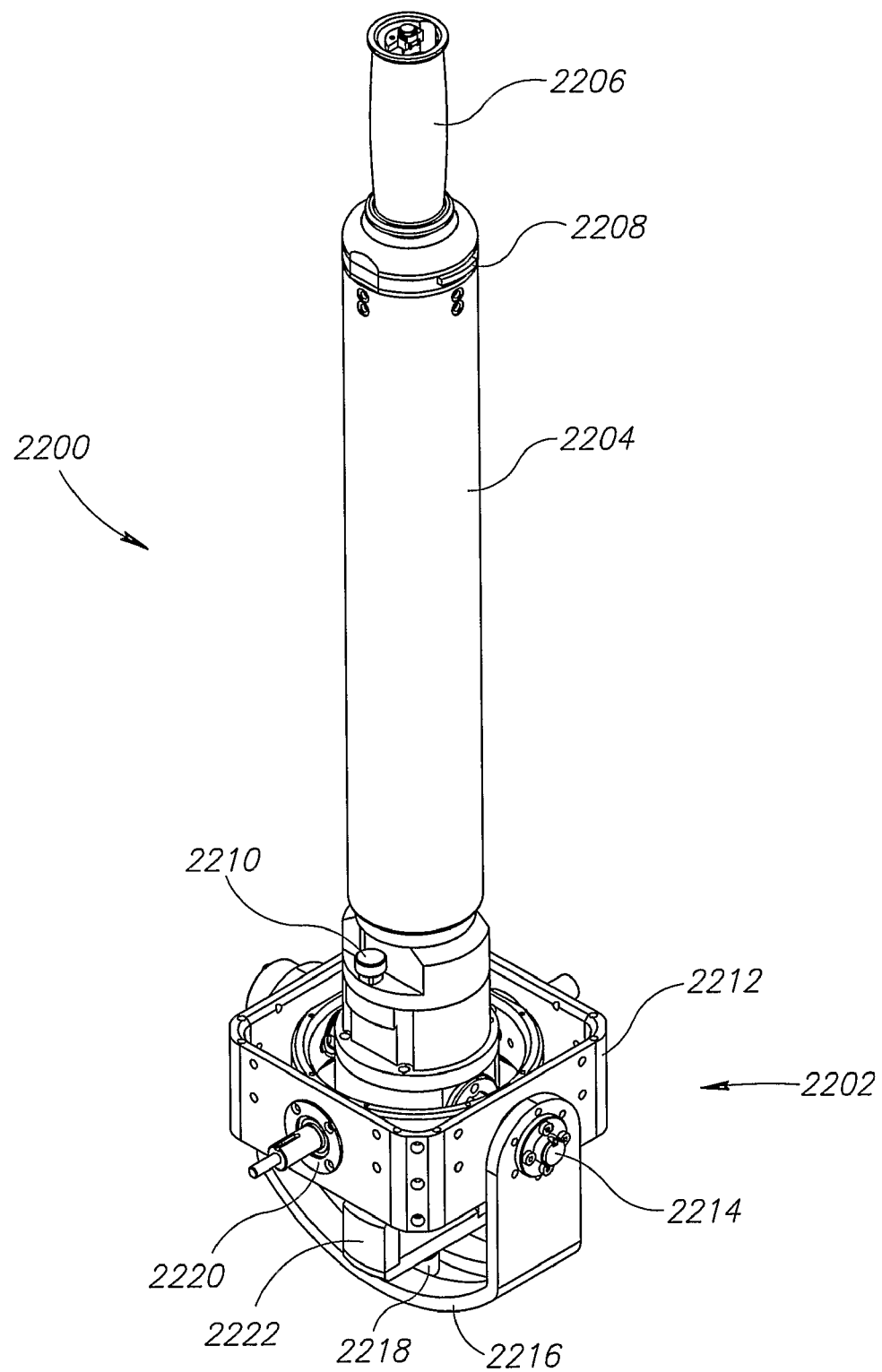
FIG. 22A shows another alternative non-ball rehabilitation device mechanism, in accordance with an exemplary embodiment of the invention.
Figure 22B:
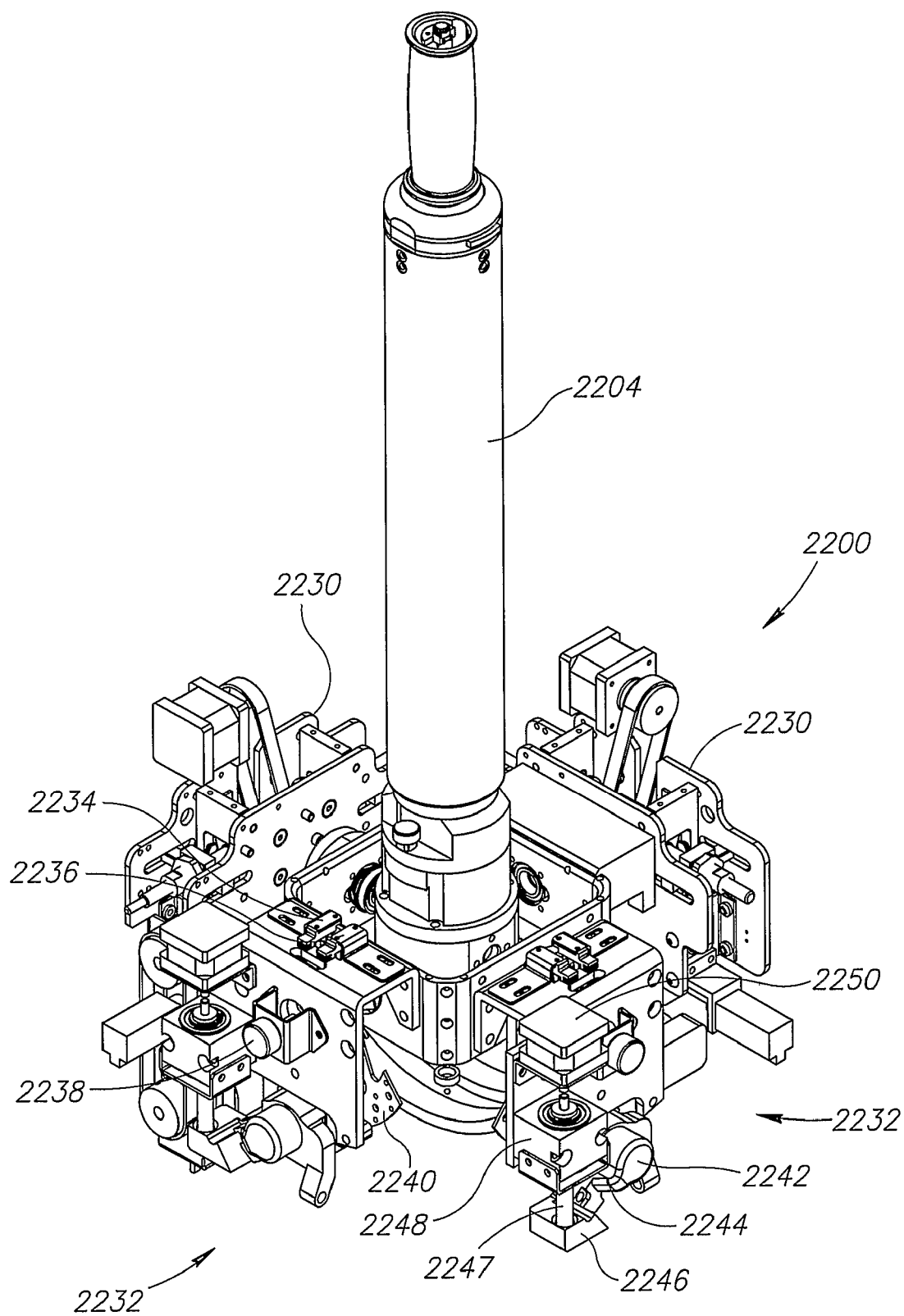
FIG. 22B shows force control mechanisms and brakes attached to the device of FIG. 22A.

FIG. 22A shows an alternative gimbaled device 2200 for use as a motion mechanism in accordance with an exemplary embodiment of the invention. FIG. 22B, described below shows a configuration of device 2200 including motors and/or brakes.

Device 2200 includes a gimbaled section 2202, an optionally removable z-axis element 2204 and an optionally replaceable handle 2206 attached thereto. A modular connector 2208, for example as shown in FIG. 15 may be used. Optionally, a release pin 2210 is user to selectively take off z-axis element 2204, for example, for replacement or for storage.

Gimbaled section 2202 optionally includes a frame 2212 including a first hinge 2214. Optionally, a guiding frame 2216 is attached to hinge 2214 that provides a first stationary axis and includes a guide pathway for guiding an extension (or cam follower or pin) 2218 (described below).

A second stationary axis is provided by a hinge 2220 also on frame 2212. In an exemplary embodiment of the invention, handle 2204 is optionally rigidly attached to a frame 2222 which includes extension 2218. Thus, the spherical rotation motion of handle 2204 is translated to rotation of the two hinges around the stationary axes. Optionally, extension 2218 includes a balancing weight (not shown).

FIG. 22B shows device 2200 in an exemplary deployed configuration, with two braking mechanisms 2232 and two force control mechanism 2230 attached. As can be appreciated a practical device can be constructed with only one of resistance and force control. Force control mechanisms 2230 are described below in greater detail.

Referring to braking mechanism 2232, in an exemplary embodiment of the invention, a disc braking mechanism is used in which a disc (or part of a disc) 2240 is selectively constrained by a friction element (not shown). A motor 2250 selectively sets the pressure applied by the friction element on the disc. Other friction mechanisms may be provided as well. In an exemplary embodiment of the invention, the following mechanism is used to couple motor 2250 to disc 2240. A coupling 2248 converts rotational motion of motor 2250 into axial motion of a rod 2247. Optionally, rod 2247 is spring-loaded so that absent power to motor 2250, the pin moves to a locked or an unlocked position, where the friction on disc 2240 is maximal or minimal (depending on the implementation). A rest 2246 is thereby selectively lifted or pushed down by rod 2247. The friction element, while not shown, is coupled to a rotatable element 2242 that converts rotation thereof to motion of the friction element towards or away from disc 2240. Optionally, element 2242 is a screw. Element 2242 includes an trans-axial lever 2244 which is engaged by rest 2246 and thereby rotates element 2242 when rest 2246 is moved. Rotatable element 2242 is optionally spring-loaded.

Other brake mechanisms can be used, for example as known in the art of brakes, for example, electrical, fluid, magnetic and/or mechanical brakes.

In an alternative embodiment of the invention, coupling between motion in the various axis is reduced by providing a single unidirectional brake. In an exemplary embodiment of the invention, the brake comprises a spherical segment which is selectively pressed against pin 2218.

Also shown in FIG. 22B are various optional sensors. A sensor 2234 is coupled to the axis of hinge 2220 and report when handle 2204 is rotated to its limit(s). A sensor 2236 reports when the handle is in a reference (or home) position. A sensor 2238, for example a rotatary potentiometer or encoder reports on the angle of rotation of hinge 2220. Similar sensors may be used for the hinge 2214.

In some embodiments of the invention, the brake mechanism is used for one or more of providing safety by stopping motion, providing programmable resistance (even in a system without active motion of the device) and/or balancing (e.g., by providing friction when needed to counteract external forces). Optionally, the braking action in the two modules 2232 is coupled to provide for uniform braking behavior independent of whether the motion of handle 2204 is along one of the stationary axes or not.

Cantilevered Gimbaled Mechanism

Figure 23:
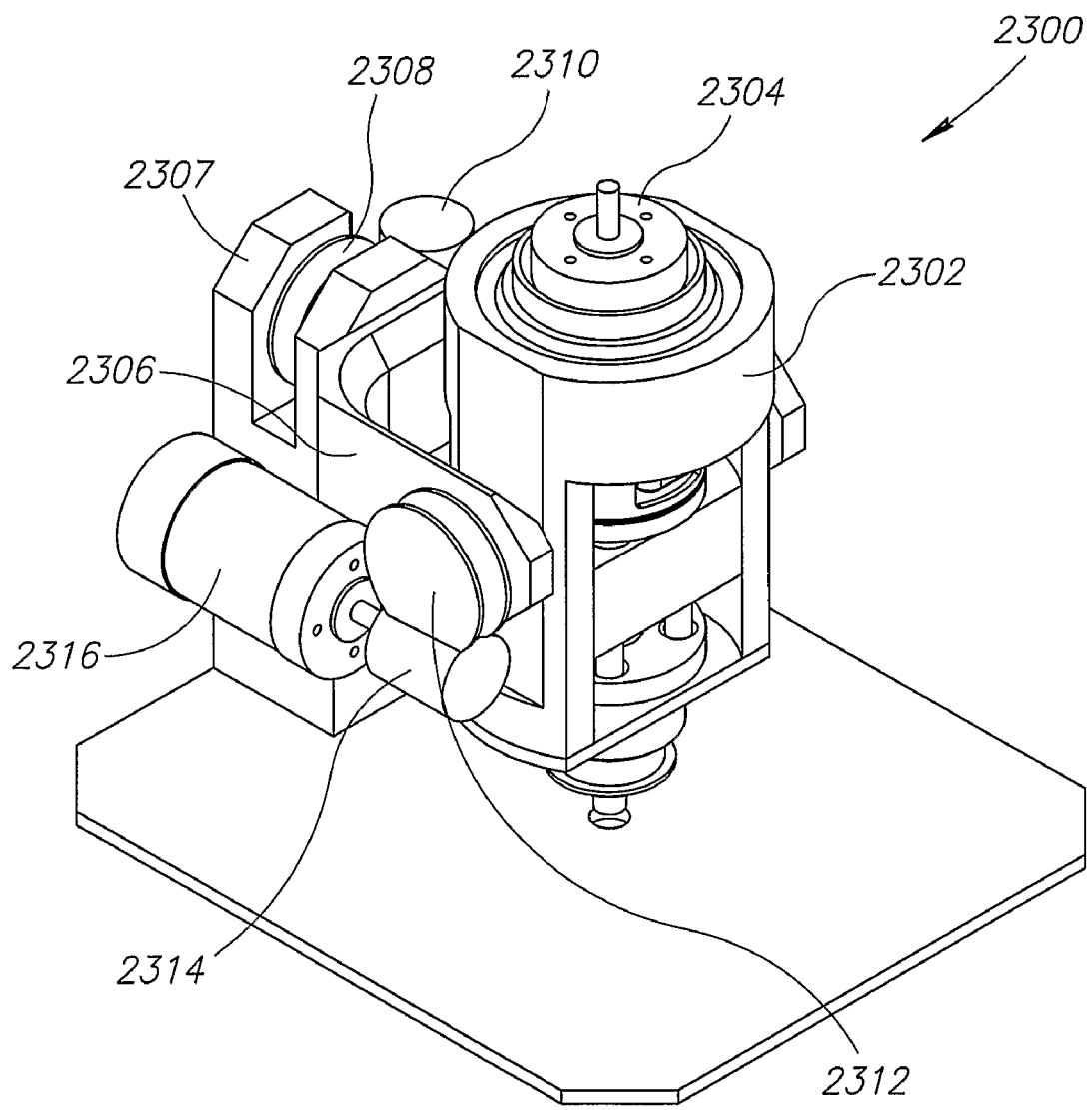
FIG. 23 shows a cantilevered rehabilitation device mechanism, in accordance with an exemplary embodiment of the invention.

FIG. 23 shows a cantilevered gimbaled mechanism 2300 in accordance with an exemplary embodiment of the invention. A frame 2302 is coupled (rigidly or not, as will be described in FIG. 25) to a handle (not shown) which is optionally attachable to a drive system 2304 (e.g., for selectable extension and resistance to axial motion of the handle). Frame 2302 is rotatably coupled to a frame 2306. In an exemplary embodiment of the invention, relative rotation between frames 2302 and 2306 is provided by a motor 2316. In an exemplary embodiment of the invention, motor 2316 couples the frames using a worm gear 2314 and pinion 2312. Other connections methods may be provided. Optionally, the worm gear has a lead angle small enough to prevent motion of the handle from back-driving the motor. Possibly a worm gear is cheaper, quieter and/or allows a lower cost motor to be used, as compared to using a precise motor and/or gear-box.

Frame 2306 is optionally coupled to a base bracket 2307 using a similar mechanism, of which only pinion 2308 and worm 2310 are shown.

Optionally, braking is provided as described in the previous embodiment.

Force Control Mechanism

Figure 24A:
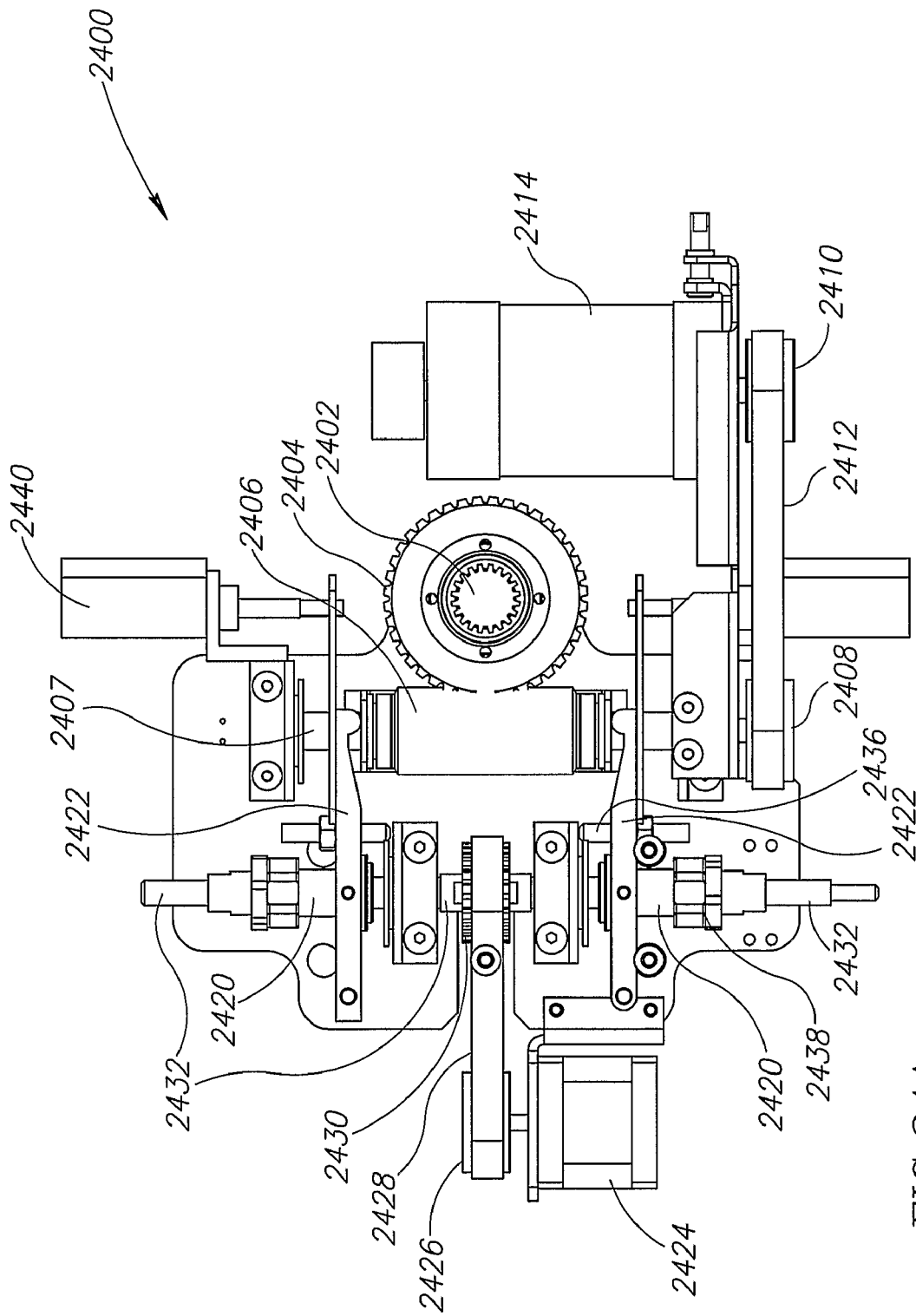
FIG. 24A is a side cross-sectional view of a force control mechanism as used in FIG. 22B, in accordance with an exemplary embodiment of the invention.

FIG. 24A shows a force and drive control mechanism 2400, in accordance with an exemplary embodiment of the invention. As shown, mechanism 2400 includes a drive section and a force feedback section. One or both of these sections may be omitted in some embodiments.

Referring first to the drive section, an axle (not shown) of hinge 2220 or 2214 is coupled to an inner pinion section 2402 of a pinion 2404, for example via a gear section formed on the axle. Optionally, other attachment methods, for example direct attachment, are used. Pinion 2404 is rotated by a worm gear 2406 which turns on an axis 2407. In an exemplary embodiment of the invention, power is provided by a motor 2414 via a set of two pulleys 2408 and 2410 connected by a belt 2412. Other power trains may be used as well.

Referring to the force feedback section, in an exemplary embodiment of the invention, worm gear 2406 has a lead angle small enough so that it cannot be back-driven by pinion 2404. Instead, force (e.g., from the handle) which counteracts the force applied by motor 2414 will cause worm gear 2406 to move axially along axis 2407. Optionally, one or both of a viscous braking mechanism and a resilient resistance mechanism are provided to counteract this force. Various combinations of settings may be provided, for example resulting in what is shown in FIG. 3B.

Axial movement of worm gear 2406 results in displacement of one of the two levers marked 2422 (the figure shows a mirror-imaged mechanism). Viscous cushioning is optionally provided by a cushion 2440 resisting motion of lever 2422. Cushion 2440 is optionally adjustable, for example by hand or by the rehabilitation device. A linear potentiometer or other position sensor, are optionally used to detect the offset of worm gear 2406.

In an exemplary embodiment of the invention, a spring 2420 resists the motion of lever 2422. Optionally, spring 2420 can be selectably preloaded by a motor 2424. In the embodiment shown, a set of pulleys 2426 and 2430 and a belt 2428 cause the rotation of a threaded shaft 2432. In an exemplary embodiment of the invention, a nut 2434 (or other mechanism) rides on the screw and converts its rotation into preload of spring 2420. Optionally, shaft 2432 is threaded in opposite directions on its two ends. It should be appreciated that separate preloading for each of the two springs 2420 may be provided, for example if an asymmetric force resistance is desired, or to counter-balance for gravity. Optionally, manual adjustment of preloading is provided by a nut 2438, possibly used for initial calibration and setting.

Optionally, a pin 2436 is provided to limit the axial extent of motion of worm gear 2406. It should be noted that if the preload is above zero, axial motion of worm gear 2406 will not occur until this force is overcome. This corresponds to $F_{min}$ in FIG. 3B. Optionally, the force mechanism is set up so that there is more resistance to extending motion (away from the body) than to motion towards the body.

Other mechanical structures can be provided as well, for example, springs 2420 can sit on axis 2407. In another example, instead of motor 2424 and the associated pre-load setting mechanism can be replaced by a single spring coupled between the two levers 2422.

This structure can provide various modes of operation for example:

a) User passive mode. In this mode, motor 2414 drives worm gear 2406 and worm gear 2406 rotates pinion gear 2404 that is connect to the handle.

b) Free user mode. In this mode, a user moves the handle in any user determined direction and the system follows the user. In this embodiment, mechanism 2400 acts as a mechanical diode is used to decouple the user motion from the motor. As the user exerts force on the robot arm, worm gear 2406 moves axially as described above. This linear motion is measured and can be used as input to a controller. The amount of force felt by the user is generally determined by the preload of spring 2420. The preload can be set or as in this case be controlled by the motorized preload motor.

In the free user mode the controller receives the input from the linear potentiometer and instructs motor 2424 to follow in the same direction. This causes the user to a predetermined force counteracting his desired motion.

c) Restricted mode (force field). An additional use for the spring motor combination is to create a track where the counteracting force is minimal but any deviation from the track will result in higher spring displacement and thus a force opposite the deviation (e.g., as shown in FIG. 3A). Optionally, this mode is activated for a particular speed, thereby setting up an isokinetic exercise.

d) Initiated Mode. A user starts a motion in a certain direction, which will be sensed as displacement of worm gear 2406. This motion can then be carried to completion by the rehabilitation device. Optionally, the motion will be completed only if the initiated move was in a predetermined direction.

e) Assist mode. When a motion is in progress, spring 2420 is preloaded in a fashion which pushes the handle in the direction of the motion (e.g., positive feedback). This may be a continuous force or it may be provided in pulses.

f) Static. Optionally, the force mechanism is used to require a patient to apply a force at a point in space without substantial movement of the handle. The force can be measured and/or controlled on the fly. It should be noted that a spring mechanism can generally provide more realistic small motions in response to force than a friction mechanism or direct robotic motion using motors.

A potential advantage of the spring-motor combination is that velocity and/or range limitations on motion can be provided. Another potential advantage is that gradual (e.g., resilient) stopping can be provided, even in an emergency stop. Another potential advantage is that the viscous damping can provide a dynamic feeling.

Figure 24B:
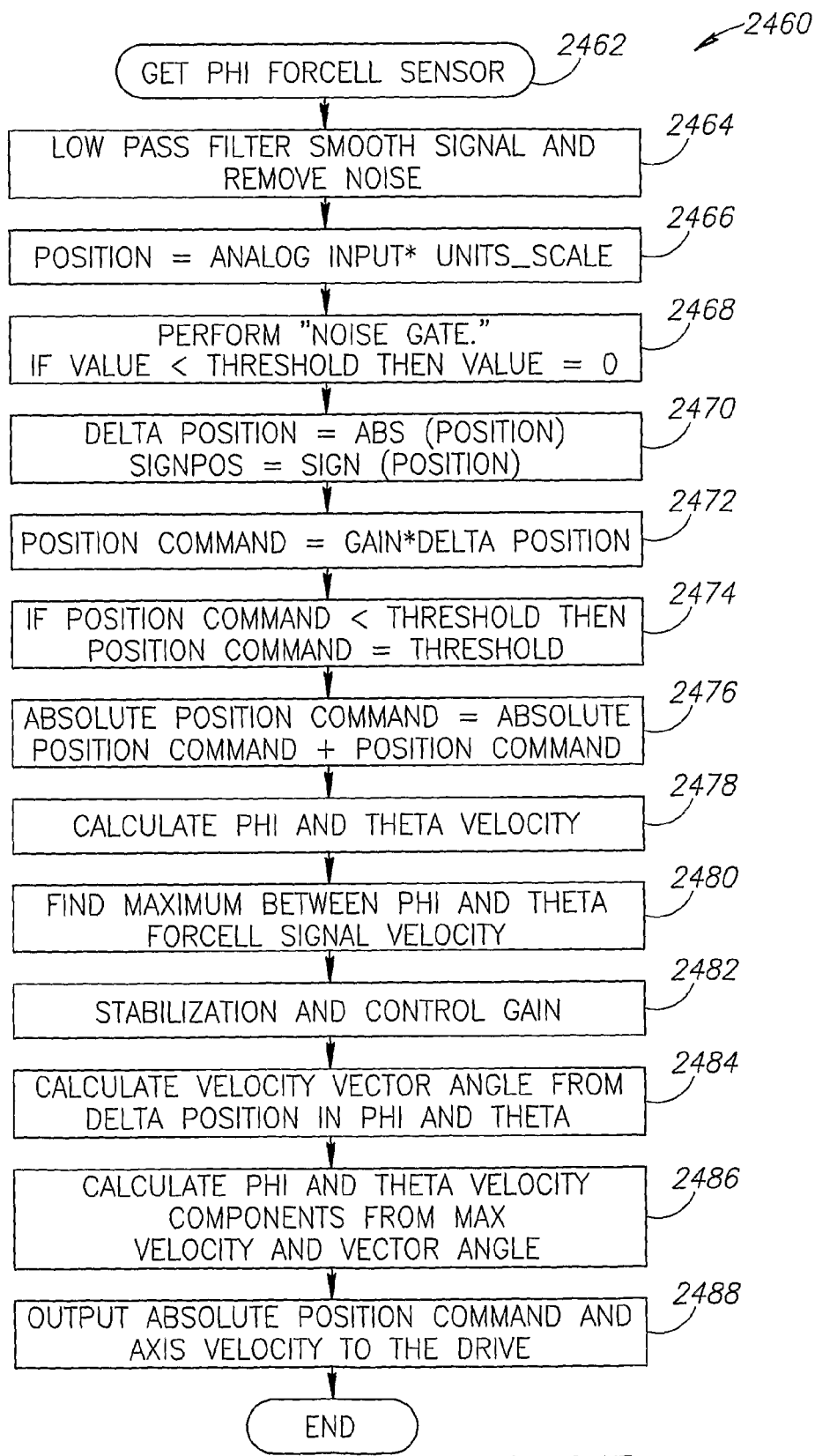
FIG. 24B is a flowchart of the operation of the mechanism of FIG. 24A, in accordance with an exemplary embodiment of the invention.

FIG. 24B is a flowchart 2460 of the operation of mechanism 2400 when two such mechanisms are attached to the device of FIG. 22B, in a free-hand mode, in accordance with an exemplary embodiment of the invention. A similar process may be used for implementation with force control in three axes.

Flowchart 2460 describes how the magnitude and direction of force applied by a user is measured and then used to guide the motion of the handle. Acts 2462 through 2476 are described only for Phi, but are carried out for all axes (e.g., Theta), as well.

At 2462, measurement of the Phi offset is acquired.

At 2464 optional filtering is applied, for example low pass filtering which smoothes the signal and/or removes noise.

At 2466, a scaling operation is optionally performed, for example to match calibration and control parameters.

At 2468, a noise gate is optionally applies where signals below a threshold are converted to zero.

At 2470, the magnitude and/or direction of the change in position are optionally extracted.

At 2472, a position command is optionally generated using a gain factor.

At 2474, the position command is optionally clamped to be at least a minimal value, for example, to overcome friction and/or noise levels.

At 2476, an absolute position command is optionally generated.

At 2478, the velocities of Phi and Theta axes are calculated. Optionally, acceleration is calculated as well.

At 2480, a composite vector of correction is found. Optionally, the composite vector is a maximum of phi and theta rather than a vector combination, this may serve to stabilize the system and/or prevent mechanical problems.

At 2482, a gain smaller than 1 is optionally applied, possibly increasing the stability.

At 2484, the angle of the velocity vector is optionally calculated.

At 2486, the components for Phi and Theta velocity are calculated.

At 2488, a command for the motive source (e.g., motors) is generated.

Coupled Force Control Mechanism

Figure 25:
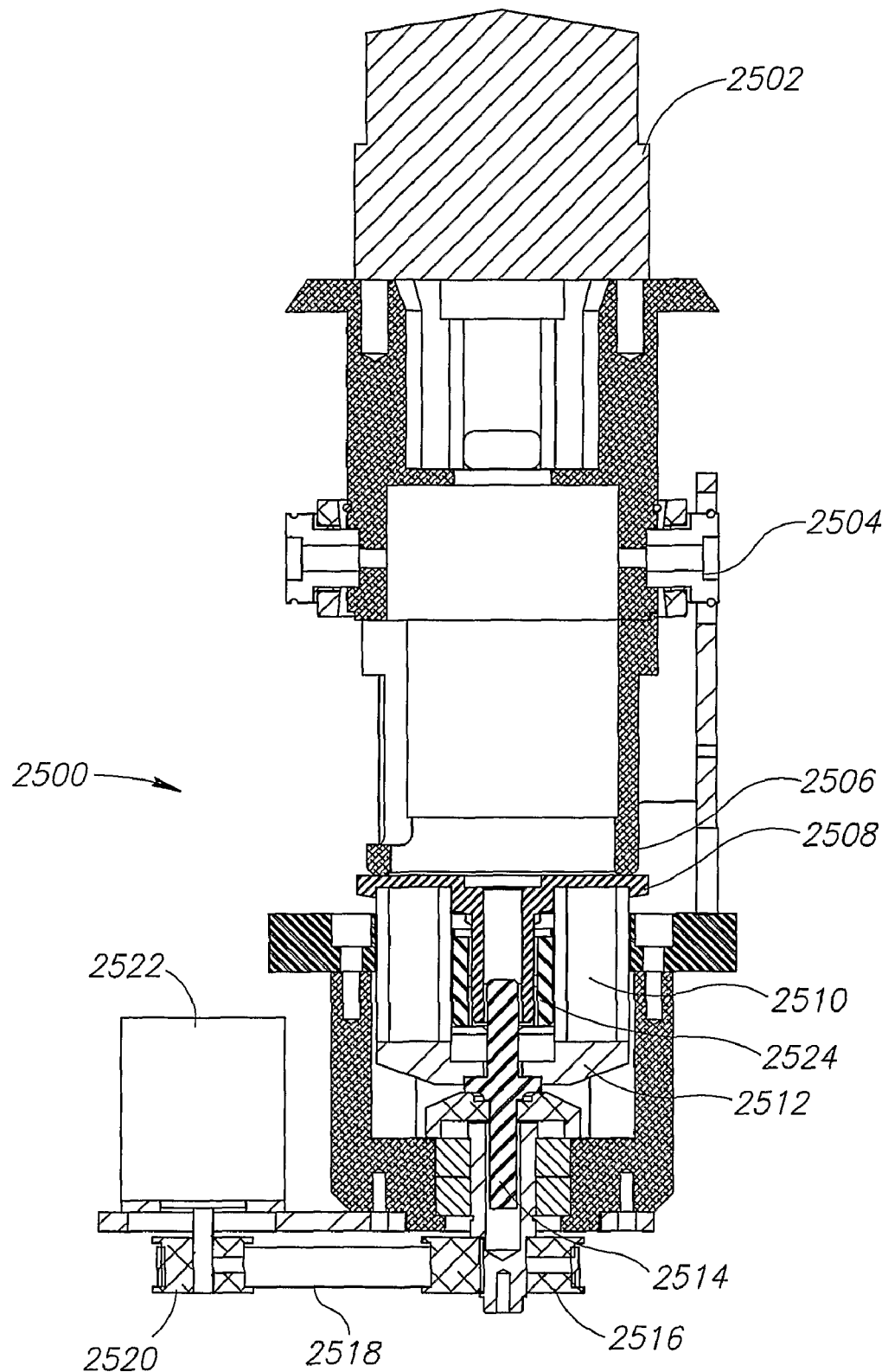
FIG. 25 shows a force control mechanism in accordance with an alternative embodiment of the invention.

FIG. 25 shows an alternative force control mechanism 2500 in which Phi and Theta axes are coupled using a single spring mechanism. A handle 2502 is moved using axes not shown. In one example, mechanism 2500 comprises an inner mechanism of the embodiment described in FIG. 23 (where external Phi and Theta axes are shown).

An axis 2504 (and a matching orthogonal axis, not shown) comprise inner Phi and Theta axes which handle 2502 rotates around a small amount when force control is applied. A bottom part 2506 contacts a plate 2508. The small amount of rotation causes plate 2508 to be depressed by part 2506 (other shapes may be provided, but part 2506 is optionally rounded at its circumference). This depression is resisted by one or more springs 2510, for example four springs. The pre-load of the springs may be set using a motor 2522 which using a driver train comprising pulleys 2520 and 2516 and a belt 2518 can rotate a screw 2514 which compresses springs 2510 by lifting a base 2512. Alternatively or additionally, manual pre-loading may be practiced Optionally, linear motion of plate 2508 is ensured using a bushing 2524 or other means as known in the art. A mechanical stop may be provided to the relative motion of cap 2508 and base 2512, so that sufficient preload of springs 2510 prevents any mechanical motion.

The rounding of the edges of part 2506 may be calculated to ensure a linear relationship between angle of rotation and displacement.

The axes of inner rotation may be congruent with the axes of external rotation, however, this is not required. For example, the axes may not be co-planar and/or the axes may not be parallel.

Various measurement means may be provided, for example, a linear potentiometer measuring spring displacement and/or rotary potentiometers measuring Phi and Theta rotation. Measured values may be used with the flowchart of FIG. 24B.

Optionally, spring 2510 is used to also provide compliance in the Z-direction. In one example, when handle 2502 is depressed, spring 2510 provides resistance. The hinge at axis 2504 is optionally placed in a slot is that z-axial motion of the hinge is possible.

Z-Axis Motion Mechanism

Figure 26B:
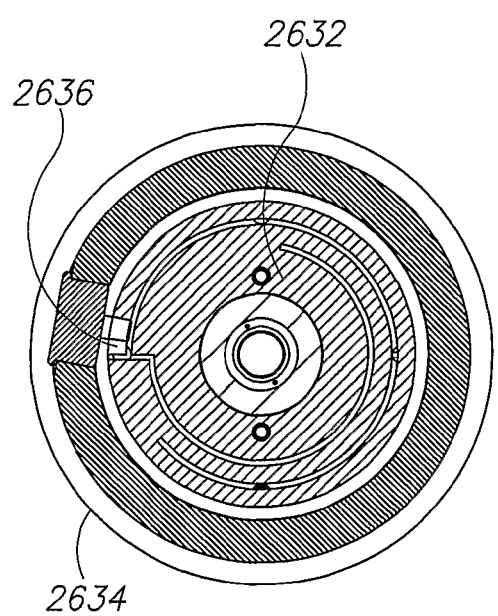
FIG. 26B shows a force control mechanism for an attachment, exemplified as part of FIG. 26A, in accordance with an exemplary embodiment of the invention.
Figure 26A:
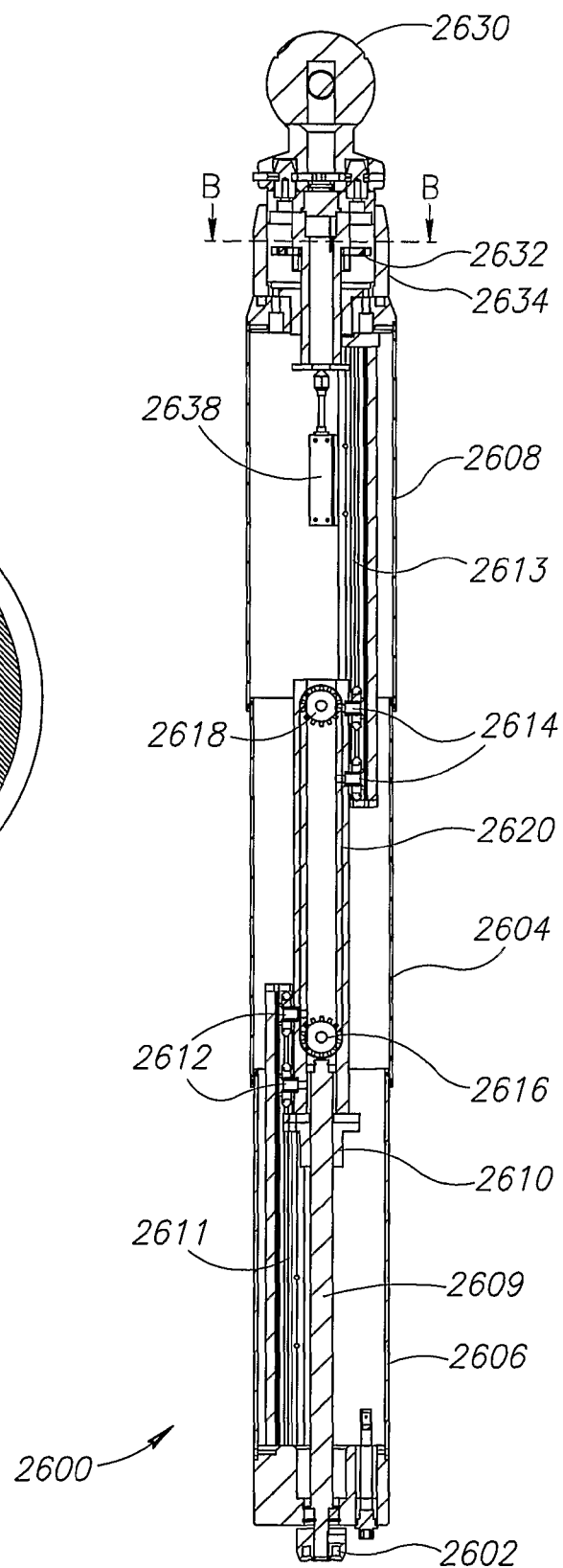
FIG. 26A shows a Z-axis extension mechanism in accordance with an exemplary embodiment of the invention.

FIGS. 26A and 26B shows a z-axis motion and force response mechanism 2600, in accordance with an exemplary embodiment of the invention. The mechanism comprises a three part telescoping rod comprising a central portion 2604, a top portion 2608 and a bottom portion 2606. An external motor (e.g. 2304 from FIG. 23) couples to a coupling 2602 and thereby rotates a rod 2609. The use of an external motor optionally helps modularity as a z-axis mechanism can be made lower cost and interchangeable with other z-axis mechanisms. A coupling 2610, for example a nut converts the rotary motion into axial motion of central portion 2604. The telescoping of portions 2604, 2606 and 2608 is optionally guided by a pair of linear bearings, 2614 for portion 2608 and 2612 for portion 2606. The linear bearings lie in cannels 2613 and 2611, respectively.

In an exemplary embodiment of the invention, a combined rack and pinion and timing belt mechanism is used to synchronize the extension of portions 2606 and 2608, as follows. Each of the channels 2611 and 2613 also includes a rack defined thereon and portion 2604 includes two pinions 2616 and 2618, one on either end. When portion 2604 extends, rack 2611 causes pinion 2616 to rotate. A timing belt 2620 which is connected between pinions 2616 and 2618 (on co-axially coupled belt pulleys of same effective diameter) causes pinion 2618 to rotate in synchronization. Pinion 2618 then moves rack 2613, causing telescoping of portion 2608.

In an exemplary embodiment of the invention, telescoping allows the z-axis mechanism to be compact and assist in portability. Also, it allows motions near to the center of rotation of the motion mechanism. In an exemplary embodiment of the invention, telescoping allows a range of 2:1 or close to 3:1 of z-axis length. Additional telescoping potions can be provided for a greater extension ratio.

Referring to the upper part of the z-axis mechanism, an exchangeable handle 2630 is shown. Axial motion of handle 2630 is optionally shown by motion of a linear measurement potentiometer 2638. Optionally, handle 2630 is attached using a quick connect mechanism.

In an exemplary embodiment of the invention, a spring 2632 provides resilient resistance to axial motion of handle 2630, for example using the logic as described above in FIG. 24.

Referring to FIG. 26B, spring 2632 is a spiral spring, whose resistance can be changed by changing its effective length, for example by moving a sliding stop 2636 which determines a length of the leaves of spring 2632. This sliding stop is optionally moved manually, for example by rotating a housing 2634. Alternatively, an internal motor may be provided. This change in leaf length is generally comparable to a change in preload. Minimal force setting may be provided by actually preloading spring 2636, for example by axial motion thereof, or by providing another spring to resist axial motion. Preload may also be achieved by rotating spring 2632 itself, thereby tensing the spring.

The range of motion of the force control mechanisms can be, for example, 3 cm, 5 cm, 10 cm, 15 cm, 20 cm or intermediate, smaller or greater ranges, depending on the implementation.

It should be noted that in some embodiments of the invention the use of gear-reduction ratios allows lower power and/or lower cost motors to be used.

It should be noted that force in the Z-axis can be transferred using a flexible or a bent coupling. Thus, for example, the z-axis element can be a 90 degree elbow in which only the far portion extends. Alternatively or additionally, goose-neck like mechanism is used to define shape in space for the z-axis element.

Games

Various games have been mentioned. In an exemplary embodiment of the invention, one or more of the following game-types is provided: role playing games (adventure and D&D games), kinetic games (shoot-em-up), board games and simulation games (e.g., soccer and tennis).

Games may be played, for example, one-on-one, against a human opponent or against a machine opponents.

In an exemplary embodiment of the invention, device 100 serves as an input device, for example replacing a joystick. Alternatively or additionally, device 100 is used as a VR input device, for example to read limb positions. Alternatively or additionally, specialized input modes may be defined, for example, spatial positions of arm 102 may be mapped to virtual positions on the screen or in the game world, or to velocities and/or accelerations thereof. Gestures may be defined for various controls, for example, "fire", "lift" and "put" commands may each have an associated gesture.

In an exemplary embodiment of the invention, child games are provided, for example for encouraging paretic or CP children to avoid neglecting body parts. Device 100 may also be used as a social focal point for preventing the paretic child from becoming an outcast.

In an exemplary embodiment of the invention, a game is fitted to the ability of the patient, for example, limiting the ROM required, providing enhancement of patient motion, changing the game speed and changing the visual field which needs to be attended.

In an exemplary embodiment of the invention, the game is selected to match a motivation level of the patient, for example, a simple game selected for low-motivation patients.

Safety

In an exemplary embodiment of the invention, one or more safety features are provided to prevent injury to a patient. For example, one or more of the following safety mechanism may be used:

a) Dead man switch. If a patient releases this switch (or touches a suitable button) movement of device 100 is frozen and/or all forces and resistance brought to zero. Other "safe harbor" configurations can be defined instead.

b) Tearing pin. A pin may be used to attach tip 1008 (or other attachment) to arm 1002. If a certain threshold force is exceeded, the pin tears and the attachment is released from the arm. Different pins with different tearing thresholds may be selected for different situations. Optionally a wire can be attached to the pin for feedback. Optionally the pin comprises two magnetically attracted materials, with the degree of attraction optionally set by electrical current.

c) Locking. Arm 1002 may have an initial locking condition, to allow a patient to lean on it.

d) Voice activation. Voice activation and/or deactivation may be provided, to allow a patient to shout the system to a stop.

e) Analysis. Optionally, the actual movements and/or forces applied by a patient are analyzed to determine if a threshold is being approached or if the patient is experiencing undue stress.

f) Resiliency. The force control mechanism with a spring prevents sudden stops from suddenly stopping the patient. Instead, the spring allows some compliance and a more gradual stop.

g) Force-measured. If the force mechanism determines a force and/or spatial divergence above a threshold, the motion can be stopped and optionally moved opposite to the direction of force application.

Balance Training

In an exemplary embodiment of the invention, a rehabilitation module is used for balance training. In one example, a seat is attached to tip 1008 and a patient sits on the seat. A non-rotating plate 1020 with a slot sets the direction in which the seat is allowed to roll and the resistance level sets the difficulty. Optionally, a handle bar is provided. Alternatively or additionally, a foot rest and/or pedals are provided for the feet. Alternatively one or more rehabilitation modules for the arms are provided. In this manner, various daily and sports activities can be simulated and trained for. Optionally, a virtual reality type display or a television display are provided to enhance the sense of reality. Such a virtual reality display may be provided in other embodiments of the invention, for example to show feedback, to show instructions or to make the activity more interesting.

U.S. provisional application No. 60/633,442 filed on Dec. 7, 2004, also being filed as PCT application on same date as the present application and by the same applicant, entitled "Methods and Apparatuses for Rehabilitation Exercise and Training", the disclosures of which are incorporated herein by reference, describes training of balance, for example, using such a chair. Optionally, a full body system is used to train multiple body parts associated with balance simultaneously, for example, torso, arms and/or legs.

In an exemplary embodiment of the invention, device 100 is used to train balance while standing. For example, a patient performing a reaching exercise to arm 102, when tip 108 is at various spatial positions; some positions requiring only arm extending and some positions requiring torso bending.

Multi-Modal Therapy and Coordination Training

In an exemplary embodiment of the invention, device 100 can be used for providing rehabilitation in modes other than motor. In one example, the displays (audio and/or visual) are used to perform visual and/or auditory rehabilitation. Thus, a single device can be used for multiple rehabilitation types (e.g., at home) and serve as a single point of contact both for the patient and for the therapist. If multiple therapists exist, the device can serve to coordinate between the various therapies and/or track general parameters, such as general progress, motivation and/or cognitive level. In an exemplary embodiment of the invention, device 100 selectively applies an exercise in one of several modalities, for example, for load balancing and/or for interest.

In an exemplary embodiment of the invention, device 100 is used to rehabilitate the coordination between modalities and/or using the rehabilitation of one modality to help rehabilitate other modalities. One example is eye-hand coordination, where a patient is shown a target on a screen and the aim is to move tip 108 to tack it. Another example is timing where a patient needs to provide a command at a certain timing, possibly in an auditory modality. Another example is spatial planning, where a patient is provided with verbal instructions of gradually increasing complexity with regard to spatial motions.

In an exemplary embodiment of the invention, progressively more complex visual instructions, motor acts and feedback (visual or not) are provided to the patient. Similarly, progressively more complex audio, kinesthetic, haptic, and smell (using scent release attachments) feedback and/or instructions are provided.

In a particular example, speech recognition is rehabilitated in concert with motion for example requiring speech to be understood fast enough to perform the motion in time, or respond to verbal instructions. A user may be required to provide speech utterances which match his motions. A speech recognition module may be provided.

In another example, visual stimuli is made more complex as visual rehabilitation progresses, for example, starting with a light, then a light at a position, then a speed of blinking, then text which must be read, all of which are used to prompt motor action or serve as feedback (e.g., for progressively complex motor tasks: moving arm, moving to a direction, moving to a particular area).

A particular advantage of some embodiments of device 100 is mechanical feedback and support is provided to the patient. In some embodiments, some of the methods described herein for motor rehabilitation (and which may find special utility therefor) are used for non-motor rehabilitation, for example, measuring motivation, remote rehabilitation, group activities and support by a computer of user activities (for example for group participation).

Other Devices

Various designs for robots and positioning devices (e.g., hexapods) are known in the art. It should be appreciated that various ones of the statements described herein may be adapted for such robots and/or positioning devices, in accordance with exemplary embodiments of the invention. Alternatively or additionally, software may be provided for such robots and devices for carrying out various ones of the methods described herein, all in accordance with exemplary embodiments of the invention.

U.S. provisional application No. 60/604,615 filed on Aug. 25, 2004, the disclosure of which is incorporated herein by reference, describes taking the effects of brain plasticity into account. The methods described herein may use EEG or fMRI as an input for deciding, for example, on feedback or type of device mode to use.

U.S. Provisional Application 60/566,078 filed on Apr. 29, 2004, also being filed as PCT application on same date as the present application and by the same applicant, entitled "Neuromuscular Stimulation", the disclosures of both applications are incorporated herein by reference, describe stimulating a paretic limb while moving the limb or otherwise supporting the motion of the limb. EMG measurements, for example of healthy limbs are optionally used as part of the teaching of the present application for deciding on stimulation and/or supported motion of a paretic limb.

It should be noted that the rehabilitation devices described herein are optionally usable not only at a home but also at care centers, such as old age homes, hospitals and rehabilitation centers.

It will be appreciated that the above described methods of rehabilitation may be varied in many ways, including, omitting or adding steps, changing the order of steps and the types of devices used. In addition, a multiplicity of various features, both of method and of devices have been described. In some embodiments mainly methods are described, however, also apparatus adapted for performing the methods are considered to be within the scope of the invention. It should be appreciated that different features may be combined in different ways. In particular, not all the features shown above in a particular embodiment are necessary in every similar embodiment of the invention. Further, combinations of the above features are also considered to be within the scope of some embodiments of the invention. Also within the scope of the invention are kits which include sets of a device, one or more tearing pins, one or more attachments and/or software. Also, within the scope is hardware, software and computer readable-media including such software which is used for carrying out and/or guiding the steps described herein, such as control of arm position and providing feedback. Section headings are provided for assistance in navigation and should not be considered as necessarily limiting the contents of the section. When used in the following claims, the terms "comprises", "includes", "have" and their conjugates mean "including but not limited to". It should also be noted that the device is suitable for both males and female, with male pronouns being used for convenience.

It will be appreciated by a person skilled in the art that the present invention is not limited by what has thus far been described. Rather, the scope of the present invention is limited only by the following claims.

The invention claimed is:

1. A rehabilitation device, comprising:
   an actuator that includes a movement mechanism capable of applying a force that interacts with a motion along a rehabilitation exercise trajectory of a patient's limb in a volume of at least 30 cm in diameter and capable of preventing substantial motion in any point in any direction in said volume;
   a support for a patient;
   a controller adapted to adjust the rehabilitation exercise trajectory according to the relative positions of said actuator and at least one of said patient and said support; and,
   a compliance mechanism adapted to provide resistance to motion of said actuator away from said trajectory.

2. A device according to claim 1, further comprising a coupler which couples said actuator to a point on a human body, wherein said controller drives said actuator to apply a force vector to said point, said force including a rotation.

3. A device according to claim 1, wherein said force vector includes at least two rotations directions relative to the force vector.

4. A device according to claim 1, comprising a second actuator driven by said controller to apply a second force to at least a second point on said body, simultaneously with said force.

5. A device according to claim 1, comprising:
   a coupler for coupling said actuator to a first point on a human body;
   a second actuator that includes a movement mechanism capable of applying a force that interacts with a motion of a patient's limb in a volume of at least 30 cm in diameter, in at least three degrees of freedom of motion of the actuator and capable of preventing substantial motion in any point in any direction in said volume;
   a coupler for coupling said second actuator to a second point on a human body; and
   wherein said controller drives said actuators to apply different forces to said points using said actuators.

6. A device according to claim 5, wherein said first actuator applies a rotation.

7. A device according to claim 5, wherein said different points are on a same limb.

8. A device according to claim 5, wherein said different points are on different limbs.

9. A device according to claim 8, wherein said controller is configured to exercise the two limbs in concert.

10. A device according to claim 8, wherein said controller is configured for copying motion from one limb to the other limb.

11. A device according to claim 1 configured to control a position of at least a second point on the limb; and
wherein said controller is configured to reconstruct a value of a bending of at least one joint of said organ from said motion and said position.

12. A device according to claim 1, comprising a distance sensor for determining said relative positions.

13. A device according to claim 1, comprising an imaging sensor for determining said relative positions.

14. A device according to claim 1, wherein said controller relates to the relative placement of said patient and said actuator.

15. A device according to claim 1, wherein said controller assumes the relative positions differ only in two dimensions.

16. A device according to claim 1, comprising a pointer which indicates a desired patient placement.

17. A device according to claim 1, wherein said controller is configured to use said actuator to determine said relative placement.

18. A device according to claim 1, wherein said controller is configured to use said actuator to indicate a desired relative placement.

19. A device according to claim 1, wherein said controller is configured to adjust said exercise on the fly, during an exercise session and in response to patient movement.

20. A rehabilitation device according to claim 1, comprising:
a memory storing therein a correspondence between exercises and payment codes;
wherein said controller is adapted to generate a report including a code from said memory corresponding to said exercise.

21. A rehabilitation device according to claim 1, further comprising:
at least one sensor associated with the actuator and measuring said motion; wherein
the controller analyses said measured motion and generates a measure of quality of motion and modifies a rehabilitation plan responsive to said quality of motion measure.

22. A device according to claim 21, wherein the controller modifies a selection of future exercises according to a measured quality of motion.

23. A device according to claim 21, wherein the controller modifies a selection of parameters for future exercises according to a measured quality of motion.

24. A device according to claim 21, wherein the quality of motion measure used is defined as the degree of matching to a ⅔ power law.

25. A device according to claim 1, wherein said controller is configured to:
cause a person to carry out at least one exercise;
estimate a mental state of said person from a result of said at least one exercise; and
automatically select at least one second exercise according to said estimation.

26. A device according to claim 25, wherein said controller estimates a mental state using a comparing of performance between two exercises, one or which is expected to elicit a higher compliance.

27. A device according to claim 25, wherein said controller estimates a mental step using a comparing of performance within an exercise, using the maximum ability of the patient as a base line against which variation can be determined.

28. A device according to claim 25, wherein said estimating is automatic.

29. A device according to claim 1, wherein said controller is configured to:
determine a patient's ability to perform a motor task;
determine a patient's ability to perform a non-motor task; and
automatically select an exercise or parameters of an exercise for the patient according to said determinations.

30. A device according to claim 29, wherein said controller is configured to select using a matching of an instruction or feedback modality to a perceptive ability.

31. A device according to claim 29, wherein said controller is configured to selected using a matching of an instruction or feedback modality to a cognitive ability.

32. A device according to claim 29, wherein said controller is configured to select an exercise or series of exercises designed to rehabilitate both of said motor and said non-motor abilities.

33. A device according to claim 29, wherein said exercise rehabilitates visual-motor coordination.

34. A device according to claim 1, wherein said actuator includes a tip which said actuator moves to a spatial location and wherein said controller is configured to
instruct a patient to apply force against said tip, wherein said actuator provides a compliant resistance to said force.

35. A device according to claim 34, wherein said controller is configured to select the resistance according to the spatial location.

36. A device according to claim 1, wherein said controller is configured to adjust a force applied during said exercise, based on one or more patient characteristics.

37. A device according to claim 1, wherein the compliance mechanism comprises at least one brake.

38. A device according to claim 1, wherein the compliance mechanism comprises at least one resilient element.

39. A device according to claim 1, wherein the compliance mechanism is adapted to have variable compliance for at least one of different rehabilitation exercises or within a single rehabilitation exercise.

\* \* \* \* \*